US012006304B2

(12) United States Patent
Bothe et al.

(10) Patent No.: US 12,006,304 B2
(45) Date of Patent: *Jun. 11, 2024

(54) SUBSTITUTED INDAZOLES, METHODS FOR THE PRODUCTION THEREOF, PHARMACEUTICAL PREPARATIONS THAT CONTAIN SAID SUBSTITUTED INDAZOLES, AND USE OF SAID SUBSTITUTED INDAZOLES TO PRODUCE DRUGS

(71) Applicant: Bayer Pharma Aktiengesellschaft, Berlin (DE)

(72) Inventors: Ulrich Bothe, Berlin (DE); Holger Siebeneicher, Berlin (DE); Nicole Schmidt, San Francisco, CA (US); Reinhard Nubbemeyer, Berlin (DE); Ulf Bömer, Glienicke (DE); Judith Günther, Berlin (DE); Holger Steuber, Berlin (DE); Martin Lange, Berlin (DE); Christian Stegmann, Berlin (DE); Andreas Sutter, Berlin (DE); Alexandra Rausch, Berlin (DE); Christian Friedrich, Brandenburg (DE); Peter Hauff, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/869,674

(22) Filed: Jul. 20, 2022

(65) Prior Publication Data
US 2022/0388982 A1 Dec. 8, 2022

Related U.S. Application Data

(63) Continuation of application No. 17/009,553, filed on Sep. 1, 2020, now abandoned, which is a continuation of application No. 16/377,025, filed on Apr. 5, 2019, now Pat. No. 10,793,545, which is a continuation of application No. 15/529,996, filed as application No. PCT/EP2015/077596 on Nov. 25, 2015, now Pat. No. 10,308,634.

(30) Foreign Application Priority Data

Nov. 26, 2014  (EP) ..................................... 14195032

(51) Int. Cl.
| C07D 401/12 | (2006.01) |
| A61K 31/4439 | (2006.01) |
| A61P 19/02 | (2006.01) |
| C07D 405/14 | (2006.01) |
| C07F 7/18 | (2006.01) |

(52) U.S. Cl.
CPC ........ C07D 401/12 (2013.01); A61K 31/4439 (2013.01); A61P 19/02 (2018.01); C07D 405/14 (2013.01); C07F 7/1804 (2013.01)

(58) Field of Classification Search
CPC ... A61K 31/4439; A61P 19/02; C07D 405/14; C07D 401/12
USPC .......................................................... 514/63
See application file for complete search history.

(56) References Cited

U.S. PATENT DOCUMENTS

| 8,293,923 B2 | 10/2012 | Guckian et al. |
| 9,073,892 B2 | 7/2015 | Jorand-lebrun et al. |
| 9,951,086 B2 | 4/2018 | Bothe |
| 10,308,634 B2* | 6/2019 | Bothe ................. C07D 405/14 |
| 10,435,396 B2 | 10/2019 | Bothe |
| 10,501,417 B2 | 12/2019 | Thaler |
| 10,501,437 B2 | 12/2019 | Thaler |
| 10,633,365 B2 | 4/2020 | Thaler |
| 10,759,758 B2 | 9/2020 | Thaler |
| 10,793,545 B2* | 10/2020 | Bothe ................. C07D 405/14 |
| 2007/0185058 A1 | 8/2007 | Conte et al. |
| 2010/0298377 A1 | 11/2010 | Aletru et al. |

(Continued)

FOREIGN PATENT DOCUMENTS

| EP | 1997800 A4 | 11/2010 |
| EP | 2489663 A1 | 8/2012 |

(Continued)

OTHER PUBLICATIONS

Abbate, A. et al. (2010). "Interleukin-1 Blockade With Anakinra to Prevent Adverse Cardiac Remodeling After Acute Myocardial Infarction (Virginia Commonwealth University Anakinra Remodeling Trial [VCU-ART] Pilot Study," The American Journal of Cardiology 105: 1371-1377.

Abbate, A. et al. (2013). "Effects of Interleukin-1 Blockade With Anakinra on Adverse Cardiac Remodeling and Heart Failure After Acute Myocardial Infarction [from the Virginia Commonwealth University-Anakinra Remodeling Trial (2) (VCU-ART2) Pilot Study]," 111: 1394-1400.

(Continued)

*Primary Examiner* — Kahsay Habte
(74) *Attorney, Agent, or Firm* — Morrison & Foerster LLP

(57) ABSTRACT

The present application relates to novel substituted indazoles, to processes for preparation thereof, to the use thereof alone or in combinations for treatment and/or prophylaxis of diseases, and to the use thereof for production of medicaments for treatment and/or prophylaxis of diseases, especially for treatment and/or prophylaxis of endometriosis and endometriosis-associated pain and other endometriosis-associated symptoms such as dysmenorrhoea, dyspareunia, dysuria and dyschezia, of lymphoma, rheumatoid arthritis, spondyloarthritis (especially psoriatic spondyloarthritis and Bekhterev's disease), lupus erythematosus, multiple sclerosis, macular degeneration, COPD, gout, fatty liver disorders, insulin resistance, neoplastic disorders and psoriasis.

9 Claims, 4 Drawing Sheets

(56) References Cited

U.S. PATENT DOCUMENTS

Figure 1:
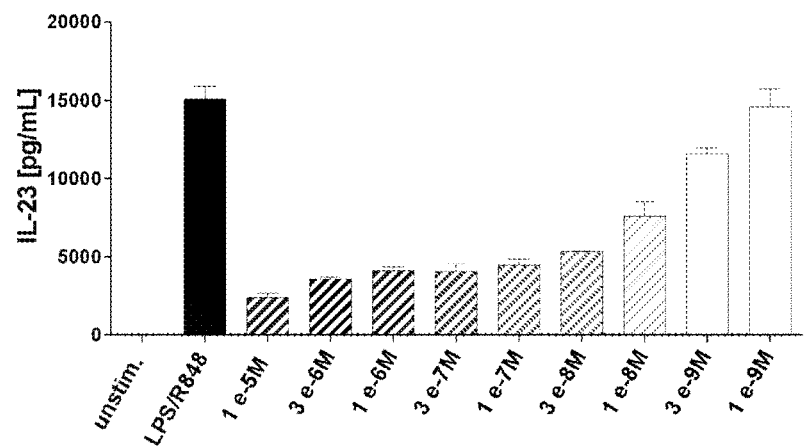

| | | |
|---|---|---|
| 2011/0152260 A1 | 6/2011 | Guckian et al. |
| 2012/0238559 A1 | 9/2012 | Baldwin et al. |
| 2013/0274241 A1 | 10/2013 | Jorand-Lebrun et al. |
| 2018/0201609 A1 | 7/2018 | Gummadi et al. |
| 2018/0289685 A1 | 10/2018 | Bothe |
| 2019/0125736 A1 | 5/2019 | Rausch |
| 2019/0388410 A1 | 12/2019 | Bothe |
| 2020/0216413 A1 | 7/2020 | Beddies |
| 2022/0241261 A1 | 8/2022 | Bothe et al. |
| 2022/0249456 A1 | 8/2022 | Rausch et al. |
| 2023/0174508 A1 | 6/2023 | Bothe et al. |

FOREIGN PATENT DOCUMENTS

| | | |
|---|---|---|
| IN | 146/CHE/2014 | 1/2014 |
| IN | 3018/CHe/2014 | 6/2014 |
| JP | 2013512878 A | 4/2013 |
| JP | 2014500286 A | 1/2014 |
| JP | 2015002717 A | 1/2015 |
| WO | 2004013102 A1 | 2/2004 |
| WO | 2004113281 A1 | 12/2004 |
| WO | 2005082866 A3 | 4/2006 |
| WO | 2006061715 A3 | 11/2006 |
| WO | 2006116412 A8 | 3/2007 |
| WO | 2007031265 A3 | 7/2007 |
| WO | 2007091107 A1 | 8/2007 |
| WO | 2008030584 A2 | 3/2008 |
| WO | 2009117421 A3 | 1/2010 |
| WO | 2011153588 A1 | 12/2011 |
| WO | 2012061926 A1 | 5/2012 |
| WO | 2012107475 A1 | 8/2012 |
| WO | 2012112743 A1 | 8/2012 |
| WO | 2013106254 A1 | 7/2013 |
| WO | 2013174744 A1 | 11/2013 |
| WO | 2015091426 A1 | 6/2015 |
| WO | 2015104662 A1 | 7/2015 |
| WO | 2015193846 A1 | 12/2015 |
| WO | 2016174183 A1 | 11/2016 |
| WO | 2017148902 A1 | 9/2017 |
| WO | 2017157792 A1 | 9/2017 |
| WO | 2017186689 A1 | 11/2017 |
| WO | 2017186693 A1 | 11/2017 |
| WO | 2017186700 A1 | 11/2017 |
| WO | 2017186703 A1 | 11/2017 |
| WO | 2017207386 A1 | 12/2017 |
| WO | 2017207481 A1 | 12/2017 |

OTHER PUBLICATIONS

Ahmad, R. et al. (2015). "Increased expression of the interleukin-1 receptor-associated kinase (IRAK)-1 is associated with adipose tissue inflammatory state in obesity," Diabetology & Metabolic Syndrome 7(71): 1-16.

Akash, M.S.H. et al. (2012). "Interleukin-1 Receptor Antagonist: A New Therapy for Type 2 Diabetes Mellitus," Journal of Pharmaceutical Sciences 101(5): 1647-1658.

Akcay, A. et al. (2011). "IL-33 Exacerbates Acute Kidney Injury," J Am Soc Nephrol 22: 2057-2067.

Akoum, A. et al. (2007). "Imbalance in the expression of the activating type I and the inhibitory type II interleukin 1 receptors in endometriosis," Human Reproduction 22(5): 1464-1473.

Allhorn, S. et al. (2008). "TLR3 and TLR4 expression in healthy and diseased human endometrium," Reproductive Biology and Endocrinology 6:40.

Ashimori, A. et al. (1990). "Novel 1,4-Dihydropyridine Calcium Antagonists.," Chem. Pharm. Bul.. 38(9): 2446-2458.

Ballak, D.B. et al. (2015). "IL-1 family members in the pathogenesis and treatment of metabolic disease: Focus on adipose tissue inflammation and insulin resistance," Cytokine 75: 280-290.

Banker, G.S. et al. (1996). "Modern Pharmaceutics, 3ed.," Marcel Dekker, New York, pp. 451 and 596.

Bauer, E. M. et al. (2012). "High Mobility Group Box 1 Contributes to the Pathogenesis of Experimental Pulmonary Hypertension via Activation of Toll-like Receptor 4," Molecular Medicine 18: 1509-1518.

Benias, P.C. et al. (2012). "Hepatic expression of toll-like receptors 3, 4, and 9 in primary biliary cirrhosis and chronic hepatitis C," Clinics and Research in Hepatology and Gastroenterology 36: 448-454.

Bijani, F.M. et al. (2012). "Toll-like Receptor Signaling Pathways in Cardiovascular Diseases: Challenges and Opportunities," International Review of Immunology 31(5): 379-395.

Bomfim, G.F. et al. (Feb. 1, 2015). "Toll-like receptor 4 inhibition reduces vascular inflammation in spontaneously hypertensive rats," Life Sci. 122: 1-7.

Bomfim, G.F. et al. (Jun. 2012). "Toll like receptor 4 contributes to blood pressure regulation and vascular contraction in spontaneously hypertensive rat," Clin Sci (Lond) 122(11): 535-543.

Brenner, M. et al. (2009). "Targeted treatment of pyoderma gangrenosum in PAPA (pyogenic arthritis, pyoderma gangrenosum and acne) syndrome with the recombinant human interleukin-1 receptor antagonist anakinra," British Journal of Dermatology 161: 1199-1201.

Brough, D. et al. (Oct. 2011). "Regulation of interleukin-1 in acute brain injury," Trends in Pharmacological Sciences 32(10): 617-622.

Buckley, G.M. et al. (2008). "IRAK-4 inhibitors. Part II: A structure-based assessment of imidazo[1,2-α]pyridine binding," Bioorganic & Medicinal Chemistry Letters 18: 3291-3295.

Bunting, M.M. et al. (2013). "Interleukin-33 Drives Activation of Alveolar Macrophages and Airway Inflammation in a Mouse Model of Acute Exacerbation of Chronic Asthma," BioMed Research International 10 pages.

Byers, D.E. et al. (2013). "Long-term IL-33-producing epithelial progenitor cells in chronic obstructive lung disease," The Journal of Clinical Investigation 123(9): 3967-3982.

Béraud, D. et al. (2012). "Misfolded α-synuclein and toll-like receptors: therapeutic targets for Parkinson's disease," 18S1: S17-S20.

Cameron, B. et al. (Oct. 24, 2012). "Loss of Interleukin Receptor-Associated Kinase 4 Signaling Suppresses Amyloid Pathology and Alters Microglial Phenotype in a Mouse Model of Alzheimer's Disease," The Journal of Neuroscience 32(43): 15112-15123.

Candia, L. et al. (2007). "Toll-like receptor-2 expression is upregulated in antigen-presenting cells from patients with psoriatic arthritis: a pathogenic role for innate immunity," J. Rheumatol 34: 374-379.

Cario, E. (2010). "Toll-like Receptors in Inflammatory Bowel Diseases: A Decade Later," Inflamm Bowel Dis 16(9): 1583-1597.

Carrasco, S. et al. (2011). "Toll-like reception (TLR) 2 is upregulated on peripheral blook monocytes of patients with psoriatic arthritis: a role for a gram-positive inflammatory trigger," Clinical and Experimental Rheumatology 29: 958-962.

Carty, M. et al. (2011). "Evaluating the role of Toll-like receptors in diseases of the central nervous system," Biochemical Pharmacology 81: 825-837.

Caso, F. et al. (2014). "Biological Treatments in Behçet's Disease: Beyond Anti-TNF Therapy," Mediators of Inflammation Article ID 107421, 14 pages.

Ceccarelli, S. et al. (Nov. 28, 2014). "Toll-like receptor-mediated signaling cascade as a regulator of the inflammation network during alcoholic liver disease," World J Gastroenterol 20(44): 16443-16451.

Cevikbas, F. et al. (2012). "IL-33: A Novel Danger Signal System in Atopic Dermatitis," Journal of Investigative Dermatology 132: 1326-1329.

Chang, J.H. et al. (2012). "Recent advances in Toll-like receptors and anterior uveitis," Clinical and Experimental Ophthalmology 40: 821-828.

Chen, D-Y. et al. (2013). "Involvement of TLR7 MyD88-dependent signaling pathway in the pathogenesis of adult-onset Still's disease," Arthritis Research & Therapy 15: 1-12.

Chen, X. (2015). "Significance of TLR4/MyD88 expression in breast cancer," Int J Clin Exp Pathol 8(6): 7034-7039.

Chiang, E.Y. et al. (2011). "Immune Complex-Mediated Cell Activation from Systemic Lupus Erythematosus and Rheumatoid Arthritis Patients Elaborate Different Requirement for IRAK1/4 Kinase Activity across Human Cell Types," J Immunol 186: 1279-1288.

(56) References Cited

OTHER PUBLICATIONS

Choi, J-W. et al. (2013). "MYD88 expression and L265P mutation in diffuse large B-cell lymphoma," Human Pathology 44: 1375-1381.

Chopra, P. et al. (2013). "Treatment of Complex Regional Pain Syndrome (CRPS) Using Low Dose Naltrexone (LDN)," J Neuroimmune Pharmacol 8: 470-476.

Christensen, S.R. et al. (2006). "Toll-like Receptor 7 and TLR9 Dictate Autoantibody Specificity and Have Opposing Inflammatory and Regulatory Roles in a Murine Model of Lupus," Immunity 25: 417-428.

Christia, P. et al. (Sep. 2013). "Targeting inflammatory pathways in myocardial infarction," Eur J Clin Invest 43(9): 986-995.

Ciccia, F. et al. (2015). "Difference in the expression of IL-9 and IL-17 correlates with different histological pattern of vascular wall injury in gian cell arteritis," Rheumatology 54: 1596-1604.

Cordiglieri, C. et al. (2014). "Innate immunity in myasthenia gravis thymus: Pathogenic effects of Toll-like receptor 4 signaling on autoimmunity," Journal of Autoimmunity 52: 74-89.

Cottet, F. et al. (2002). "Trifluoromethyl-Substituted Pyridines Through Displacement of Iodine by in situ Generated (Trifluoromethyle)copper," Eur. J. Org. Chem. 2: 327-330.

Cottet, F. et al. (2003). "Recommendable Routes to Trifluoromethyl-Substituted Pyridine- and Quinolinecarboxylic Acids," Eur. J. Org. Chem. 8: 1559-1568.

Cottet, F. et al. (2004). "Logistic flexibility in the preparation of isomeric halopyridinecarboxylic acids," Tetrahedron 60: 11869-11874.

Cottet, F. et al. (2004). "Further Metalations and Functionalizations of Chloro-, Bromo- and Iodo(trifluoromethyl) pyridines," Synthesis 10: 1619-1624.

Couillin, I. et al. (2009). "IL-1R1/MyD88 Signaling In Critical for Elastase-Induced Lung Inflammation and Emphysema," J Immunol 183: 8195-8202.

Csak, T. et al. (Jan. 13, 2011). "Deficiency in myeloid differentiation factor-2 and toll-like receptor 4 expression attenuates nonalcoholic steatohepatitis and fibrosis in mice," Am J Physiol Gastrointest Liver Physiol 300: G433-G411.

D'Elia, E. et al. (2015). "Successful treatment of subacute constrictive pericarditis with interleukin-1β receptor antagonist (anakinra)," Rheumatol, 294-295.

Damasio (1996). "Alzheimer's Disease and Related Dementias," Cecil Textbook of Medicine, 20th Edition, vol. 2, pp. 1992-1996.

Dasu, M.R. et al. (2012). "Toll-like receptors and diabetes: a therapeutic perspective," Clinical Science 122: 203-214.

Datta, S. et al. (2004). "Toll IL-1 Receptors Differ in Their Ability to Promote the Stabilization of Adenosine and Uridine-Rich Elements Containing mRNA," J Immunol 173: 2755-2761.

David, B.T. et al. (2013). "A toll-like receptor 9 antagonist reduces pain hypersensitivity and the inflammatory response in spinal cord injury," Neurobiology of Disease 54: 194-205.

Davidson, D.J. et al. (2006). "IRAK-4 Mutation (Q293X): Rapid Detection and Characterization of Defective Post-Transcriptional TLR/IL-1R Responses in Human Myeloid and Non-Myeloid Cells," J. Immunol 177: 8202-8211.

Davies, R.R. (1955). "Indazole Derivatives: The Synthesis of Various Amino- and Hydroxy-indazoles and Derived Sulphonic Acids," Journal of the Chemical Society, 2412-2419.

De Koning, H.D. (2014). "Schnitzler's syndrome: lessons from 281 cases," Clinical and Translational Allergy 4(41): 1-15.

Del Rey, A. et al. (2012). "Chronic neuropathic pain-like behavior and brain-borne IL-1β," Ann. N.Y. Acad. Sci. 1262: 101-107.

Denes, A. et al. (2013). "Central and haematopoietic interleukin-1 both contribute to ischaemic brain injury in mice," Disease Models & Mechanisms 6: 1043-1048.

Deng et al. (2013). "Toll-Like receptor 4 mediates acute lung injury induced by high mobility group box-1" PLOS One 8:e64375, 1-8.

Deng, J. et al. (Feb. 27, 2009). "TLR4 and TLR5 induce distinct types of vasculitis," Circ Res. 104(4): 488-495.

Devaraj, S. et al. (Aug. 31, 2011). "Knockout of Toll-like Receptor-2 attenuates both the Pro-Inflammatory State of Diabetes and Incipient Diabetic Nephropathy," Arterioscler Thromb Vasc Biol. 31(8): 1796-1804.

Dinarello, C.A. (2009). "Immunological and Inflammatory Functions of the Interleukin-1 Family," Annu. Rev. Immunol. 27:519-550.

Dinarello, C.A. (2011). "A clinical perspective of IL-1β as the gatekeeper of inflammation," Eur. J. Immunol. 41: 1203-1217.

Dispenza, M.C. et al. (2012). "Systemic isotretinoin therapy normalizes exaggerated TLF-2-mediated innate immune responses in acne patients," J. Invest Dermatol. 132(9): 2198-2205.

Dubaniewicz, A. (2013). "Microbial and human heat shock proteins as 'danger signals' in sarcoidosis," Human Immunology 74; 1550-1558.

El-Faham, A. et al. (2011). ,"Peptide-Coupling Reagents" Chapter 12 in Amino Acids, Peptides and Proteins in Organic Chemistry, vol. 3—Building Blocks, Catalysis and Coupling Chemistry, Hughes, A.B. ed., Wiley, pp. 407-444.

Falck-Hansen, M. et al. (2013). "Toll-Like Receptors in Atherosclerosis," Int. J. Mol. Sci. 14: 14008-14023.

Fang, Y. et al. (2011). "Toll-like receptor and its roles in myocardial ischemic/reperfusion injury," Med Sci Monit 17(4): RA100-109.

Flannery, S. et al. (2010). "The interleukin-1 receptor-associated kinases: Critical regulators of innate immune signalling," Biochemical Pharmacology 80:1981-1991.

Foster, A.M. et al. (2014). "IL-36 promotes myeloid cell infiltration, activation and inflammatory activity in skin," J Immunol. 192(12): 6053-6061.

Frangogiannis, N.G. (May 2015). "Inflammation in cardiac injury, repair and regeneration," Curr Opin Cardiol 30(3): 240-245.

Freeman, C.M. et al. (2013). "Lung CD8+ T cells in COPD have increased expression of bacterial TLRs," Respiratory Research 14: 13.

Fresno, M. et al. (2011). "Toll-like receptors, inflammation, metabolism and obesity," Archives of Physiology and Biochemistry 117(3): 151-164.

Gadakh, A.V. et al. (2012). "Heteroaryl Hydroxycarbonylation: An efficient, robust, practically scalable approach using formyl acetate as the co source," Synthetic Communications 42: 658-666.

Gambuzza, M. et al. (2011). "Targeting Toll-like receptors: Emerging therapeutics from multiple sclerosis management," Journal of Neuroimmunology 239: 1-12.

Gerdes, H. et al. (1980). "3-Oxatricyclo[5.3.1.01,4]undec-4-en, ein stark gespannter Vierring-Enolether," 3. Chemische Berichte 113: 1907-1920. (Abstract Only).

Gilliet, M. et al. (2004). "Psoriasis Triggered by Toll-like Receptor 7 Agonist Imiquimod in the Presence of Dermal Plasmacytoid Dendritic Cell Precursors," Arch Dermatol 140: 1490-1495.

Goh, F.G. et al. (2012). "Intrinsic danger: activation of Toll-like receptors in rheumatoid arthritis," Rheumatology 51: 7-23.

Gresnigt, M.S. et al. (2013). "Biology of IL-36 cytokines and their role in disease," Seminars in Immunology 25: 458-465.

Guerrero, A.T.G. et al. (2012). "Toll-like receptor 2/MyD88 signaling mediates zymosan-induced joint hypernociception in mice: Participation of TNF-α, IL-1β and CXCL1/KC," European Journal of Pharmacology 674: 51-57.

Guo, H. et al. (2012). "Toll-like receptor 2 siRNA suppresses corneal inflammation and attenuates Aspergillus fumigatus keratitis in rats," Immunology and Cell Biology 90: 352-357.

Gura, T. (1997). "Systems for Identifying New Drugs Are Often Faulty," Science 278(5340): 1041-1042, , 5 pages.

Gül, A. et al. (2012). "Interleukin-1β-regulating antibody XOMA 052 (gevokizumab) in the treatment of acute exacerbations of resistant uveitis of Behçet's disease: an open-label pilot study," Ann Rheum Dis 71:563-566.

Haenuki, Y. et al. (2012). "A critical role of IL-33 in experimental allergic rhinitis," J Allergy Clin Immunol 130(1): 184-194.

Han, P. et al. (2013). "Interleukin-33 Mediates Formalin-Induced inflammatory pain in mice," Neuroscience 241: 59-66.

Hao, L-Y. et al. (2013). "Inflammasomes in inflammatory bowel disease pathogenesis," Current Opinion 29(4): 363-369.

(56) References Cited

OTHER PUBLICATIONS

Heimesaat, M.M. et al. (2007). "Shift Towards Pro-inflammatory Intestinal Bacteria Aggravates Acute Murine Colitis via Toll-like Receptors 2 and 4," PLoS ONE 7: 1-7.
Heimesaat, M.M. et al. (2010). "MyD88/TLR9 mediated immunopathology and gut microbiota dynamics in a novel murine model of intestinal graft-versus-host disease," Gut 59: 1079-1087.
Henderson, C. et al. (2010). "Monogenic IL-1 Mediated Autoinflammatory and Immunodeficiency Syndromes: Finding the Right Balance in Response to Danger Signals," Clin Immunol. 135(2): 210-222.
Hiernanz, R. et al. (2015). "Toll-like receptor 4 contributes to vascular remodeling and endothelial dysfunction in angiotensin II-induced hypertension," British Journal of Pharmacology 172: 3159-3176.
Hilberath, J.N. et al. (Aug. 2017). "Resolution of Toll-like receptor 4-mediated acute lung injury is linked to eicosanoids and suppressor of cytokine signaling 3," The FASEB Journal 25(6): 1827-1835.
Hoffmann, R. (Dec. 1999). "The Potential Role of Cytokines and T Cells in Alopecia Areata," Journal of Investigative Dermatology Symposium Proceedings 4(3): 235-238.
Holle, J.U. et al. (2013). "Toll-like receptor TLR2 and TLR9 ligation triggers neutrophil activation in granulomatosis with polyangiitis," Rheumatology 52: 1183-1189.
Holtmann, H. et al. (2001). "The MAPK Kinase Kinase TAK1 Plays a Central Role in Coupling the Interleukin-1 Receptor to Both Transcriptional and RNA-targeted Mechanisms of Gene Regulation," The Journal of Biological Chemistry 276(5): 3508-3516.
Imaoka, H. et al. (2008). "Interleukin-18 production and pulmonary function in COPD," Eur Respir J. 31: 287-297.
International Search Report dated Jan. 28, 2016 for PCT/EP2015/077596 filed Nov. 25, 2015, 9 pages.
Jain, S. et al. (2015). "Effectiveness and Safety of Anakinra for Management of Refractory Pericarditis," The American Journal of Cardiology 116: 1277-1279.
Janeway, C.A. et al. (2002). "Innate Immune Recognition," Annu. Rev. Immunol. 20:197-216.
Jeurissen et al. (1992). "Histological and functional differentiation of non-lymphoid cells in the chicken spleen" Immunol. 77: 75-80.
Jeyaseelan, S. et al. (Mar. 2005). "Distinct Roles of Pattern Recognition Receptors CD14 and Toll-Like Receptor 4 in Acute Lung Injury," Infection and Immunity 73(3): 1754-1763.
Jialal, I. et al. (2014). "Global toll-like receptor 4 knockout results in decreased renal inflammation, fibrosis and podocytophathy," Journal of Diabetes and Its Complications 28: 755-761.
Johnson, J. et al. (2001). "Relationships between drug activity in NCI preclinical in vitro and in vivo models and early clinical trials," British Journal of Cancer 84(10): 1424-1431.
Kaarniranta, K. et al. (2009). "Age-related macular degeneration: activation of innate immunity system via pattern recognition receptors," J Mol Med 87: 117-123.
Kamari, Y. et al. (Nov. 2011). Lack of Interleukin-1α or Interleukin-1β Inhibits Transformation of Steatosis to Steatohepatitis Liver Fibrosis in Hypercholesteroleic Mice, J Hepatol 55(5): 1086-1094.
Kang, M-J. et al. (2007). "IL-18 is Inducted and IL-18 Receptor α Plays a Critical Role in the Pathogenesis of Cigarette Smoke-Induced Pulmonary Emphysema and Inflammation," J Immunol 178: 1948-1959.
Kaplan, M. et al. (2014). "Effectiveness of interleukin-1 receptor antagonist (Anakinra) on cerulean-induced experimental acute pancreatitis in rats," Scandinavian Journal of Gastroenterology 49: 1124-1130.
Kawayama, T. et al. (2012). "Interleukin-18 in Pulmonary Inflammatory Diseases," Journal of Interferon & Cytokine Research 32(10): 443-451.
Kezic, J. et al. (2011). "Endotoxin-induced uveitis is primarily dependent on radiation-resistant cells and on MyD88 but not TRIF," Journal of Leukocyte Biology 90(2): 305-311.
Kfoury, A. et al. (2013). "MyD88 in DNA Repair and Cancer Cell Resistance to Genotoxic Drugs," J Natl Cancer Inst 105: 937-946.
Khan, K.N. et al. (Aug. 2013). "Toll-like receptor system and endometriosis," J. Obstet. Gynaecol. Res., 39(8): 1281-1292.
Kim, T.W. et al. (Jan. 2011). "The Critical Role of IL-1 Receptor-Associated Kinase 4-Mediated NF-kB Activation in Modified Low-Density Lipoprotein-Induced Inflammatory Gene Expression and Atherosclerosis," J Immunol 186: 2871-2880.
Kim, D. et al. (2009). "Toll-Like Receptors in Peripheral Nerve Injury and Neuropathic Pain," Current Topics in Microbiology and Immunology 336: 169-186.
Kim, G-T et al. (2010). "Expression of TLR2, TLR4, and TLR9 in dermatomyositis and polymyositis," Clin Rheumatol 29: 273-279.
Kim, K.H. et al. (2012). "Expression and significance of the TLR4/MyD88 signaling pathway in ovarian epithelial cancers," World Journal of Surgical Oncology 10: 193.
Kim, T.W. et al. (2007). "A critical role for IRAK4 kinase activity in Toll-like receptor-mediated innate immunity," JEM 204(5):1025-1036.
Kitazawa, M. et al. (Nov. 2011). "Blocking IL-1 Signaling Rescues Cognition, Attenuates Tau Pathology, and Restores Neuronal β-Catenin Pathway Function in an Alzheimer's Disease Model," J Immunol 187: 6539-6549.
Kobori, A. et al. (2010). "Interleukin-33 expression is specifically enhanced in inflamed mucosa of ulcerative colitis," J. Gastroenterol 45: 999-1007.
Kollewe, C. et al. (2004). "Sequential Autophosphorylation Steps in the Interleukin-1 Receptor-associated Kinase-1 Regulate its Availability as an Adapter in Interleukin-1 Signaling," The Journal of Biological Chemistry 279(7): 5227-5236.
Kovach, M.A. et al. (2011). "Toll like receptors in diseases of lung," International Immunopharmacology 11: 1399-1406.
Kreisel, D. et al. (2013). "Innate immunity and organ transplantation: focus on lung transplantation," Transpl Int. 26(1): 2-10.
Ku, C. et al. (2007). "Selective predisposition to bacterial infections in IRAK-4-deficient children: IRAK-4-dependent TLRs are otherwise redundant in protective immunity," JEM 204(10):2407-2422.
Kwok, Y.H. et al. (2012). "Increased Responsiveness of Peripheral Blood Mononuclear Cells to In Vitro TLF 2, 4 and 7 Ligand Stimulation in Chronic Pain Patients," PLOS One 7(8): 1-8.
LAYZER (1996). "Degenerative Diseases of the Nervous System," Cecil Textbook of Medicine, 20th Edition, vol. 2, pp. 2050-2057.
Lee et al. (2015). "Absence of toll-like receptor 4 (TLR4) extends survival in the hSOD1 G93A mouse model of amyotrophic lateral sclerosis," Journal of Neuroinflammation 12: 90.
Lee, H.S. et al. (2012). "Expression of Toll-like receptor 4 Contributes to Corneal Inflammation in Experimental Dry Eye Disease," Invest Ophthalmol Vis Sci. 53(9): 5632-5640.
Leventhal, J.S. et al. (2012). "Toll-like receptors in transplantation: sensing and reacting to injury," Kidney International 81: 826-832.
Li, D. et al. (2014). "IL-33 promotes ST2-dependent lung fibrosis by the induction of alternatively activated macrophages and innate lymphoid cells in mice," J. Allergy Clin Immunol 134(6): 1422-1432.e11.
Li, J. et al. (2013). "Toll-like receptors as therapeutic targets for autoimmune connective tissue diseases," Pharmacology & Therapeutics 138: 441-451.
Li, X. (2015). "Protective effect of neutralizing anti-IL-18α monoclonal antibody on a mouse model of acute graft-versus-host disease," Oncology Reports 34: 2031-2039.
Liang, B. et al. (2013). "Myeloid Differentiation Factor 88 Promotes Growth and Metastasis of Human Hepatocellular Carcinoma," Clin Cancer Res 19(11): 2905-2916.
Lim, J-E et al. (Sep. 2011). "MyD88 Deficiency Ameliorates β-Amyloidosis in an Animal Model of Alzheimer's Disease," The American Journal of Pathology 179(3): 1095-1103.
Liu et al. (2014). "Severe influenza A(H1N1)pdm09 infection induces thymic atrophy through activating innate CD8+CD44hi T cells by upregulating IFN-γ" Cell Death Dis. 5:e1440, 1-12.
Liu, T. et al. (2013). "New insights into the mechanisms of itch: are pain and itch controlled by distinct mechanisms?" Pflugers Arch. 465(12): 1-24.
Liu, Y et al. (2015). "Toll-like receptor 5 deficiency attenuates interstitial cardiac fibrosis and dysfunction induced by pressure

(56) References Cited

OTHER PUBLICATIONS overload by inhibiting inflammation and the endothelial-mesenchymal transition," Biochimica et Biophsica Acta 1852: 2456-2466.

Liu-Bryan, R. et al. (2005). "Innate Immunity Conferred by Toll-like Receptors 2 and 4 and Myeloid Differentiation Factor 88 Expression Is Pivotal to Monosodium Urate Monohydrate Crystal-Induced Inflammation," Arthritis & Rheumatism 52(9): 2936-2946.

Lloyd, C.M. et al. (2010). "IL-33 family members and asthma—bridging innate and adaptive immune responses," Curr Opin Immunol 22(6): 800-806.

Lugrin, J. et al. (2015). "Cutting Edge: IL-1α Is a Crucial Danger Signal Triggering Acute Myocardial Inflammation during Myocardial Infarction," The Journal of Immunology 194: 499-503.

Maekawa, Y. et al. (2009). "Survival and Cardiac Remodeling After Myocardial Infarction Are Critically Dependent on the Host Innate Immune Interleukin-1 Receptor-Associated Kinase-4 Signaling," Circulation 120: 1401-1414.

Malkov, A.V. et al. (2003). "A long-range chiral relay via tertiary amide group in asymmetric catalysis: new amino acid-derived N,P-ligands for copper-catalyzed conjugate addition," Chem Commun, 1948-1949.

Margaritopoulos, G.A. et al. (2010). "Investigation of Toll-like receptors in the pathogenesis of fibrotic and granulomatous disorders: a bronchoalveolar lavage study," Fibrogenesis & Tissue Repair 3: 20.

Martínez-González, I. et al. (2013). "Human Mesenchymal Stem Cells Overexpressing the IL-33 Antagonist Soluble IL-1 Receptor-Like-1 Attenuate Endotoxin-Induced Acute Lung Injury," Am J Respir Cell Mol Biol 49(4): 552-562.

Mcgettrick, A.F. et al. (2007). "Toll-like receptors: key activators of leucocytes and regulator of haematopoiesis," British Journal of Haematology 139: 185-193.

Miller (2004). "Toll-like receptors in skin" Adv. Dermatol. 24: 71-87.

Min, W. et al. (2015). "Baicalin Protects Keratinocytes from Toll-like Receptor-4 Mediated DNA Damage and Inflammation Following Ultraviolet Irradiation," Photochemistry and Photobiology, 91: 1435-1443.

Minkis, K. et al. (2012). "Interleukin 1 Receptor Antagonist Deficiency Presenting as Infantile Pustulosis Mimicking Infantile Pustular Psoriasis," Arch Dermatol. 148(6): 747-752.

Miura, K. et al. (2010). "Toll-Like Receptor 9 Promotes Steatohepatitis by induction of Interleukin-1β in Mice," Gastroenterology 139: 323-334.

Miura, K. et al. (Jun. 21, 2014). "Role of gut microbiota and Toll-like receptors in nonalcoholic fatty liver disease," World J Gastroenterology 20(23): 7381-7391.

Moco, S. et al. (2007). "Metabolomics technologies and metabolite identification," Trends in Analytical Chemistry, 26(9): 855-866.

Morytko, M. et al. (2008). "Synthesis and in vitro activity of N1-cyano-4-(2-phenylacetyl)-N-o-tolylpiperzaine-1-carboximidamide P2X7 antagonists," Bioorganic & Medicinal Chemistry Letters 18: 2093-2096.

Motshwene, P.G. et al. (2009). "An Oligomeric Signaling Platform Formed by the Toll-like Receptor Signal Transducers MyD88 and IRAK-4," The Journal of Biological Chemistry 284(37):25404-25411.

Márquez, A. et al. (2014). "Influence of the IL17A locus in giant cell arteritis susceptibility," Ann Rheum Dis 73: 1742-1745.

Nadigel, J. et al. (2011). "Cigarette smoke increases TLR4 and TLR9 expression and induces cytokine production from CD8+ T cells in chronic obstructive pulmonary disease," Respiratory Research 12: 149.

Nakanishi et al. (2013). "IL-33, but not IL-25, is crucial for the development of house dust mite antigen-induced allergic rhinitis," PLOS One 8: e78099, 1-8.

Narayanan, S. et al. (2008). "Interleukin-1 Receptor-1-deficient Mice Show Attenuated Production of Ocular Surface Inflammatory Cytokines in Experimental Dry Eye," Cornea 27(7): 811-817.

Ngo, V.N. et al. (Feb. 3, 2011). "Oncogenically active MYD88 mutations in human lymphoma," Nature 470: 115-119.

Nickerson, K.M. et al. (2010). "TLR9 Regulates TLR7- and MyD88-Dependent Autoantibody Production and Disease in a Murine Model of Lupus," J Immunol 184: 1840-1848.

Nicotra, L. et al. (2012). "Toll-Like Receptors in Chronic Pain," Exp Neurol. 234(2): 316-329.

Niebuhr, M. et al. (2008). "Dysregulation of toll-like receptor-2 (TLR-2)-induced effects in monocytes from patients with atopic dermatitis: impact of the TLR-2 R753Q polymorphism," Allergy 63: 728-734.

Noelker, C. et al. (2013). "Toll like receptor 4 mediates cell death in a mouse MPTP model of Parkinson disease," Scientific Reports 3: 1393.

Nordström, D. et al. (2012). "Beneficial Effect of Interleukin 1 Inhibition with Anakinra in Adult-onset Still's Disease. An Open, Randomized, Multicenter Study," The Journal of Rheumatology 39(10): 2008-2011.

Nozaki, Y. et al. (2004). "Polymorphisms of Interleukin-1β and β3-Adrenergic Receptor in Japanese Patients With Nonalcoholic Steatohepatitis," Alcohol Clin Exp Res. 28(8): 106S-110S.

O'Jara, F. et al. (2013). "Radical-Based Regioselective C—H Functionalization of Electron-Deficient Heteroarenes: Scope, Tunability, and Predictability," J Am Chem Soc. 135(32): 12122-12134.

Ochi, A. et al. (2012). "MyD88 inhibition amplifies dendritic cell capacity to promote pancreatic carcinogenesis via Th2 cells," J. Exp. Med. 209(9): 1671-1687.

Okiyama, N. et al.(Nov. 2012). "T Lymphocytes and Muscle Condition Act Like Seeds and Soil in a Murine Polymyositis Model," Arthritis & Rheumatism 64(11): 3741-3749.

Ouziel, R. et al. (Jun. 2012). "The ST2 Pathway Is Involved in Acute Pancreatitis," The American Journal of Pathology 180(6): 2330-2339.

Oyama, J. et al. (2004). "Reduced Myocardial Ischemia-Reperfusion Injury in Toll-Like Receptor 4-Deficient Mice," Circulation 109: 784-789.

Park, H.J. et al. (Jan. 2014). "Toll-like receptor signaling regulates cisplatin-induced mechanical allodynia in mice," Cancer Chemother Pharmacol. 73(1): 25-34.

Pauwels, N.S. et al. (2011). "Role of IL-1α and the Nlrp3/caspase-1/IL-1β axis in cigarette smoke-induced pulmonary inflammation and COPD," European Respiratory Journal 38(5): 1019-1028.

Pearce, H. et al. (2008). "Failure Modes in Anticancer Drug Discovery and Development," Cancer Drug Design and Discovery, ed. Stephen Neidle, Chapter 18, 424-435.

Pettersson, T. et al. (2012). "Setting up TRAPS," Annals of Medicine 44: 109-118.

Piggott, D.A. et al. (Feb. 2005). "MyD88-dependent induction of allergic Th2 responses to intranasal antigen," The Journal of Clinical Investigation 115(2): 459-467.

Puente, X.S. et al. (Jul. 7, 2011). "Whole-genome sequencing identifies recurrent mutations in chronic lymphocytic leukaemia," Nature 475: 101.

Qi, Y. et al. (2014). "Retinal Ischemia/Reperfusion Injury Is Mediated by Toll-like Receptor 4 Activation of NLRP3 Inflammasomes," Invest Ophthalmol Vis Sci 55:5466-5475.

Qiu, C. et al. (2013). "Anti-interleukin-33 inhibits cigarette smoke-induced lung inflammation in mice," Immunology 138: 76-82.

Rakoff-Nahoum, S. et al. (2006). "Role of Toll-like Receptors in Spontaneous Commensal-Dependent Colitis," Immunity 25: 319-329.

Ramirez Cruz, N.E et al. (2004). "Toll-like receptors: dysregulation in vivo in patients with acute respiratory distress syndrome," Revista Alergia Mexico 51(6): 210-217.

Ramirez, S.R. et al. (2012). "Toll-like Receptors and Diabetes Complications: Recent Advances," Current Diabetes Reviews 8: 480-488.

Redfern, R. L. et al. (2010). "Toll-like receptors in ocular surface disease," Experimental Eye Research 90: 679-687.

Rekhter, M. et al. (2008). "Genetic ablation of IRAK4 kinase activity inhibits vascular lesion formation," Biochemical and Biophysical Research Communications 367: 642-648.

(56) References Cited

OTHER PUBLICATIONS

Roger, T. et al. (Feb. 17, 2009). "Protection from lethal Gram-negative bacterial sepsis by targeting Toll-like receptor 4," PNAS 106(7): 2348-2352.
Roh, Y-S. et al. (2013). "Toll-like Receptors in Alcoholic Liver Disease, Non-Alcoholic Steatohepatitis and Carcinogenesis," J Gastroenterol Hepatol. 28(01): 38-42.
Ruperto, N. et al. (2012). "Two Randomized Trials of Canakinumab in Systemic Juvenile Idiopathic Arthritis," The New England Journal of Medicine 367(25): 2396-2406.
Ryu, H.C. et al. (2014). "2-Alkyl/alkeyl substituted pyridine C-region analogues of 2-(3-fluoro-4-methylsulfonylaminophenyl)propanamides as highly potent TRPV1 antagonists," Bioorganic & Medicinal Chemistry Letters 24:4039-4043.
Saluja, R. et al. (2015). "The role of the IL-33/IL-1RL1 axis in mast cell and basophil activation in allergic disorders," Molecular Immunology 63: 80-85.
Santulli et al. (2012). "Serum and peritoneal interleukin-33 levels are elevated in deeply infiltrating endometriosis," Hum. Reprod. 27: 2001-2009.
Scanzello, C.R. et al. (2008). "Innate immune system activation in osteoarthritis: is osteoarthritis a chronic wound?" Current Opinion in Rheumatology 20: 565-572.
Schlosser, M. et al. (2003). "The Direct Metalation and Subsequent Functionalization of Trifluoromethyl-Substituted Pyridines and Quinolines," Eur. J. Org. Chem., 1569-1575.
Schmidt, E. et al. (1996). "Detection of IL-1α, IL-1β and IL-1 receptor antagonist in blister fluid of bullous pemphigoid," Journal of Dermatological Science 11: 142-147.
Schmidt, M. et al. (Sep. 2010). "Crucial role for human Toll-like receptor 4 in the development of contact allergy to nickel," Nature Immunology 11(9): 814-820.
Schrepf, A. et al. (Oct. 2015). "Toll-like Receptor 4 and Comorbid Pain in Interstitial Cystitis/Bladder Pain Syndrome: A Multidisciplinary Approach to the Study of Chronic Pelvic Pain Research Network Study," Brain Behav Immun. 49: 66-74.
Sedimbi, S.K. et al. (2013). "IL-18 in inflammatory and autoimmune disease," Cell. Mol. Life Sci. 70: 4795-4802.
Seganish (2016). "Inhibitors of interleukin-1 receptor-associated kinase 4 (IRAK4): a patent review (2012-2015)," Expert Opinion on Therapeutic Patents, 26(8): 917-932.
Seki, H. et al. (2010). "effect of Toll-like receptor 4 inhibitor on LPS-induced lung injury," Inflamm. Res. 59: 837-845.
Selway, J.L. et al. (2013). "Toll-like receptor 2 activation and comedogenesis: implications for the pathogenesis of acne," BMC Dermatology 13(10): 1-7.
Seneviratne, A.N. et al. (2012). "Toll-like receptors and macrophage activation in atherosclerosis," Clinica Chimica Acta 413: 3-14.
Shi, Y. et al. (2010). "Monosodium urate crystals in inflammation and immunity," Immunological Reviews 233: 203-217.
Shimizu, M. et al. (2006). "Synthesis and biological activities of new 1α,25-dihydroxy-19-norvitamin D3 analogs with modifications in both the A-ring and the side chain," Bioorganic & Medicinal Chemistry 14: 4277-4294.
Sikora, J. et al. (2012). "Imbalance in Cytokines from interleukin-1 Family—Role in Pathogenesis of Endometriosis," 68: 138-145.
Simone, J.V. et al. (1996). "Oncology," Part XIV in Cecil Textbook of Medicine, 20th edition, Bennet, J.C. et al. eds., W.B. Saunders Company, pp. 1004-1010.
Srivastava, R. et al. (2012). "Augmentation of Therapeutic Responses in Melanoma by Inhibition of IRAK-1, -4," Cancer Research 72(23): 6209-6216.
Staschke, K.A. et al. (2009). "IRAK4 kinase Activity is Required for Th17 Differentiation and Th17-mediated Disease," J Immunol 183(1): 568-577.
Stojsavljevic, S. et al. (Dec. 28, 2014). "Adipokines and proinflammatory cytokines, the key mediators in the pathogenesis of nonalcoholic fatty liver disease," World Journal of Gastroenterology 20(48): 18070-18091.
Stokes, J.A. (2013). "Toll-like receptor signaling adapter proteins govern spread of neuropathic pain and recovery following nerve injury in male mice," Journal of Neuroinflammation 10(148): 1-14.
Sun, M. et al. (2014). "The Role of Interleukin-1 Receptor-Associated Kinases in Vogt-Koyanagi-Herada Disease," PLOS ONE 9(4): 1-8.
Sun, Y. et al. (2009). "Inhibition of Corneal Inflammation by the TLR4 Antagonist Eritoran Tetrasodium (E5564)," Invest Ophthalmol Vis Sci. 50(3): 1247-1254.
Suzuki, N. et al. (2002). "Severe impairment of interleukin-1 and Toll-like receptor signaling in mice lacking IRAK-4," Nature 416: 750-754.
Swamy, K.C.K. et al.(2009). "Mitsunobu and Related Reactions: Advances and Applications," Chem. Rev. 109: 2551-2651.
Szczepanski, M.J. et al. (Apr. 1, 2009). "Triggering of Toll-like Receptor 4 Expressed on Human head and Neck Squamous Cell Carcinoma Promotes Tumor Development and Protects the Tumor from immune Attack," Cancer Res 69(7): 3105-3113.
Talabot-Ayer, D. et al. (2014). "Immune-mediated experimental arthritis in IL-33 deficient mice," Cytokine 69: 68-74.
Terhorst, D. et al. (2010). "The Role of Toll-Like Receptors in Host Defenses and Their Relevance to Dermatologic Disease," Am J. Clin Dermatol 11(1): 1-10.
Thompson, J. A. et al. (2013). "Potential role of Toll-like receptors in programming of vascular dysfunction," Clinical Science 125: 19-25.
Timmers, L. et al. (2008). "Toll-Like Receptor 4 Mediates Maladaptive Left Ventricular Remodeling and Impairs Cardiac Function After Myocardial Infraction," Circ Res. 102: 257-264.
Timper, K. et al. (2015). "Safety, pharmacokinetics, and preliminary efficacy of a specific anti-IL-1alpha therapeutic antibody (MABp1) in patients with type 2 diabetes mellitus," Journal of Diabetes and Its Complications 29: 955-960.
Treon, S.P. et al. (Aug. 30, 2012). "MYD88 L265P Somatic Mutation in Waldernstrom's Macroglobulinemia," The New England Journal of Medicine 367(9): 826-833.
U.S. Appl. No. 16/306,235, filed Nov. 30, 2018, for Beddies et al.
U.S. Appl. No. 16/428,669, filed May 31, 2019, for Bothe et al.
U.S. Appl. No. 16/863,330, filed Apr. 30, 2020, for Rausch et al.
Valaperti, A. et al. (2013). "Innate Immune Interleukin-1 Receptor-Associated Kinase 4 Exacerbates Viral Myocarditis by Reducing CCR5+CD11b+Monocyte Migration and Impairing Interferon Production," Circulation 128: 1542-1554.
Valeur, E. et al. (2009). "Amide bond formation: beyond the myth of coupling reagents," Chem. Soc. Rev. 38: 606-631.
Van Der Watt, J.J. et al. (2014). "Plasma cytokine profiles in HIV-1 infected patients developing neuropathic symptoms shortly after commencing antiretroviral therapy: a case-control study," BMC Infectious Diseases 14: 71.
Vennegaard, M.T. et al. (2014). "Epicutaneous exposure to nickel induces nickel allergy in mice via a MyD88-dependent and interleukin-1-dependent pathway," Contact Dermatitis 71: 224-232.
Viguier, M. et al. (2010). "Successful Treatment of Generalized Pustular Psoriasis With the Interleukin-1-Receptor Antagonist Anakinra: Lack of Correlation with IL1RN Mutations," Annals of Internal Medicine 153: 66-67.
Vijmasi, T. et al. (2013). "Topical administration of interleukin-1 receptor antagonist as a therapy for aqueous-deficient dry eye in autoimmune disease," Molecular Vision 19: 1957-1965.
Volin, M.V. et al. (2011). "Interleukin-18: A Mediator of Inflammation and Angiogenesis in Rheumatoid Arthritis," Journal of Interferon & Cytokine Research 31(10): 745-781.
Walsh, D. et al. (2013). "Pattern recognition receptors—Molecular orchestrators of inflammation in inflammatory bowel disease," Cytokine & Growth Factor Reviews 24: 91-104.
Wan, Y.Y. et al. (2006). "The kinase TAK1 integrates antigen and cytokine receptor signaling for T cell development, survival and function," Nature Immunology 7(8): 851-858.
Wang, C. et al. (2001). "TAK1 is a ubiquitin-dependent kinase of MMK and IKK," Nature 412: 346-351.

(56) References Cited

OTHER PUBLICATIONS

Wang, E. et al. (2010). "High expression of Toll-like receptor 4/myeloid differentiation factor 88 signals correlates with poor prognosis in colorectal cancer," British Journal of Cancer 102: 908-915.

Wang, L. et al. (2015). "Picroside II protects rat kidney against ischemia/reperfusion-induced oxidative stress and inflammation by the TLR4/NF-κB pathway," Experimental and Therapeutic Medicine 9: 1253-1258.

Wang, Y-C. et al. (2013). "Toll-like Receptor 4 Antagonist Attenuates Intracerebral Hemorrhage-Induced Brain Injury," Stroke 44: 2545-2552.

Wolf, G. et al. (2008). "Interleukin-1 signaling in required for induction and maintenance of postoperative incisional pain: Genetic and pharmacological studies in mice," Brain, Behavior, and Immunity 22: 1072-1077.

Wolff, M.E. (1995). "Burger's Medicinal Chemistry, 5ed, Part 1," John Wiley & Sons, pp. 975-977.

Wollina, U. et al. (2013). "Acne inversa (Hidradenitis suppurativa): A review with a focus on pathogenesis and treatment," Indian Dermatology Online Journal 4(1): 1-11.

Won, K.A. et al. (Mar. 2014). "The Glial-Neuronal GRK2 Pathway Participates in the Development of Trigeminal Neuropathic Pain in Rats," The Journal of Pain 15(3): 250-261.

Wong, L. et al. (2015). "Experimental Autoimmune Prostatitis Induces Microglial Activation in the Spinal Cord," The Prostate 75: 50-59.

Written Opinion of ISA dated Jan. 28, 2016 for PCT/EP2015/077596, filed Nov. 25, 2015, 6 pages.

Xiang, M. et al. (2010). "Association of Toll-Like Receptor Signaling and Reactive Oxygen Species: A Potential Therapeutic Target for Posttrauma Acute Lung Injury," Mediators of Inflammation 2010: 916425.

Xiang, W. et al. (2015). "Role of Toll-like receptor/MYD88 signaling in neurodegenerative diseases," Rev. Neurosci. 26(4): 407-414.

Yamada, A. et al. (2017). "Targeting IL-1 in Sjögren's syndrome," Expert Opin. Ther. Targets 17(4): 393-401.

Yang, H. et al. (2005). "IL-1 Receptor Antagonist-Mediated Therapeutic Effect in Murine Myasthenia Gravis Is Associated with Suppressed Serum Proinflammatory Cytokines, C3, and Anti-Acetylcholine Receptor IgG1," The Journal of Immunology 175: 2018-2025.

Yang, L. et al. (May 2012). "Toll-like receptors in liver fibrosis: cellular crosstalk and mechanisms," Frontiers in Physiology 3(138): 1-18.

Yap, D. Y. H. et al. (2013). "The role of cytokines in the pathogenesis on systemic lupus erythematosus—from bench to bedside," Nephrology 18: 243-255.

Ye, D. et al. (2012). "Toll-like receptor-4 mediates obesity-induced non-alcoholic steatohepatitis through activation of X-box binding protein-1 in mice," Gut 61: 1058-1067.

Yin, H. et al. (2012). "Adenovirus-mediated delivery of soluble ST2 attenuates ovalbumin-induced allergic asthma in mice," Clinical & Experimental Immunology 170: 1-9.

Zambrano-Zaragoza, J.F. et al. (2014). "Th17 Cells in Autoimmune and Infectious Diseases," International Journal of Inflammation 1-12.

Zhang, Y-B. et al. (2009). "Increased expression of Toll-like receptors 4 and 9 in human lung cancer," Mol Biol Rep 36: 1475-1481.

Zhao, J. et al. (2011). "Altered biliary epithelial cell and monocyte responses to lipopolysaccharide as a TLR ligand in patients with primary biliary cirrhosis," Scandinavian Journal of Gastroenterology 46: 485-494.

Zhao, J. et al. (2013). "Spinal Interleukin-33 and its receptor ST2 contribute to bone cancer-induced pain in mice," Neuroscience 253: 172-182.

Zhao, S. et al. (Jul. 2014). "Toll-like receptors and prostate cancer," Frontiers in Immunology 5(352): 1-6.

Zhu, F-G. et al. (2013). "A novel antagonist of Toll-like receptors 7, 8 and 9 suppresses lupus disease-associated parameters in NZBW/F1 mice," Autoimmunity 46(7): 419-428.

Zong, M. (2014). "Anakinra treatment in patients with refractory inflammatory myopathies and possible predictive response biomarkers: a mechanistic study with 12 months follow-up," Ann Rheum Dis 73: 913-920.

U.S. Appl. No. 17/544,641, filed Dec. 7, 2021, for Bothe et al. (Also cited as U.S. Publication No. US20220241261).

U.S. Appl. No. 17/673,644, filed Feb. 16, 2022, for Bothe et al. (Also cited as U.S. Publication No. US20220249456).

U.S. Appl. No. 17/869,673, filed Jul. 20, 2022, for Bothe et al. (Also cited as U.S. Publication No. US20230174508).

* cited by examiner

A

SUBSTITUTED INDAZOLES, METHODS FOR THE PRODUCTION THEREOF, PHARMACEUTICAL PREPARATIONS THAT CONTAIN SAID SUBSTITUTED INDAZOLES, AND USE OF SAID SUBSTITUTED INDAZOLES TO PRODUCE DRUGS

CROSS REFERENCE TO RELATED APPLICATIONS

This application is a continuation application of U.S. patent Ser. No. 17/009,553, filed Sep. 1, 2020, which is a continuation application of U.S. patent application Ser. No. 16/377,025, filed on Apr. 5, 2019, now U.S. Pat. No. 10,793,545, which is a continuation application of U.S. patent application Ser. No. 15/529,996, which adopts the international filing date of Nov. 25, 2015, now U.S. Pat. No. 10,308,634, which is the National Phase application under 35 U.S.C. § 371 of International Application No. PCT/EP2015/077596, filed Nov. 25, 2015, which claims priority benefit to European Application No. 14195032.9, filed Nov. 26, 2014.

The present application relates to novel substituted indazoles, to processes for preparation thereof, to intermediates for use in the preparation of the novel compounds, to the use of the novel substituted indazoles for treatment and/or prophylaxis of diseases and to the use thereof for production of medicaments for treatment and/or prophylaxis of diseases, especially of proliferative disorders, of autoimmune disorders, of metabolic and inflammatory disorders, for example rheumatoid arthritis, spondyloarthritis (especially psoriatic spondyloarthritis and Bekhterev's disease), chronic obstructive pulmonary disease (abbreviation: COPD), multiple sclerosis, systemic lupus erythematosus, gout, metabolic syndrome, fatty liver hepatitis, insulin resistance, endometriosis and inflammation-induced or chronic pain, and of lymphoma.

The present invention relates to novel substituted indazoles of the general formula (I) which inhibit interleukin-1 receptor-associated kinase 4 (IRAK4).

Human IRAK4 (interleukin-1 receptor-associated kinase 4) plays a key role in the activation of the immune system. Therefore, this kinase is an important therapeutic target molecule for the development of inflammation-inhibiting substances. IRAK4 is expressed by a multitude of cells and mediates the signal transduction of Toll-like receptors (TLRs), except TLR3, and receptors of the interleukin (IL)-1β family consisting of the IL-1R (receptor), IL-18R, IL-33R and IL-36R (Janeway and Medzhitov, Annu. Rev. Immunol., 2002; Dinarello, Annu. Rev. Immunol., 2009; Flannery and Bowie, Biochemical Pharmacology, 2010).

Neither IRAK4 knockout mice nor human cells from patients lacking IRAK4 react to stimulation by TLRs (except TLR3) and the IL-1β family (Suzuki, Suzuki, et al., Nature, 2002; Davidson, Currie, et al., The Journal of Immunology, 2006; Ku, von Bernuth, et al., JEM, 2007; Kim, Staschke, et al., JEM, 2007).

The binding of the TLR ligands or the ligands of the IL-1β family to the respective receptor leads to recruitment and binding of MyD88 [Myeloid differentiation primary response gene (88)] to the receptor. As a result, MyD88 interacts with IRAK4, resulting in the formation of an active complex which interacts with and activates the kinases IRAK1 or IRAK2 (Kollewe, Mackensen, et al., Journal of Biological Chemistry, 2004; Precious et al., J. Biol. Chem., 2009). As a result of this, the NF (nuclear factor)-κB signalling pathway and the MAPK (mitogen-activated protein kinase) signal pathway is activated (Wang, Deng, et al., Nature, 2001). The activation both of the NF-κB signal pathway and of the MAPK signal pathway leads to processes associated with different immune processes. For example, there is increased expression of various inflammatory signal molecules and enzymes such as cytokines, chemokines and COX-2 (cyclooxygenase-2), and increased mRNA stability of inflammation-associated genes, for example COX-2, IL-6 (interleukin-6), IL-8 (Holtmann, Enninga, et al., Journal of Biological Chemistry, 2001; Datta, Novotny, et al., The Journal of Immunology, 2004). Furthermore, these processes may be associated with the proliferation and differentiation of particular cell types, for example monocytes, macrophages, dendritic cells, T cells and B cells (Wan, Chi, et al., Nat Immunol, 2006; McGettrick and J. O'Neill, British Journal of Haematology, 2007).

The central role of IRAK4 in the pathology of various inflammatory disorders had already been shown by direct comparison of wild-type (WT) mice with genetically modified animals having a kinase-inactivated form of IRAK4 (IRAK4 KDKI). IRAK4 KDKI animals have an improved clinical picture in the animal model of multiple sclerosis, atherosclerosis, myocardial infarction and Alzheimer's disease (Rekhter, Staschke, et al., Biochemical and Biophysical Research Communication, 2008; Maekawa, Mizue, et al., Circulation, 2009; Staschke, Dong, et al., The Journal of Immunology, 2009; Kim, Febbraio, et al., The Journal of Immunology, 2011; Cameron, Tse, et al., The Journal of Neuroscience, 2012). Furthermore, it was found that deletion of IRAK4 in the animal model protects against virus-induced myocarditis by an improved anti-viral reaction with simultaneously reduced systemic inflammation (Valaperti, Nishii, et al., Circulation, 2013). It has also been shown that the expression of IRAK4 correlates with the disease activity of Vogt-Koyanagi-Harada syndrome (Sun, Yang, et al., PLoS ONE, 2014). In addition, the high relevance of IRAK4 for immune complex-mediated IFNα (interferon-alpha) production by plasmacytoid dendritic cells, a key process in the pathogenesis of systemic lupus erythematosus (SLE), has been shown (Chiang et al., The Journal of Immunology, 2010). Furthermore, the signalling pathway is associated with obesity (Ahmad, R., P. Shihab, et al., Diabetology & Metabolic Syndrome, 2015). As well as the essential role of IRAK4 in congenital immunity, there are also hints that IRAK4 influences the differentiation of Th17 T cells, components of adaptive immunity. In the absence of IRAK4 kinase activity, fewer IL-17-producing T cells (Th17 T cells) are generated compared to WT mice. The inhibition of IRAK4 enables the prophylaxis and/or treatment of atherosclerosis, type 1 diabetes mellitus, rheumatoid arthritis, spondyloarthritis (especially psoriatic spondyloarthritis and Bekhterev's disease), lupus erythematosus, psoriasis, vitiligo, giant cell arteritis, chronic inflammatory bowel disorder and viral disorders, for example HIV (human immunodeficiency virus), hepatitis virus (Staschke, et al., The Journal of Immunology, 2009; Marquez, et al., Ann Rheum Dis, 2014; Zambrano-Zaragoza, et al., International Journal of Inflammation, 2014; Wang, et al., Experimental and Therapeutic Medicine, 2015; Ciccia, et al., Rheumatology, 2015).

Due to the central role of IRAK4 in the MyD88-mediated signal cascade of TLRs (except TLR3) and the IL-1 receptor family, the inhibition of IRAK4 can be utilized for the prophylaxis and/or treatment of disorders mediated by the receptors mentioned. TLRs and also components of the IL-1 receptor family are involved in the pathogenesis of rheumatoid arthritis, psoriasis, arthritis, myasthenia gravis, vasculitis, for example Behget's disease, granulomatosis with polyangiitis and giant cell arteritis, pancreatitis, systemic lupus erythematosus, dermatomyositis and polymyositis, metabolic syndrome including, for example, insulin resistance, hypertension, dyslipoproteinaemia and obesity, diabetes mellitus (type 1 and type 2), diabetic nephropathy, osteoarthritis, Sjögren syndrome and sepsis (Yang, Tuzun, et al., J Immunol, 2005; Candia, Marquez et al., The Journal of Rheumatology, 2007; Scanzello, Plaas, et al. Curr Opin Rheumatol, 2008; Deng, Ma-Krupa, et al., Circ Res, 2009; Roger, Froidevaux, et al, PNAS, 2009; Devaraj, Tobias, et al., Arterioscler Thromb Vase Biol, 2011; Kim, Cho, et al., Clin Rheumatol, 2010; Carrasco et al., Clinical and Experimental Rheumatology, 2011; Gambuzza, Licata, et al., Journal of Neuroimmunology, 2011; Fresno, Archives Of Physiology And Biochemistry, 2011; Volin and Koch, J Interferon Cytokine Res, 2011; Akash, Shen, et al., Journal of Pharmaceutical Sciences, 2012; Goh and Midwood, Rheumatology, 2012; Dasu, Ramirez, et al., Clinical Science, 2012; Ouziel, Gustot, et al., Am J Patho, 2012; Ramirez and Dasu, Curr Diabetes Rev, 2012, Okiyama et al., Arthritis Rheum, 2012; Chen et al., Arthritis Research & Therapy, 2013; Holle, Windmoller, et al., Rheumatology (Oxford), 2013; Li, Wang, et al., Pharmacology & Therapeutics, 2013; Sedimbi, Hagglof, et al., Cell Mol Life Sci, 2013; Caso, Costa, et al., Mediators of Inflammation, 2014; Cordiglieri, Marolda, et al., J Autoimmun, 2014; Jialal, Major, et al., J Diabetes Complications, 2014; Kaplan, Yazgan, et al., Scand J Gastroenterol, 2014; Talabot-Aye, et al., Cytokine, 2014; Zong, Dorph, et al., Ann Rheum Di, 2014; Ballak, Stienstra, et al., Cytokine, 2015; Timper, Seelig, et al., J Diabetes Complications, 2015). Skin diseases such as psoriasis, atopic dermatitis, Kindler's syndrome, bullous pemphigoid, allergic contact dermatitis, alopecia areata, acne inversa and acne vulgaris are associated with the IRAK4-mediated TLR signalling pathway as well as the IL-1R family (Schmidt, Mittnacht, et al., J Dermatol Sci, 1996; Hoffmann, J Investig Dermatol Symp Proc, 1999; Gilliet, Conrad, et al., Archives of Dermatology, 2004; Niebuhr, Langnickel, et al., Allergy, 2008; Miller, Adv Dermatol, 2008; Terhorst, Kalali, et al., Am J Clin Dermatol, 2010; Viguier, Guigue, et al., Annals of Internal Medicine, 2010; Cevikbas, Steinhoff, J Invest Dermatol, 2012; Minkis, Aksentijevich, et al., Archives of Dermatology, 2012; Dispenza, Wolpert, et al., J Invest Dermatol, 2012; Minkis, Aksentijevich, et al., Archives of Dermatology, 2012; Gresnigt and van de Veerdonk, Seminars in Immunology, 2013; Selway, Kurczab, et al., BMC Dermatology, 2013; Sedimbi, Hagglof, et al., Cell Mol Life Sci, 2013; Wollina, Koch, et al. Indian Dermatol Online, 2013; Foster, Baliwag, et al., The Journal of Immunology, 2014).

Pulmonary disorders such as pulmonary fibrosis, obstructive pulmonary disease (COPD), acute respiratory distress syndrome (ARDS), acute lung injury (ALI), interstitial lung disease (ILD), sarcoidosis and pulmonary hypertension also show an association with various TLR-mediated signal pathways. The pathogenesis of the pulmonary disorders may be either impacted by infectious or non-infectious processes (Ramirez Cruz, Maldonado Bernal, et al., Rev Alerg Mex, 2004; Jeyaseelan, Chu, et al., Infection and Immunity, 2005; Seki, Tasaka, et al., Inflammation Research, 2010; Xiang, Fan, et al., Mediators of Inflammation, 2010; Margaritopoulos, Antoniou, et al., Fibrogenesis & Tissue Repair, 2010; Hilberath, Carlo, et al., The FASEB Journal, 2011; Nadigel, Prefontaine, et al., Respiratory Research, 2011; Kovach and Standiford, International Immunopharmacology, 2011; Bauer, Shapiro, et al., Mol Med, 2012; Deng, Yang, et al., PLoS One, 2013; Freeman, Martinez, et al., Respiratory Research, 2013; Dubaniewicz, A., Human Immunology, 2013). TLRs and IL-1R family members are also involved in the pathogenesis of other inflammatory disorders such as allergy, Behget's disease, gout, lupus erythematosus, adult-onset Still's disease, pericarditis and chronic inflammatory bowel diseases such as ulcerative colitis and Crohn's disease, transplant rejection and graft-versus-host reaction, and so inhibition of IRAK4 here is a suitable prophylactic and/or therapeutic approach (Liu-Bryan, Scott, et al., Arthritis & Rheumatism, 2005; Piggott, Eisenbarth, et al., J Clin Inves, 2005; Christensen, Shupe, et al., Immunity, 2006; Cario, Inflammatory Bowel Diseases, 2010; Nickerson, Christensen, et al., The Journal of Immunology, 2010; Rakoff-Nahoum, Hao, et al., Immunity, 2006; Heimesaat, Fischer, et al., PLoS ONE, 2007; Heimesaat, Nogai, et al., Gut, 2010; Kobori, Yagi, et al., J Gastroenterol, 2010; Schmidt, Raghavan, et al., Nat Immunol, 2010; Shi, Mucsi, et al., Immunological Reviews, 2010; Leventhal and Schroppel, Kidney Int, 2012; Chen, Lin, et al., Arthritis Res Ther, 2013; Hao, Liu, et al., Curr Opin Gastroenterol, 2013; Kreisel and Goldstein, Transplant International, 2013; Li, Wang, et al., Pharmacology & Therapeutics, 2013; Walsh, Carthy, et al., Cytokine & Growth Factor Reviews, 2013; Zhu, Jiang, et al., Autoimmunity, 2013; Yap and Lai, Nephrology, 2013; Vennegaard, Dyring-Andersen, et al., Contact Dermatitis, 2014; D'Elia, Brucato, et al., Clin Exp Rheumatol, 2015; Jain, Thongprayoon, et al., Am J Cardiol., 2015; Li, Zhang, et al., Oncol Rep., 2015).

Gynaecological disorders mediated by TLR and the IL-1R family, such as adenomyosis, dysmenorrhoea, dyspareunia and endometriosis, especially endometriosis-associated pain and other endometriosis-associated symptoms such as dysmenorrhoea, dyspareunia, dysuria and dyschezia, can be positively influenced by the prophylactic and/or therapeutic use of IRAK4 inhibitors (Akoum, Lawson, et al., Human Reproduction, 2007; Allhorn, Boing, et al., Reproductive Biology and Endocrinology, 2008; Lawson, Bourcier, et al., Journal of Reproductive Immunology, 2008; Sikora, Mielczarek-Palacz, et al., American Journal of Reproductive Immunology, 2012; Khan, Kitajima, et al., Journal of Obstetrics and Gynaecology Research, 2013; Santulli, Borghese, et al., Human Reproduction, 2013). The prophylactic and/or therapeutic use of IRAK4 inhibitors can also have a positive influence on atherosclerosis (Seneviratne, Sivagurunathan, et al., Clinica Chimica Acta, 2012; Falck-Hansen, Kassiteridi, et al., International Journal of Molecular Sciences, 2013; Sedimbi, Hagglof, et al., Cell Mol Life Sci, 2013).

In addition to the disorders already mentioned, IRAK4-mediated TLR processes have been described in the pathogenesis of eye disorders such as retinal ischaemia, keratitis, allergic conjunctivitis, keratoconjunctivitis sicca, macular degeneration and uveitis (Kaarniranta and Salminen, J Mol Med (Berl), 2009; Sun and Pearlman, Investigative Ophthalmology & Visual Science, 2009; Redfern and McDermott, Experimental Eye Research, 2010; Kezic, Taylor, et al., J Leukoc Biol, 2011; Chang, McCluskey, et al., Clinical & Experimental Ophthalmology, 2012; Guo, Gao, et al., Immunol Cell Biol, 2012; Lee, Hattori, et al., Investigative Ophthalmology & Visual Science, 2012; Qi, Zhao, et al., Investigative Ophthalmology & Visual Science, 2014).

The inhibition of IRAK4 is also a suitable therapeutic approach for fibrotic disorders, for example hepatic fibrosis, myocarditis, primary biliary cirrhosis, cystic fibrosis (Zhao, Zhao, et al., Scand J Gastroenterol, 2011; Benias, Gopal, et al., Clin Res Hepatol Gastroenterol, 2012; Yang, L. and E. Seki, Front Physiol, 2012; Liu, Hu, et al., Biochim Biophys Acta., 2015).

By virtue of the key position that IRAK4 has in disorders mediated by TLR- and the IL-1R family, it is possible to treat chronic liver disorders, for example fatty liver hepatitis and especially non-alcoholic fatty liver disease (NAFLD) and/or non-alcoholic steatohepatitis (NASH), alcoholic steatohepatitis (ASH) in a preventative and/or therapeutic manner with IRAK4 inhibitors (Nozaki, Saibara, et al., Alcohol Clin Exp Res, 2004; Csak, T., A. Velayudham, et al., Am J Physiol Gastrointest Liver Physiol, 2011; Miura, Kodama, et al., Gastroenterology, 2010; Kamari, Shaish, et al., J Hepatol, 2011; Ye, Li, et al., Gut, 2012; Roh, Seki, J Gastroenterol Hepatol, 2013; Ceccarelli, S., V. Nobili, et al., World J Gastroenterol, 2014; Miura, Ohnishi, World J Gastroenterol, 2014; Stojsavljevic, Palcic, et al., World J Gastroenterol, 2014).

Because of the central role of IRAK4 in TLR-mediated processes, the inhibition of IRAK4 also enables the treatment and/or prevention of cardiovascular and neurological disorders, for example myocardial reperfusion damage, myocardial infarction, hypertension (Oyama, Blais, et al., Circulation, 2004; Timmers, Sluijter, et al., Circulation Research, 2008; Fang and Hu, Med Sci Monit, 2011; Bijani, International Reviews of Immunology, 2012; Bomfim, Dos Santos, et al., Clin Sci (Lond), 2012; Christia and Frangogiannis, European Journal of Clinical Investigation, 2013; Thompson and Webb, Clin Sci (Lond), 2013; Hernanz, Martinez-Revelles, et al., British Journal of Pharmacology, 2015; Frangogiannis, Curr Opin Cardiol, 2015; Bomfim, Echem, et al., Life Sciences, 2015), and also Alzheimer's disease, stroke, craniocerebral trauma, amyotrophic lateral sclerosis (ALS) and Parkinson's (Brough, Tyrrell, et al., Trends in Pharmacological Sciences, 2011; Carty and Bowie, Biochemical Pharmacology, 2011; Denes, Kitazawa, Cheng, et al., The Journal of Immunology, 2011; Lim, Kou, et al., The American Journal of Pathology, 2011; Béraud and Maguire-Zeiss, Parkinsonism & Related Disorders, 2012; Denes, Wilkinson, et al., Disease Models & Mechanisms, 2013; Noelker, Morel, et al., Sci. Rep., 2013; Wang, Wang, et al., Stroke, 2013; Xiang, Chao, et al., Rev Neurosci, 2015; Lee, Lee, et al., J Neuroinflammation, 2015).

Because of the involvement of TLR-mediated signals and IL-1 receptor family-mediated signals via IRAK4 in the case of pruritus and pain, including acute, chronic, inflammatory and neuropathic pain, there may be assumed to be a therapeutic effect in the indications mentioned through the inhibition of IRAK4. Examples of pain include hyperalgesia, allodynia, premenstrual pain, endometriosis-associated pain, post-operative pain, interstitial cystitis, CRPS (complex regional pain syndrome), trigeminal neuralgia, prostatitis, pain caused by spinal cord injury, inflammation-induced pain, lower back pain, cancer pain, chemotherapy-associated pain, HIV treatment-induced neuropathy, burn-induced pain and chronic pain (Wolf, Livshits, et al., Brain, Behavior, and Immunity, 2008; Kim, Lee, et al., Toll-like Receptors: Roles in Infection and Neuropathology, 2009; del Rey, Apkarian, et al., Annals of the New York Academy of Sciences, 2012; Guerrero, Cunha, et al., European Journal of Pharmacology, 2012; Kwok, Hutchinson, et al., PLoS ONE, 2012; Nicotra, Loram, et al., Experimental Neurology, 2012; Chopra and Cooper, J Neuroimmune Pharmacol, 2013; David, Ratnayake, et al., Neurobiology of Disease, 2013; Han, Zhao, et al., Neuroscience, 2013; Liu and Ji, Pflugers Arch., 2013; Stokes, Cheung, et al., Journal of Neuroinflammation, 2013; Zhao, Zhang, et al., Neuroscience, 2013; Liu, Zhang, et al., Cell Research, 2014; Park, Stokes, et al., Cancer Chemother Pharmacol, 2014; Van der Watt, Wilkinson, et al., BMC Infect Dis, 2014; Won, K. A., M. J. Kim, et al., J Pain, 2014; Min, Ahmad, et al., Photochem Photobiol., 2015; Schrepf, Bradley, et al., Brain Behav Immun, 2015; Wong, L., J. D. Done, et al., Prostate, 2015).

This also applies to some oncological disorders. Particular lymphomas, for example ABC-DLBCL (activated B-cell diffuse large-cell B-cell lymphoma), mantle cell lymphoma and Waldenström's disease, and also chronic lymphatic leukaemia, melanoma, pancreatic tumour and liver cell carcinoma, are characterized by mutations in MyD88 or changes in MyD88 activity which can be treated by an IRAK4 inhibitor (Ngo, Young, et al., Nature, 2011; Puente, Pinyol, et al., Nature, 2011; Ochi, Nguyen, et al., J Exp Med, 2012; Srivastava, Geng, et al., Cancer Research, 2012; Treon, Xu, et al., New England Journal of Medicine, 2012; Choi, Kim, et al., Human Pathology, 2013; (Liang, Chen, et al., Clinical Cancer Research, 2013). In addition, MyD88 plays an important role in ras-dependent tumours, and so IRAK4 inhibitors are also suitable for treatment thereof (Kfoury, A., K. L. Corf, et al., Journal of the National Cancer Institute, 2013). There can also be assumed to be a therapeutic effect in breast cancer, ovarian carcinoma, colorectal carcinoma, head and neck carcinoma, lung cancer, prostate cancer through the inhibition of IRAK4, since the indications mentioned are associated with the signalling pathway (Szczepanski, Czystowska, et al., Cancer Res, 2009; Zhang, He, et al., Mol Biol Rep, 2009; Wang, Qian, et al., Br J Cancer Kim, 2010; Jo, et al., World J Surg Oncol, 2012; Zhao, Zhang, et al.; Front Immunol, 2014; Chen, Zhao, et al., Int J Clin Exp Pathol, 2015).

Inflammatory disorders such as CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome; FMF (familial mediterranean fever), HIDS (hyper-IgD syndrome), TRAPS (tumour necrosis factor receptor 1-associated periodic syndrom), juvenile idiopathic arthritis, adult-onset Still's disease, Adamantiades-Behget's disease, rheumatoid arthritis, osteoarthritis, keratoconjunctivitis sicca, PAPA syndrome (pyogenic arthritis, Pyoderma gangraenosum and acne), Schnitzler's syndrome and Sjögren syndrome are treated by blocking the IL-1 signal pathway; therefore here, too, an IRAK4 inhibitor is suitable for treatment of the diseases mentioned (Narayanan, Corrales, et al., Cornea, 2008; Brenner, Ruzicka, et al., British Journal of Dermatology, 2009; Henderson and Goldbach-Mansky, Clinical Immunology, 2010; Dinarello, European Journal of Immunology, 2011; Gul, Tugal-Tutkun, et al., Ann Rheum Dis, 2012; Pettersson, Annals of MedicinePetterson, 2012; Ruperto, Brunner, et al., New England Journal of Medicine, 2012; Nordstrom, Knight, et al., The Journal of Rheumatology, 2012; Vijmasi, Chen, et al., Mol Vis, 2013; Yamada, Arakaki, et al., Opinion on Therapeutic Targets, 2013; de Koning, Clin Transl Allergy, 2014). The ligand of IL-33R, IL-33, is involved particularly in the pathogenesis of acute kidney failure, and so the inhibition of IRAK4 for prophylaxis and/or treatment is a suitable therapeutic approach (Akcay, Nguyen, et al., Journal of the American Society of Nephrology, 2011). Components of the IL-1 receptor family are associated with myocardial infarction, different pulmonary disorders such as asthma, COPD, idiopathic interstitial pneumonia, allergic rhinitis, pulmonary fibrosis and acute respiratory distress syndrome (ARDS), and so prophylactic and/or therapeutic action is to be expected in the indications mentioned through the inhibition of IRAK4 (Kang, Homer, et al., The Journal of Immunology, 2007; Imaoka, Hoshino, et al., European Respiratory Journal, 2008; Couillin, Vasseur, et al., The Journal of Immunology, 2009; Abbate, Kontos, et al., The American Journal of Cardiology, 2010; Lloyd, Current Opinion in Immunology, 2010; Pauwels, Bracke, et al., European Respiratory Journal, 2011; Haenuki, Matsushita, et al., Journal of Allergy and Clinical Immunology, 2012; Yin, Li, et al., Clinical & Experimental Immunology, 2012; Abbate, Van Tassell, et al., The American Journal of Cardiology, 2013; Alexander-Brett, et al., The Journal of Clinical Investigation, 2013; Bunting, Shadie, et al., BioMed Research International, 2013; Byers, Alexander-Brett, et al., The Journal of Clinical Investigation, 2013; Kawayama, Okamoto, et al., J Interferon Cytokine Res, 2013; Martinez-Gonzilez, Roca, et al., American Journal of Respiratory Cell and Molecular Biology, 2013; Nakanishi, Yamaguchi, et al., PLoS ONE, 2013; Qiu, Li, et al., Immunology, 2013; Li, Guabiraba, et al., Journal of Allergy and Clinical Immunology, 2014; Saluja, Ketelaar, et al., Molecular Immunology, 2014; Lugrin, Parapanov, et al., The Journal of Immunology, 2015).

The prior art discloses a multitude of IRAK4 inhibitors (see, for example, Annual Reports in Medicinal Chemistry (2014), 49, 117-133).

U.S. Pat. No. 8,293,923 and US20130274241 disclose IRAK4 inhibitors having a 3-substituted indazole structure. There is no description of 2-substituted indazoles.

WO2013106254 and WO2011153588 disclose 2,3-disubstituted indazole derivatives.

WO2007091107 describes 2-substituted indazole derivatives for the treatment of Duchenne muscular dystrophy. The compounds disclosed do not have 6-hydroxyalkyl substitution.

WO2015091426 describes indazoles, such as Example 64, substituted at the 2 position by a carboxamide side chain.

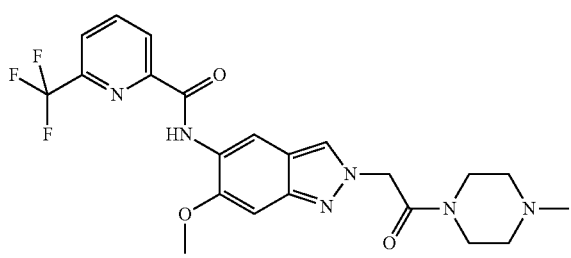 [SMILES: COc1cc2nn(CC(=O)N3CCN(C)CC3)cc2cc1NC(=O)c1cccc(C(F)(F)F)n1]

Example 64

WO2015104662 discloses 2-substituted indazoles of the following general formula:

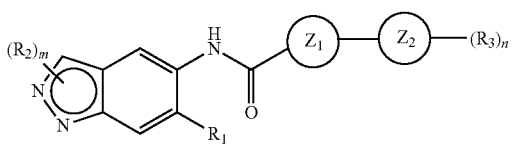

in which $R_2$ is an alkyl or cycloalkyl group. There are explicit descriptions of 2-substituted indazoles having a methyl, 2-methoxyethyl and cyclopentyl group at the 2 position (Examples 1, 4 and 76). Also described by Example 117 is an indazole derivative having a hydroxyethyl substituent at the 1 position. However, no indazole derivatives having a 3-hydroxy-3-methylbutyl substituent at the 1 position or 2 position are described.

Indazoles having a hydroxyl-substituted alkyl group in the 2 position are encompassed generically by the general formula, but are not disclosed explicitly in WO2015104662.

Indazoles having an alkyl group in the 2 position where the alkyl group is additionally substituted by a methylsulphonyl group are not encompassed by the general formula and the definitions of the $R_2$ substituents in WO2015104662.

In addition to the above-described substitution pattern on the indazole in 1 and 2 positions, WO2015104662 describes indazoles having substitution at the 6 position for which $R_1$ is defined as follows: alkyl, cyano, —$NR_aR_b$ or optionally substituted groups selected from cycloalkyl, aryl or heterocyclyl, where the substituents are independently alkyl, alkoxy, halogen, hydroxyl, hydroxyalkyl, amino, aminoalkyl, nitro, cyano, haloalkyl, haloalkoxy, —$OCOCH_2$—O-alkyl, —$OP(O)(O$-alkyl$)_2$ or —$CH_2$—$OP(O)(O$-alkyl$)_2$. For imidazole compounds in which $R_1$ is an alkyl group, the effective filing date is 7 Jan. 2015 (international filing date of WO2015104662). The Indian applications 146/CHE/2014 and 3018/CHE/2014 whose priority is claimed do not disclose any indazole compounds for which $R_1$ is an alkyl group.

Thus, indazole compounds of the following general formula:

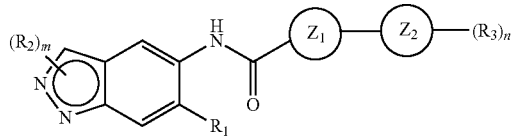

in which $R_1$ is an optionally substituted alkyl group are described for the first time on 7 Jan. 2015 and hence after the priority date of the present application.

Examples of substituents at the 6 position described in WO2015104662 for $R_1$ are cyclopropyl, cyclohexyl, cyano, 3-fluorophenyl and saturated heterocyclic substituents. Indazoles having a hydroxyl-substituted alkyl group at position 6 are not described explicitly in WO2015104662.

The problem addressed by the present invention is that of providing novel compounds that act as inhibitors of interleukin-1 receptor associated kinase-4 (IRAK4).

The novel IRAK4 inhibitors are especially suitable for treatment and for prevention of proliferative, metabolic and inflammatory disorders characterized by an overreacting immune system. Particular mention should be made here of inflammatory skin disorders, cardiovascular disorders, lung disorders, eye disorders, neurological disorders, pain disorders and cancer.

In addition, the novel IRAK4 inhibitors are suitable for treatment and prevention of autoimmune and inflammatory disorders, especially
    rheumatoid arthritis, multiple sclerosis, systemic lupus erythematosus, spondyloarthritis and gout,
of metabolic disorders, especially hepatic disorders such as fatty liver, and
of gynaecological disorders, especially of endometriosis and of endometriosis-associated pain and other endometriosis-associated symptoms such as dysmenorrhoea, dyspareunia, dysuria and dyschezia.

The present invention provides compounds of the general formula (I)

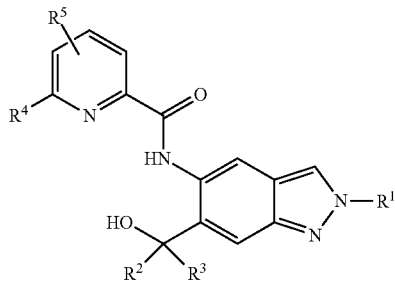

in which:
R¹ is $C_1$-$C_6$-alkyl, where the $C_1$-$C_6$-alkyl group is unsubstituted or mono- or polysubstituted identically or differently by
  halogen, hydroxyl, an unsubstituted or mono- or poly-halogen-substituted $C_3$-$C_6$-cycloalkyl, or an $R^6$, $R^7SO_2$, $R^7SO$ or $R^8O$ group,
  or a group selected from:

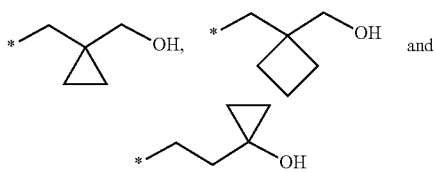

where * represents the bonding site of the group to the rest of the molecule;
R² and R³ always have the same definition and are both either hydrogen or $C_1$-$C_6$-alkyl;
R⁴ is halogen, cyano, an unsubstituted or a singly or multiply, identically or differently substituted $C_1$-$C_6$-alkyl or an unsubstituted or a singly or multiply, identically or differently substituted $C_3$-$C_6$-cycloalkyl, and the substituents are selected from the group of halogen and hydroxyl;
R⁵ is hydrogen, halogen or an unsubstituted or mono- or poly-halogen-substituted $C_1$-$C_6$-alkyl;
R⁶ is an unsubstituted or mono- or di-methyl-substituted monocyclic saturated heterocycle having 4 to 6 ring atoms, which contains a heteroatom or a heterogroup from the group of O, S, SO and $SO_2$;
R⁷ is $C_1$-$C_6$-alkyl, where the $C_1$-$C_6$-alkyl group is unsubstituted or mono- or polysubstituted identically or differently by halogen, hydroxyl or $C_3$-$C_6$-cycloalkyl, or R⁷ is $C_3$-$C_6$-cycloalkyl;
R⁸ is $C_1$-$C_6$-alkyl, where the $C_1$-$C_6$-alkyl group is unsubstituted or mono- or polysubstituted identically or differently by halogen;
and the diastereomers, enantiomers, metabolites, salts, solvates or solvates of the salts thereof.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x $CF_3COOH$", "x Na*" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Inventive compounds are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by the formula (I) and are mentioned below as embodiments and the salts, solvates and solvates of the salts thereof if the compounds that are encompassed by the formula (I) and are mentioned below are not already salts, solvates and solvates of the salts.

Preferred salts in the context of the present invention are physiologically acceptable salts of the inventive compounds. However, the invention also encompasses salts which themselves are unsuitable for pharmaceutical applications but which can be used, for example, for the isolation or purification of the inventive compounds.

Physiologically acceptable salts of the inventive compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the inventive compounds which form a complex in the solid or liquid state by coordination with solvent molecules. Hydrates are a specific form of the solvates in which the coordination is with water.

The inventive compounds may, depending on their structure, exist in different stereoisomeric forms, i.e. in the form of configurational isomers or else, if appropriate, of conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

If the inventive compounds can occur in tautomeric forms, the present invention encompasses all the tautomeric forms.

The present invention also encompasses all suitable isotopic variants of the inventive compounds. An isotopic variant of an inventive compound is understood here as meaning a compound in which at least one atom within the inventive compound has been exchanged for another atom of the same atomic number, but with a different atomic mass than the atomic mass which usually or predominantly occurs in nature. Examples of isotopes which can be incorporated into an inventive compound are those of hydrogen, carbon, nitrogen, oxygen, phosphorus, sulphur, fluorine, chlorine, bromine and iodine, such as 2H (deuterium), 3H (tritium), 13C, 14C, 15N, 17O, 18O, 32P, 33P, 33S, 34S, 35S, 36S, 18F, 36Cl, 82Br, 123I, 124I, 129I and 131I. Particular isotopic variants of an inventive compound, such as, in particular, those in which one or more radioactive isotopes have been incorporated, may be beneficial, for example, for the examination of the mechanism of action or of the active ingredient distribution in the body; because of the comparative ease of preparability and detectability, particularly compounds labelled with 3H or 14C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the inventive compounds may therefore in some cases also constitute a preferred embodiment of the present invention. Isotopic variants of the inventive compounds can be prepared by the processes known to those skilled in the art, for example by the methods described further below and the procedures described in the working examples, by using corresponding isotopic modifications of the respective reagents and/or starting compounds.

The present invention further provides all the possible crystalline and polymorphous forms of the inventive compounds, where the polymorphs may be present either as single polymorphs or as a mixture of a plurality of polymorphs in all concentration ranges.

The present invention additionally also encompasses prodrugs of the inventive compounds. The term "prodrugs" in this context refers to compounds which may themselves be biologically active or inactive but are converted (for example metabolically or hydrolytically) to inventive compounds during their residence time in the body.

In the context of the present invention, unless specified otherwise, the substituents have the following meanings:

Alkyl in the context of the invention represents a straight-chain or branched alkyl group having the particular number of carbon atoms specified. Examples include methyl, ethyl, n-propyl, isopropyl, n-butyl, isobutyl, 1-methylpropyl, 2-methylpropyl, tert-butyl, n-pentyl, 1-ethylpropyl, 1-methylbutyl, 2-methylbutyl, 3-methylbutyl, 2,2-dimethylpropyl, n-hexyl, 1-methylpentyl, 2-methylpentyl, 3-methylpentyl, 4-methylpentyl, 1-ethylbutyl and 2-ethylbutyl. Preference is given to methyl, ethyl, n-propyl, n-butyl, 2-methylbutyl, 3-methylbutyl and 2,2-dimethylpropyl.

Cycloalkyl in the context of the invention is a monocyclic saturated alkyl group having the number of carbon atoms specified in each case. Preferred examples include cyclopropyl, cyclobutyl, cyclopentyl and cyclohexyl.

Alkoxy in the context of the invention represents a straight-chain or branched alkoxy group having the particular number of carbon atoms specified. 1 to 6 carbon atoms are preferred. Examples include methoxy, ethoxy, n-propoxy, isopropoxy, 1-methylpropoxy, n-butoxy, isobutoxy, tert-butoxy, n-pentoxy, isopentoxy, 1-ethylpropoxy, 1-methylbutoxy, 2-methylbutoxy, 3-methylbutoxy and n-hexoxy. Particular preference is given to a linear or branched alkoxy group having 1 to 4 carbon atoms. Examples which may be mentioned as being preferred are methoxy, ethoxy, n-propoxy, 1-methylpropoxy, n-butoxy and isobutoxy.

Halogen in the context of the invention is fluorine, chlorine and bromine. Preference is given to fluorine.

Hydroxyl in the context of the invention is OH.

A monocyclic saturated heterocycle is a monocyclic saturated heterocycle which has 4 to 6 ring atoms and contains a heteroatom or a heterogroup from the group of O, S, SO and $SO_2$. A heterocycle having a heteroatom or a heterogroup from the group of O, SO and $SO_2$ is preferred. Examples include: oxetane, tetrahydrofuran, tetrahydro-2H-pyran-4-yl, 1,1-dioxidotetrahydro-2H-thiopyran-3-yl, 1,1-dioxidotetrahydro-2H-thiopyran-2-yl, 1,1-dioxidotetrahydro-2H-thiopyran-4-yl, 1,1-dioxidotetrahydrothiophen-3-yl, 1,1-dioxidotetrahydrothiophen-2-yl, 1,1-dioxidothietan-2-yl or 1,1-dioxidothietan-3-yl. Particular preference is given here to oxetane and tetrahydrofuran. Very particular preference is given to oxetan-3-yl.

A symbol * at a bond denotes the bonding site in the molecule.

When groups in the inventive compounds are substituted, the groups may be mono- or polysubstituted, unless specified otherwise. In the context of the present invention, all groups which occur more than once are defined independently of one another. Substitution by one, two or three identical or different substituents is preferred.

A preferred embodiment of $R^1$ is a $C_2$-$C_6$-alkyl group substituted by 1, 2 or 3 fluorine atoms. Particular preference is given to 2,2,2-trifluoroethyl, 3,3,3-trifluoropropyl and 4,4,4-trifluorobutyl. Very particular preference is given to a 4,4,4-trifluorobutyl group.

A further preferred embodiment of $R^1$ is a $C_2$-$C_6$-alkyl group substituted by one or two hydroxyl group(s) or one $C_1$-$C_3$-alkoxy or a tri-fluorine-substituted $C_1$-$C_3$-alkoxy. Particular preference is given to a $C_2$-$C_5$-alkyl group substituted by hydroxyl or $C_1$-$C_3$-alkoxy or trifluoromethoxy or 2,2,2-trifluoroethoxy. Very particular preference is given to 3-hydroxy-3-methylbutyl, 3-methoxypropyl, 3-hydroxypropyl, 3-trifluoromethoxypropyl, 2-methoxyethyl or 2-hydroxyethyl. Especially preferred is the 3-hydroxy-3-methylbutyl group.

Further preferably, $R^1$ is a $C_2$-$C_6$-alkyl group substituted by a $C_1$-$C_6$-alkyl-$SO_2$ group. A methyl-$SO_2$-substituted $C_2$-$C_4$-alkyl group is particularly preferred. Especially preferred for $R^1$ are 2-(methylsulphonyl)ethyl or 3-(methylsulphonyl)propyl. From the latter group, 2-(methylsulphonyl)ethyl is particularly preferred.

Additionally preferably, $R^1$ is a $C_1$-$C_3$-alkyl group substituted by oxetanyl, tetrahydrofuranyl, tetrahydro-2H-pyran-4-yl, 1,1-dioxidotetrahydro-2H-thiopyran-3-yl, 1,1-dioxidotetrahydro-2H-thiopyran-2-yl, 1,1-dioxidotetrahydro-2H-thiopyran-4-yl, 1,1-dioxidotetrahydrothiophen-3-yl, 1,1-dioxidotetrahydrothiophen-2-yl, 1,1-dioxidothietan-2-yl or 1,1-dioxidothietan-3-yl. Particular preference is given to a $C_1$-$C_3$-alkyl group substituted by an oxetane group. Especially preferred for $R^1$ is an oxetan-3-ylmethyl group.

For $R^2$ and $R^3$, which always have the same definition, hydrogen or methyl are preferred. Methyl is particularly preferred.

In the case of $R^4$, preference is given to an unsubstituted or mono- or poly-halogen-substituted $C_1$-$C_3$-alkyl group or a $C_1$-$C_3$-alkyl group substituted by one hydroxyl group or a $C_1$-$C_3$-alkyl group substituted by one hydroxyl group and three fluorine atoms.

For $R^4$, particular preference is given to the following groups: methyl, ethyl, trifluoro-$C_1$-$C_3$-alkyl, difluoro-$C_1$-$C_3$-alkyl, hydroxymethyl, 1-hydroxyethyl, 2-hydroxypropan-2-yl and 2,2,2-trifluoro-1-hydroxyethyl. For $R^4$, particular preference is given to the methyl, trifluoromethyl and difluoromethyl groups. Particular preference is given here to a trifluoromethyl group.

A preferred embodiment of $R^5$ is hydrogen, fluorine, chlorine or $C_1$-$C_3$-alkyl. More preferably, $R^5$ is hydrogen, fluorine or methyl. Most preferably, $R^5$ is hydrogen or fluorine.

Particular preference is also given to compounds in which $R^4$ is methyl or trifluoromethyl and $R^5$ is fluorine. Very particular preference is given to compounds in which $R^4$ is methyl and $R^S$ is fluorine, where $R^5$ is in the ortho position to $R^4$.

For $R^6$, preferred embodiments include oxetanyl, tetrahydrofuranyl, tetrahydro-2H-pyran-4-yl, 1,1-dioxidotetrahydro-2H-thiopyran-3-yl, 1,1-dioxidotetrahydro-2H-thiopyran-2-yl, 1,1-dioxidotetrahydro-2H-thiopyran-4-yl, 1,1-dioxidotetrahydrothiophen-3-yl, 1,1-dioxidotetrahydrothiophen-2-yl, 1,1-dioxidothietan-2-yl or 1,1-dioxidothietan-3-yl. Particular preference is given here to oxetanyl. Very particular preference is given to oxetan-3-yl.

$R^7$ is exclusively connected to the functional groups —$SO_2$— and —SO—, i.e. is an $R^7$-substituted —$SO_2$— or SO group. In this connection, $R^7$ is preferably $C_1$-$C_4$-alkyl, where the $C_1$-$C_4$-alkyl group is unsubstituted or monosubstituted by hydroxyl or by cyclopropyl or substituted by three fluorine atoms. Additionally preferred for $R^7$ is a cyclopropyl group. Particularly preferred for $R^7$ are methyl, ethyl or hydroxyethyl. Very particular preference is given to methyl for $R^7$.

This means that, in the case of a $C_1$-$C_6$-alkyl group substituted by $R^7SO_2$— or $R^7SO$—, in the context of $R^1$, preference is given to a $C_1$-$C_6$-alkyl substituted by a $C_1$-$C_6$-alkyl-$SO_2$ or a $C_1$-$C_6$-alkyl-SO. For $R^1$, preference is given here especially to methylsulphonylethyl and methylsulphonylpropyl. Very particular preference is given here to methylsulphonylethyl.

For $R^8$, preference is given to an unsubstituted $C_1$-$C_4$-alkyl group or a tri-fluorine-substituted $C_1$-$C_4$-alkyl group. Particular preference is given to methyl, ethyl, trifluoromethyl or 2,2,2-trifluoroethyl.

Very particular preference is given to methyl, trifluoromethyl or 2,2,2-trifluoroethyl.

Preference is given to compounds of the formula (I) in which $R^1$ is $C_1$-$C_6$-alkyl, where the $C_1$-$C_6$-alkyl group is unsubstituted or mono- or polysubstituted identically or differently by fluorine, hydroxyl or an $R^6$, $R^7SO_2$, $R^7SO$ or $R^8O$ group;

$R^2$ and $R^3$ always have the same definition and are both either hydrogen or $C_1$-$C_3$-alkyl;

$R^4$ is halogen, cyano or $C_1$-$C_3$-alkyl, where the $C_1$-$C_3$-alkyl group is unsubstituted or mono- or polysubstituted identically or differently by halogen or hydroxyl;

$R^5$ is hydrogen, fluorine, chlorine or $C_1$-$C_3$-alkyl;

$R^6$ is oxetanyl or tetrahydrofuranyl;

$R^7$ is $C_1$-$C_4$-alkyl, where the $C_1$-$C_4$-alkyl group is unsubstituted or monosubstituted by hydroxyl or by cyclopropyl or substituted by three fluorine atoms;

$R^8$ is unsubstituted $C_1$-$C_4$-alkyl or tri-fluorine-substituted $C_1$-$C_4$-alkyl;

and the diastereomers, enantiomers, metabolites, salts, solvates or solvates of the salts thereof.

Preference is additionally given to compounds of the formula (I) in which $R^1$ is $C_2$-$C_6$-alkyl, where $C_2$-$C_6$-alkyl is unsubstituted, or $C_2$-$C_6$-alkyl is mono-, di- or tri-fluorine-substituted or $C_2$-$C_6$-alkyl is monosubstituted by hydroxyl, $R^6$, $R^7SO_2$, or $R^8O$, or in which $R^1$ is an oxetanyl-substituted $C_1$-$C_3$-alkyl;

$R^2$ and $R^3$ always have the same definition and are both either hydrogen or methyl;

$R^4$ is an unsubstituted or mono- or poly-halogen-substituted $C_1$-$C_3$-alkyl group or a $C_1$-$C_3$-alkyl group substituted by one hydroxyl group or a $C_1$-$C_3$-alkyl group substituted by one hydroxyl group and three fluorine atoms;

$R^5$ is hydrogen, fluorine or $C_1$-$C_3$-alkyl;

$R^7$ is $C_1$-$C_3$-alkyl;

$R^8$ is $C_1$-$C_4$-alkyl, where the $C_1$-$C_4$-alkyl group is unsubstituted or mono-, di- or tri-fluorine-substituted;

and the diastereomers, enantiomers, metabolites, salts, solvates or solvates of the salts thereof.

Particular preference is also given to compounds of the general formula (I) in which $R^1$ is a $C_2$-$C_5$-alkyl group substituted by hydroxyl or $C_1$-$C_3$-alkoxy or trifluoromethoxy or 2,2,2-trifluoroethoxy or trifluoromethyl or is a methyl-$SO_2$-substituted $C_2$-$C_4$-alkyl group or is an oxetan-3-yl-substituted $C_1$-$C_2$-alkyl group;

$R^2$ and $R^3$ always have the same definition and are both hydrogen or methyl;

$R^4$ is methyl, ethyl, trifluoro-$C_1$-$C_3$-alkyl, difluoro-$C_1$-$C_3$-alkyl, hydroxymethyl, 1-hydroxyethyl, 2-hydroxypropan-2-yl and 2,2,2-trifluoro-1-hydroxyethyl and $R^5$ is hydrogen, fluorine or methyl;

and the diastereomers, enantiomers, metabolites, salts, solvates or solvates of the salts thereof.

Very particular preference is given to compounds in which $R^1$ is 4,4,4-trifluorobutyl, 3-hydroxy-3-methylbutyl, 3-hydroxybutyl, 3-methoxypropyl, 3-hydroxypropyl, 3-hydroxy-2-methylpropyl, 3-hydroxy-2,2-dimethylpropyl, 3-trifluoromethoxypropyl, 2-methoxyethyl, 2-hydroxyethyl, 2-(methylsulphonyl)ethyl or 3-(methylsulphonyl)propyl;

$R^2$ and $R^3$ are both methyl or hydrogen and $R^4$ is difluoromethyl, trifluoromethyl or methyl and $R^5$ is hydrogen or fluorine;

and the diastereomers, enantiomers, metabolites, salts, solvates or solvates of the salts thereof.

Very particular preference is also given to compounds in which $R^1$ is 3-hydroxy-3-methylbutyl, 3-hydroxybutyl, 3-hydroxy-2-methylpropyl, 3-hydroxy-2,2-dimethylpropyl, 3-(methylsulphonyl)propyl or 2-(methylsulphonyl)ethyl;

$R^2$ and $R^3$ are both methyl;

$R^4$ is difluoromethyl or trifluoromethyl; and $R^5$ is hydrogen;

and the diastereomers, enantiomers, metabolites, salts, solvates or solvates of the salts thereof.

Particular preference is additionally also given to compounds in which $R^1$ is 3-hydroxy-3-methylbutyl, 3-hydroxybutyl, 3-hydroxy-2-methylpropyl, 3-hydroxy-2,2-dimethylpropyl, 3-(methylsulphonyl)propyl or 2-(methylsulphonyl)ethyl;

$R^2$ and $R^3$ are both methyl;

R⁴ is methyl and
R⁵ is fluorine, where R⁵ is in the ortho position to R⁴;
and the diastereomers, enantiomers, metabolites, salts, solvates or solvates of the salts thereof.

The present invention especially provides the following compounds:
1) N-[6-(2-Hydroxypropan-2-yl)-2-(2-methoxyethyl)-2H-indazol-5-yl]-6-(trifluoromethyl)pyridine-2-carboxamide
2) N-[6-(Hydroxymethyl)-2-(2-methoxyethyl)-2H-indazol-5-yl]-6-(trifluoromethyl)pyridine-2-carboxamide
3) N-[6-(2-Hydroxypropan-2-yl)-2-(3-methoxypropyl)-2H-indazol-5-yl]-6-(trifluoromethyl)pyridine-2-carboxamide
4) N-[6-(Hydroxymethyl)-2-(3-methoxypropyl)-2H-indazol-5-yl]-6-(trifluoromethyl)pyridine-2-carboxamide
5) N-[2-(2-Hydroxyethyl)-6-(2-hydroxypropan-2-yl)-2H-indazol-5-yl]-6-(trifluoromethyl)pyridine-2-carboxamide
6) N-[6-(2-Hydroxypropan-2-yl)-2-(3-hydroxypropyl)-2H-indazol-5-yl]-6-(trifluoromethyl)pyridine-2-carboxamide
7) N-[2-(2-Hydroxyethyl)-6-(hydroxymethyl)-2H-indazol-5-yl]-6-(trifluoromethyl)pyridine-2-carboxamide
8) N-[6-(2-Hydroxypropan-2-yl)-2-(oxetan-3-ylmethyl)-2H-indazol-5-yl]-6-(trifluoromethyl)pyridine-2-carboxamide
9) N-[6-(Hydroxymethyl)-2-(oxetan-3-ylmethyl)-2H-indazol-5-yl]-6-(trifluoromethyl)pyridine-2-carboxamide
10) N-{6-(2-Hydroxypropan-2-yl)-2-[3-(methylsulphonyl)propyl]-2H-indazol-5-yl}-6-(trifluoromethyl)pyridine-2-carboxamide
11) N-[2-(3-Hydroxy-3-methylbutyl)-6-(2-hydroxypropan-2-yl)-2H-indazol-5-yl]-6-(trifluoromethyl)pyridine-2-carboxamide
12) N-{6-(2-Hydroxypropan-2-yl)-2-[2-(methylsulphonyl)ethyl]-2H-indazol-5-yl}-6-(trifluoromethyl)pyridine-2-carboxamide
13) 6-(Difluoromethyl)-N-[2-(3-hydroxy-3-methylbutyl)-6-(2-hydroxypropan-2-yl)-2H-indazol-5-yl]pyridine-2-carboxamide
14) 6-(Difluoromethyl)-N-{6-(2-hydroxypropan-2-yl)-2-[2-(methylsulphonyl)ethyl]-2H-indazol-5-yl}pyridine-2-carboxamide
15) 6-(Difluoromethyl)-N-[6-(2-hydroxypropan-2-yl)-2-(3-hydroxypropyl)-2H-indazol-5-yl]pyridine-2-carboxamide
16) N-[6-(2-Hydroxypropan-2-yl)-2-(4,4,4-trifluorobutyl)-2H-indazol-5-yl]-6-(trifluoromethyl)pyridine-2-carboxamide
17) N-{6-(2-Hydroxypropan-2-yl)-2-[3-(trifluoromethoxy)propyl]-2H-indazol-5-yl}-6-(trifluoromethyl)pyridine-2-carboxamide
18) N-{6-(2-Hydroxypropan-2-yl)-2-[3-(2,2,2-trifluoroethoxy)propyl]-2H-indazol-5-yl}-6-(trifluoromethyl)pyridine-2-carboxamide
19) 5-Fluoro-N-[2-(3-hydroxy-3-methylbutyl)-6-(2-hydroxypropan-2-yl)-2H-indazol-5-yl]-6-methylpyridine-2-carboxamide
20) N-[2-(3-Hydroxy-3-methylbutyl)-6-(2-hydroxypropan-2-yl)-2H-indazol-5-yl]-6-methylpyridine-2-carboxamide
21) 6-(2-Hydroxypropan-2-yl)-N-[6-(2-hydroxypropan-2-yl)-2-(4,4,4-trifluorobutyl)-2H-indazol-5-yl]pyridine-2-carboxamide
22) N-{2-[2-(1-Hydroxycyclopropyl)ethyl]-6-(2-hydroxypropan-2-yl)-2H-indazol-5-yl}-6-(trifluoromethyl)pyridine-2-carboxamide The invention further provides a process for preparing compounds of the general formula (III) from compounds of the general formula (II)

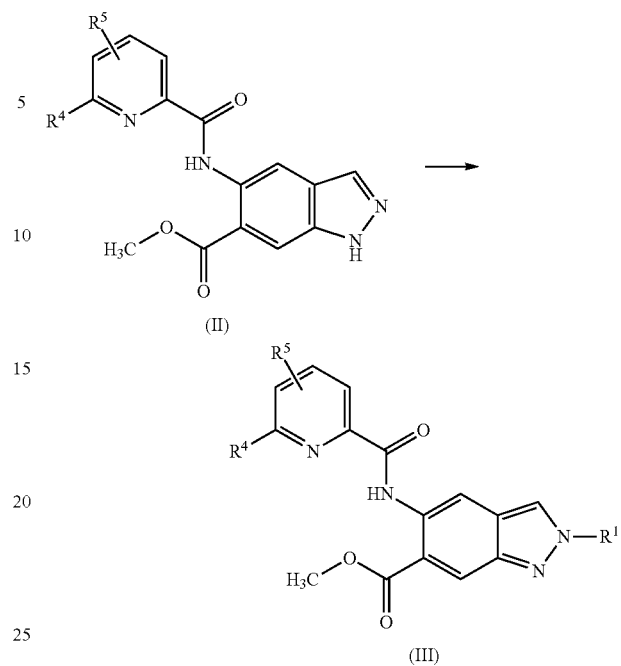

in which
R¹ is 4,4,4-trifluorobutyl, 3-hydroxy-3-methylbutyl, 3-methoxypropyl, 3-hydroxypropyl, 3-hydroxy-2-methylpropyl, 3-hydroxy-2,2-dimethylpropyl, 3-trifluoromethoxypropyl, 2-methoxyethyl, 2-hydroxyethyl, 2-(methylsulphonyl)ethyl, 3-(methylsulphonyl)propyl or 2-(1-hydroxycyclopropyl)ethyl;
R⁴ is difluoromethyl, trifluoromethyl or methyl; and
R⁵ is hydrogen or fluorine;
by the reaction of (II) with appropriately substituted alkyl halides or alkyl 4-methylbenzenesulphonates in the presence of potassium carbonate.

The invention further provides compounds of the general formula (III)

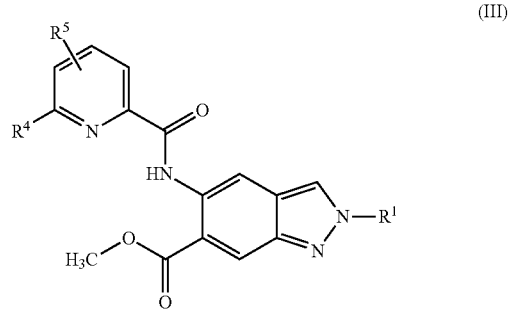

in which
R¹ is 4,4,4-trifluorobutyl, 3-hydroxy-3-methylbutyl, 3-methoxypropyl, 3-hydroxypropyl, 3-hydroxybutyl, 3-hydroxy-2-methylpropyl, 3-hydroxy-2,2-dimethylpropyl, 3-trifluoromethoxypropyl, 2-methoxyethyl, 2-hydroxyethyl, 2-(methylsulphonyl)ethyl, 3-(methylsulphonyl)propyl or 2-(1-hydroxycyclopropyl)ethyl;
R⁴ is difluoromethyl, trifluoromethyl or methyl; and
R⁵ is hydrogen or fluorine;
and the diastereomers, enantiomers, metabolites, salts, solvates or solvates of the salts thereof.

Preference is especially given to the following compounds of the general formula (III):
methyl 5-{[(5-fluoro-6-methylpyridin-2-yl)carbonyl]amino}-2-(3-hydroxy-3-methylbutyl)-2H-indazole-6-carboxylate and
methyl 2-(3-hydroxy-3-methylbutyl)-5-({[6-(trifluoromethyl)pyridin-2-yl]carbonyl}amino)-2H-indazole-6-carboxylate.

The compounds of the general formula (III) are suitable for preparation of a portion of the compounds of the general formula (I).

Furthermore, the compounds of the general formula (III) are inhibitors of interleukin-1 receptor associated kinase-4 (IRAK4).

The invention further provides a process for preparing the inventive compounds of the general formula (I) from compounds of the formula (III)

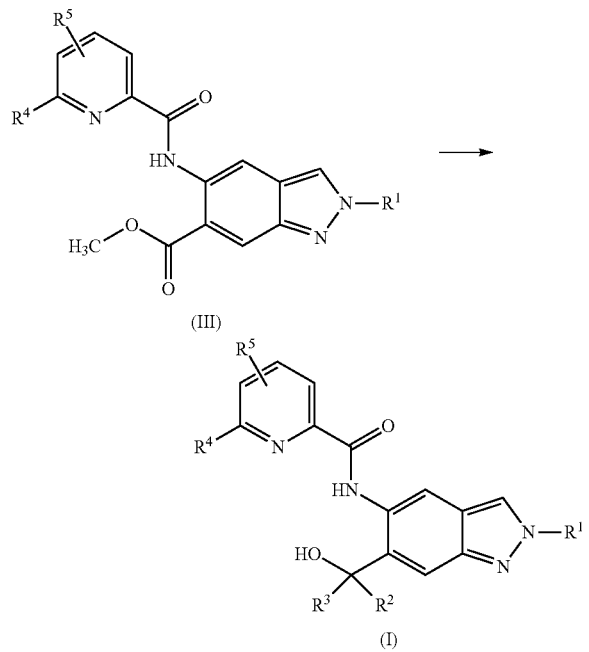

in which
R$^1$ is 4,4,4-trifluorobutyl, 3-hydroxy-3-methylbutyl, 3-hydroxybutyl, 3-methoxypropyl, 3-hydroxypropyl, 3-hydroxy-2-methylpropyl, 3-hydroxy-2,2-dimethylpropyl, 3-trifluoromethoxypropyl, 2-methoxyethyl, 2-hydroxyethyl, 3-(methylsulphonyl)propyl 2-(1-hydroxycyclopropyl)ethyl;
R$^2$ and R$^3$ are methyl;
R$^4$ is difluoromethyl, trifluoromethyl or methyl; and
R$^5$ is hydrogen or fluorine;
by a Grignard reaction with methylmagnesium bromide.

The inventive compounds act as inhibitors of IRAK4 kinase and have an unforeseeable useful pharmacological activity spectrum.

Thus, in addition to the subject matter mentioned above, the present invention also provides the use of the inventive compounds for treatment and/or prophylaxis of diseases in man and animals. Treatment and/or prophylaxis of gynaecological disorders, inflammatory skin disorders, cardiovascular disorders, pulmonary disorders, eye disorders, autoimmune disorders, pain disorders, metabolic disorders, gout, hepatic disorders, metabolic syndrome, insulin resistance and cancers with the inventive IRAK4 inhibitors is particularly preferred.

The inventive compounds are suitable for prophylaxis and/or treatment of various disorders and disease-related states, especially disorders mediated by TLR (except TLR3) and/or the IL-1 receptor family and/or disorders whose pathology is mediated directly by IRAK4. IRAK4-associated disorders include multiple sclerosis, atherosclerosis, myocardial infarction, Alzheimer's disease, virus-induced myocarditis, gout, Vogt-Koyanagi-Harada syndrome, lupus erythematosus, psoriasis, spondyloarthritis and arthritis.

The inventive compounds can also be used for prophylaxis and/or treatment of disorders mediated by MyD88 and TLR (except for TLR3). This includes multiple sclerosis, rheumatoid arthritis, spondyloarthritis (especially psoriatic spondyloarthritis and Bekhterev's disease), metabolic syndrome including insulin resistance, diabetes mellitus, osteoarthritis, Sjögren syndrome, giant cell arteritis, sepsis, poly- and dermatomyositis, skin disorders such as psoriasis, atopic dermatitis, alopecia areata, acne inversa and acne vulgaris, pulmonary disorders such as pulmonary fibrosis, chronic obstructive pulmonary disease (COPD), acute respiratory distress syndrome (ARDS), acute lung injury (ALI), interstitial lung disease (ILD), sarcoidosis and pulmonary hypertension.

Because of the mechanism of action of the inventive compounds, they are suitable for prophylaxis and/or treatment of the TLR-mediated disorders Behget's disease, gout, endometriosis and endometriosis-associated pain and other endometriosis-associated symptoms such as dysmenorrhoea, dyspareunia, dysuria and dyschezia. In addition, the inventive compounds are suitable for prophylaxis and/or treatment in the case of transplant rejection, lupus erythematosus, adult-onset Still's disease and chronic inflammatory bowel diseases such as ulcerative colitis and Crohn's disease.

In addition to the disorders already listed, the use of the inventive compounds is also suitable for treatment and/or prevention of the following disorders: eye disorders such as keratitis, allergic conjunctivitis, keratoconjunctivitis sicca, macular degeneration and uveitis; cardiovascular disorders such as atherosclerosis, myocardial reperfusion damage, myocardial infarction, hypertension and neurological disorders such as Alzheimer's disease, stroke and Parkinson's.

The mechanism of action of the inventive compounds also enables the prophylaxis and/or treatment of hepatic disorders mediated by TLR and the IL-1 receptor family, especially NAFLD, NASH, ASH, liver fibrosis and liver cirrhosis.

The prophylaxis and/or treatment of pruritus and pain, especially of acute, chronic, inflammatory and neuropathic pain, is also provided by the inventive compounds.

Because of the mechanism of action of the inventive compounds, they are suitable for prophylaxis and/or treatment of oncological disorders such as lymphoma, chronic lymphatic leukaemia, melanoma and liver cell carcinoma, breast cancer, prostate cancer and Ras-dependent tumours.

Moreover, the inventive compounds are suitable for the treatment and/or prevention of disorders mediated via the IL-1 receptor family. These disorders include CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome, FMF (familial mediterranean fever), HIDS (hyper-IgD syndrome), TRAPS (tumour necrosis factor receptor 1-associated periodic syndrome), juvenile idiopathic arthritis, adult-onset Still's disease, Adamantiades-Behget's disease, rheumatoid arthritis, psoriasis, arthritis, Bekhterev's disease, osteoarthritis, keratoconjunctivitis sicca und Sjögren syndrome, multiple sclerosis, lupus erythematosus, alopecia areata, type 1 diabetes mellitus, type 2 diabetes mellitus and the sequelae of myocardial infarction. Pulmonary disorders such as asthma, COPD, idiopathic interstitial pneumonia and ARDS, gynaecological disorders such as endometriosis and endometriosis-associated pain and other endometriosis-associated symptoms such as dysmenorrhoea, dyspareunia, dysuria and dyschezia, chronic-inflammatory bowel diseases such as Crohn's disease and ulcerative colitis are associated with dysregulation of the IL-1 receptor family and are suitable for therapeutic and/or prophylactic use of the inventive compounds.

The inventive compounds can also be used for treatment and/or prevention of IL-1 receptor family-mediated neurological disorders such as stroke, Alzheimer's disease, craniocerebral trauma, and dermatological disorders such as psoriasis, atopic dermatitis, acne inversa, alopecia areata and allergic contact dermatitis.

In addition, the inventive compounds are suitable for the treatment and/or prophylaxis of pain disorders, especially of acute, chronic, inflammatory and neuropathic pain. This preferably includes hyperalgesia, allodynia, pain from arthritis (such as osteoarthritis, rheumatoid arthritis and spondyloarthritis), premenstrual pain, endometriosis-associated pain, post-operative pain, pain from interstitial cystitis, CRPS (complex regional pain syndrome), trigeminal neuralgia, pain from prostatitis, pain caused by spinal cord injuries, inflammation-induced pain, lower back pain, cancer pain, chemotherapy-associated pain, HIV treatment-induced neuropathy, burn-induced pain and chronic pain.

The present invention further also provides a method for treatment and/or prevention of disorders, especially the disorders mentioned above, using an effective amount of at least one of the inventive compounds.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The inventive compounds can be used alone or, if required, in combination with other active ingredients. The present invention further provides medicaments containing at least one of the inventive compounds and one or more further active ingredients, especially for treatment and/or prevention of the abovementioned disorders. Preferred examples of active ingredients suitable for combinations include:

General mention may be made of active ingredients such as antibacterial (e.g. penicillins, vancomycin, ciprofloxacin), antiviral (e.g. aciclovir, oseltamivir) and antimycotic (e.g. naftifin, nystatin) substances and gamma globulins, immunomodulatory and immunosuppressive compounds such as cyclosporin, Methotrexat®, TNF antagonists (e.g. Humira®, Etanercept, Infliximab), IL-1 inhibitors (e.g. Anakinra, Canakinumab, Rilonacept), phosphodiesterase inhibitors (e.g. Apremilast), Jak/STAT inhibitors (e.g. Tofacitinib, Baricitinib, GLPG0634), leflunomid, cyclophosphamide, rituximab, belimumab, tacrolimus, rapamycin, mycophenolate mofetil, interferons, corticosteroids (e.g. prednisone, prednisolone, methylprednisolone, hydrocortisone, betamethasone), cyclophosphamide, azathioprine and sulfasalazine; paracetamol, non-steroidal anti-inflammatory substances (NSAIDS) (aspirin, ibuprofen, naproxen, etodolac, celecoxib, colchicine). The following should be mentioned for tumour therapy: immunotherapy (e.g. aldesleukin, alemtuzumab, basiliximab, catumaxomab, celmoleukin, denileukin diftitox, eculizumab, edrecolomab, gemtuzumab, ibritumomab tiuxetan, imiquimod, interferon-alpha, interferon beta, interferon-gamma, ipilimumab, lenalidomide, lenograstim, mifamurtide, ofatumumab, oprelvekin, picibanil, plerixafor, polysaccharide-K, sargramostim, sipuleucel-T, tasonermin, teceleukin, tocilizumab), antiproliferative substances, for example but not exclusively amsacrine, arglabin, arsenic trioxide, asparaginase, bleomycin, busulfan, dactinomycin, docetaxel, epirubicin, peplomycin, trastuzumab, rituximab, obinutuzumab, ofatumumab, tositumomab, aromatase inhibitors (e.g. exemestane, fadrozole, formestane, letrozole, anastrozole, vorozole), antioestrogens (e.g. chlormadinone, fulvestrant, mepitiostane, tamoxifen, toremifen), oestrogens (e.g. oestradiol, polyoestradiol phosphate, raloxifen), gestagens (e.g. medroxyprogesterone, megestrol), topoisomerase I inhibitors (e.g. irinotecan, topotecan), topoisomerase II inhibitors (e.g. amrubicin, daunorubicin, elliptiniumacetate, etoposide, idarubicin, mitoxantrone, teniposide), microtubuli-active substances (e.g. cabazitaxel, eribulin, paclitaxel, vinblastine, vincristine, vindesine, vinorelbine), telomerase inhibitors (e.g. imetelstat), alkylating substances and histone deacetylase inhibitors (e.g. bendamustine, carmustine, chlormethine, dacarbazine, estramustine, ifosfamide, lomustine, mitobronitol, mitolactol, nimustine prednimustine, procarbazine, ranimustine, streptozotocin, temozolomide, thiotepa, treosulfan, trofosfamide, vorinostat, romidepsin, panobinostat); substances which affect cell differentiation processes, such as abarelix, aminoglutethimide, bexarotene, MMP inhibitors (peptide mimetics, non-peptide mimetics and tetracyclines, for example marimastat, BAY 12-9566, BMS-275291, clodronate, prinomastat, doxycycline), mTOR inhibitors (e.g. sirolimus, everolimus, temsirolimus, zotarolimus), antimetabolites (e.g. clofarabine, doxifluridine, methotrexate, 5-fluorouracil, cladribine, cytarabine, fludarabine, mercaptopurine, methotrexate, pemetrexed, raltitrexed, tegafur, tioguanine), platinum compounds (e.g. carboplatin, cisplatin, cisplatinum, eptaplatin, lobaplatin, miriplatin, nedaplatin, oxaliplatin); antiangiogenic compounds (e.g. bevacizumab), antiandrogenic compounds (e.g. bevacizumab, enzalutamide, flutamide, nilutamide, bicalutamide, cyproterone, cyproterone acetate), proteasome inhibitors (e.g. bortezomib, carfilzomib, oprozomib, ONYX0914), gonadoliberin agonists and antagonists (e.g. abarelix, buserelin, deslorelin, ganirelix, goserelin, histrelin, triptorelin, degarelix, leuprorelin), methionine aminopeptidase inhibitors (e.g. bengamide derivatives, TNP-470, PPI-2458), heparanase inhibitors (e.g. SST0001, PI-88); inhibitors against genetically modified Ras protein (e.g. farnesyl transferase inhibitors such as lonafarnib, tipifarnib), HSP90 inhibitors (e.g.

geldamycin derivatives such as 17-allylaminogeldanamycin, 17-demethoxygeldanamycin (17AAG), 17-DMAG, retaspimycin hydrochloride, IPI-493, AUY922, BIIB028, STA-9090, KW-2478), kinesin spindle protein inhibitors (e.g. SB715992, SB743921, pentamidine/chlorpromazine), MEK (mitogen-activated protein kinase kinase) inhibitors (e.g. trametinib, BAY 86-9766 (refametinib), AZD6244), kinase inhibitors (e.g.: sorafenib, regorafenib, lapatinib, Sutent®, dasatinib, cetuximab, BMS-908662, GSK2118436, AMG 706, erlotinib, gefitinib, imatinib, nilotinib, pazopanib, roniciclib, sunitinib, vandetanib, vemurafenib), hedgehog signalling inhibitors (e.g. cyclopamine, vismodegib), BTK (Bruton's tyrosine kinase) inhibitor (e.g. ibrutinib), JAK/pan-JAK (janus kinase) inhibitor (e.g. SB-1578, baricitinib, tofacitinib, pacritinib, momelotinib, ruxolitinib, VX-509, AZD-1480, TG-101348), PI3K inhibitor (e.g. BAY 1082439, BAY 80-6946 (copanlisib), ATU-027, SF-1126, DS-7423, GSK-2126458, buparlisib, PF-4691502, BYL-719, XL-147, XL-765, idelalisib), SYK (spleen tyrosine kinase) inhibitors (e.g. fostamatinib, Excellair, PRT-062607), p53 gene therapy, bisphosphonates (e.g. etidronate, clodronate, tiludronate, pamidronate, alendronic acid, ibandronate, risedronate, zoledronate). For combination, the following active ingredients should also be mentioned by way of example but not exclusively: rituximab, cyclophosphamide, doxorubicin, doxorubicin in combination with oestrone, vincristine, chlorambucil, fludarabin, dexamethasone, cladribin, prednisone, 131I-chTNT, abiraterone, aclarubicin, alitretinoin, bisantrene, calcium folinate, calcium levofolinate, capecitabin, carmofur, clodronic acid, romiplostim, crisantaspase, darbepoetin alfa, decitabine, denosumab, dibrospidium chloride, eltrombopag, endostatin, epitiostanol, epoetin alfa, filgrastim, fotemustin, gallium nitrate, gemcitabine, glutoxim, histamine dihydrochloride, hydroxycarbamide, improsulfan, ixabepilone, lanreotide, lentinan, levamisole, lisuride, lonidamine, masoprocol, methyltestosterone, methoxsalen, methyl aminolevulinate, miltefosine, mitoguazone, mitomycin, mitotane, nelarabine, nimotuzumab, nitracrin, omeprazole, palifermin, panitumumab, pegaspargase, PEG epoetin beta (methoxy-PEG epoetin beta), pegfilgrastim, peg interferon alfa-2b, pentazocine, pentostatin, perfosfamide, pirarubicin, plicamycin, poliglusam, porfimer sodium, pralatrexate, quinagolide, razoxane, sizofirane, sobuzoxan, sodium glycididazole, tamibarotene, the combination of tegafur and gimeracil and oteracil, testosterone, tetrofosmin, thalidomide, thymalfasin, trabectedin, tretinoin, trilostane, tryptophan, ubenimex, vapreotide, yttrium-90 glass microspheres, zinostatin, zinostatin stimalamer.

Also suitable for tumour therapy is a combination of a non-drug therapy such as chemotherapy (e.g. azacitidine, belotecan, enocitabine, melphalan, valrubicin, vinflunin, zorubicin), radiotherapy (e.g. 1-125 seeds, palladium-103 seed, radium-223 chloride) or phototherapy (e.g. temoporfin, talaporfin) which is accompanied by a drug treatment with the inventive IRAK4 inhibitors or which, after the non-drug tumour therapy such as chemotherapy, radiotherapy or phototherapy has ended, are supplemented by a drug treatment with the inventive IRAK4 inhibitors.

In addition to those mentioned above, the inventive IRAK4 inhibitors can also be combined with the following active ingredients:

active ingredients for Alzheimer's therapy, for example acetylcholinesterase inhibitors (e.g. donepezil, rivastigmine, galantamine, tacrine), NMDA (N-methyl-D-aspartate) receptor antagonists (e.g. memantine); L-DOPA/carbidopa (L-3,4-dihydroxyphenylalanine), COMT (catechol-O-methyltransferase) inhibitors (e.g. entacapone), dopamine agonists (e.g. ropinirole, pramipexole, bromocriptine), MAO-B (monoaminooxidase-B) inhibitors (e.g. selegiline), anticholinergics (e.g. trihexyphenidyl) and NMDA antagonists (e.g. amantadine) for treatment of Parkinson's; beta-interferon (IFN-beta) (e.g. IFN beta-1b, IFN beta-1a Avonex® and Betaferon®), glatiramer acetate, immunoglobulins, natalizumab, fingolimod and immunosuppressants such as mitoxantrone, azathioprine and cyclophosphamide for treatment of multiple sclerosis; substances for treatment of pulmonary disorders, for example beta-2-sympathomimetics (e.g. salbutamol), anticholinergics (e.g. glycopyrronium), methylxanthines (e.g. theophylline), leukotriene receptor antagonists (e.g. montelukast), PDE-4 (phosphodiesterase type 4) inhibitors (e.g. roflumilast), methotrexate, IgE antibodies, azathioprine and cyclophosphamide, cortisol-containing preparations; substances for treatment of osteoarthritis such as non-steroidal anti-inflammatory substances (NSAIDs). In addition to the two therapies mentioned, methotrexate and biologics for B-cell and T-cell therapy (e.g. rituximab, abatacept) should be mentioned for rheumatoid disorders, for example rheumatoid arthritis, spondyloarthritis and juvenile idiopathic arthritis. Neurotrophic substances such as acetylcholinesterase inhibitors (e.g. donepezil), MAO (monoaminooxidase) inhibitors (e.g. selegiline), interferons und anticonvulsives (e.g. gabapentin); active ingredients for treatment of cardiovascular disorders such as beta-blockers (e.g. metoprolol), ACE inhibitors (e.g. benazepril), angiotensin receptor blockers (e.g. losartan, valsartan), diuretics (e.g. hydrochlorothiazide), calcium channel blockers (e.g. nifedipine), statins (e.g. simvastatin, fluvastatin); anti-diabetic drugs, for example metformin, glinides (e.g. nateglinide), DPP-4 (dipeptidyl peptidase-4) inhibitors (e.g. linagliptin, saxagliptin, sitagliptin, vildagliptin), SGLT2 (sodium/glucose cotransporter 2) inhibitors/gliflozin (e.g. dapagliflozin, empagliflozin), incretin mimetics (hormone glucose-dependent insulinotropic peptide (GIP) and glucagon-like peptid 1 (GLP-1) analogues/agonists) (e.g. exenatide, liraglutide, lixisenatide), α-glucosidase inhibitors (e.g. acarbose, miglitol, voglibiose) and sulphonylureas (e.g. glibenclamide, tolbutamide), insulin sensitizers (e.g. pioglitazone) and insulin therapy (e.g. NPH insulin, insulin lispro), substances for treatment of hypoglycaemia, for treatment of diabetes and metabolic syndrome. Lipid-lowering drugs, for example fibrates (e.g. bezafibrate, etofibrate, fenofibrate, gemfibrozil), nicotinic acid derivatives (e.g. nicotinic acid/laropiprant), ezetimib, statins (e.g. simvastatin, fluvastatin), anion exchangers (e.g. colestyramine, colestipol, colesevelam). Active ingredients such as mesalazine, sulfasalazine, azathioprine, 6-mercaptopurine or methotrexate, probiotic bacteria (Mutaflor, VSL#3®, *Lactobacillus* GG, *Lactobacillus plantarum, L. acidophilus, L. casei, Bifidobacterium infantis* 35624, *Enterococcus fecium* SF68, *Bifidobacterium longum, Escherichia coli* Nissle 1917), antibiotics, for example ciprofloxacin and metronidazole, anti-diarrhoea drugs, for example loperamide, or laxatives (bisacodyl) for treatment of chronic inflammatory bowel diseases. Immunosuppressants such as glucocorticoids and non-steroidale anti-inflammatory substances (NSAIDs), cortisone, chloroquine, cyclosporine, azathioprine, belimumab, rituximab, cyclophosphamide for treatment of lupus erythematosus. By way of example but not exclusively, calcineurin inhibitors (e.g. tacrolimus and ciclosporin), cell division inhibitors (e.g. azathioprine, mycophenolate mofetil, mycophenolic acid, everolimus or sirolimus), rapamycin, basiliximab, daclizumab, anti-CD3 antibodies, anti-T-lymphocyte globulin/anti-lymphocyte globulin for organ transplants. Vitamin D3 analogues, for example calcipotriol, tacalcitol or calcitriol, salicylic acid, urea, ciclosporine, methotrexate, efalizumab for dermatological disorders.

Mention should also be made of medicaments comprising at least one of the inventive compounds and one or more further active ingredients, especially EP4 inhibitors (prostaglandin E2 receptor 4 inhibitors), P2X3 inhibitors (P2X purinoceptor 3), PTGES inhibitors (prostaglandin E synthase inhibitors) or AKR1C3 inhibitors (aldo-keto reductase family 1 member C3 inhibitors), for treatment and/or prevention of the aforementioned disorders.

The inventive compounds can act systemically and/or locally. For this purpose, they can be administered in a suitable manner, for example by the oral, parenteral, pulmonal, nasal, sublingual, lingual, buccal, rectal, dermal, transdermal or conjunctival route, via the ear or as an implant or stent. The inventive compounds can be administered in administration forms suitable for these administration routes.

Suitable administration forms for oral administration are those which work according to the prior art and release the inventive compounds rapidly and/or in a modified manner and which contain the inventive compounds in crystalline and/or amorphous and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The inventive compounds can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

The present invention further provides medicaments which comprise at least one inventive compound, typically together with one or more inert, nontoxic, pharmaceutically suitable excipients, and the use thereof for the aforementioned purposes.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of the body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

Preparation of the Inventive Compounds

The preparation of the inventive compounds is illustrated by the synthesis schemes which follow.

Starting materials used for synthesis of the inventive compounds are carboxylic acids (Intermediate V3), which are commercially available or can be prepared by routes known from the literature or analogously to routes known from the literature (see, for example, European Journal of Organic Chemistry 2003, 8, 1559-1568, Chemical and Pharmaceutical Bulletin, 1990, 38, 9, 2446-2458, Synthetic Communications 2012, 42, 658-666, Tetrahedron, 2004, 60, 51, 11869-11874) (see, for example, Synthesis Scheme 1). Some carboxylic acids V3 can be prepared proceeding from carboxylic esters (Intermediate V2) by hydrolysis (cf, for example, the reaction of ethyl 6-(hydroxymethyl)pyridine-2-carboxylate with aqueous sodium hydroxide solution in methanol, WO200411328) or—in the case of a tert-butyl ester—by reaction with an acid, for example hydrogen chloride or trifluoroacetic acid (cf., for example, Dalton Transactions, 2014, 43, 19, 7176-7190). The carboxylic acids V3 can also be used in the form of their alkali metal salts. The Intermediates V2 can optionally also be prepared from the Intermediates V1 which bear a chlorine, bromine or iodine as substituent $X^1$ by reaction in a carbon monoxide atmosphere, optionally under elevated pressure, in the presence of a phosphine ligand, for example 1,3-bis(diphenylphosphino)propane, a palladium compound, for example palladium(II) acetate, and a base, for example triethylamine, with addition of ethanol or methanol in a solvent, for example dimethyl sulphoxide (for preparation methods see, for example, WO2012112743, WO 2005082866, Chemical Communications (Cambridge, England), 2003, 15, 1948-1949, WO200661715). The Intermediates V1 are either commercially available or can be prepared by routes known from the literature. Illustrative preparation methods are detailed in WO 2012061926, European Journal of Organic Chemistry, 2002, 2, 327-330, Synthesis, 2004, 10, 1619-1624, Journal of the American Chemical Society, 2013, 135, 32, 12122-12134, Bioorganic and Medicinal Chemistry Letters, 2014, 24, 16, 4039-4043, US2007185058, WO2009117421.

$X^1$ is chlorine, bromine or iodine.

$R^d$ is methyl, ethyl, benzyl or tert-butyl.

$R^4$, $R^5$ are each as defined in the general formula (I).

Methyl 5-amino-1H-indazole-6-carboxylate (Intermediate 2) can be obtained proceeding from methyl 1H-indazole-6-carboxylate (Intermediate 0) according to Synthesis Scheme 2 by nitration and reduction of the nitro group of Intermediate 1 with hydrogen in the presence of palladium on charcoal analogously to WO 2008/001883. For preparation of the Intermediates 3 proceeding from Intermediate 2, it is possible to use various coupling reagents known from the literature (Amino Acids, Peptides and Proteins in Organic Chemistry, Vol. 3—Building Blocks, Catalysis and Coupling Chemistry, Andrew B. Hughes, Wiley, Chapter 12—Peptide-Coupling Reagents, 407-442; Chem. Soc. Rev., 2009, 38, 606). For example, it is possible to use 1-(3-dimethylaminopropyl)-3-ethylcarbodiimide hydrochloride in combination with 1-hydroxy-1H-benzotriazole hydrate (HOBt, WO2012107475; Bioorg. Med. Chem. Lett., 2008, 18, 2093), (1H-benzotriazol-1-yloxy)(dimethylamino)-N,N-dimethylmethaniminium tetrafluoroborate (TBTU, CAS 125700-67-6), (dimethylamino)-N,N-dimethyl(3H-[1,2,3]triazolo[4,5-b]pyridin-3-yloxy)methanaminium hexafluorophosphate (HATU, CAS 148893-10-1), propanephosphonic anhydride (as solution in ethyl acetate or DMF, CAS68957-94-8) or di-1H-imidazol-1-ylmethanone (CDI) as coupling reagents, with addition of a base such as triethylamine or N-ethyl-N-isopropylpropan-2-amine in each case to the reaction mixture. Preference is given to the use of TBTU and N-ethyl-N-isopropylpropan-2-amine in THF.

Synthesis Scheme 1

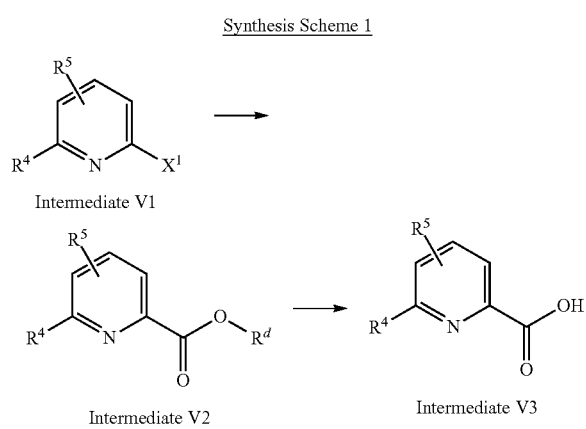

Synthesis Scheme 2

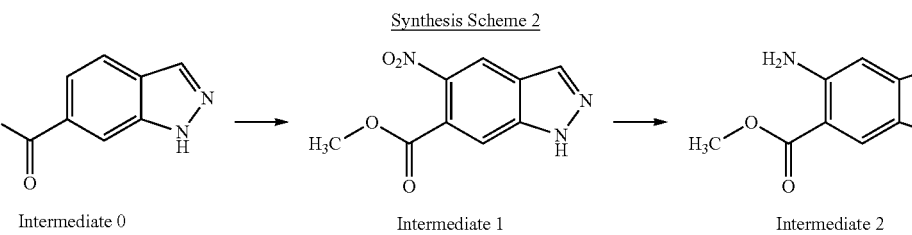

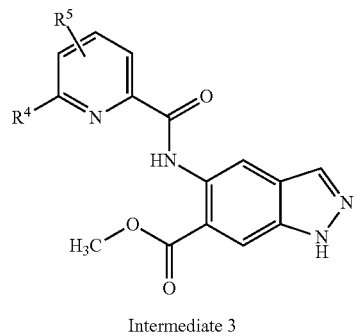

Intermediate 3

The substituents $R^4$, $R^5$ are each as defined in the general formula (I).

Proceeding from the Intermediates 3, it is possible to prepare 2-substituted indazole derivatives (Intermediate 4) (see synthesis scheme 3). Useful reactions for this purpose include those with optionally substituted alkyl chlorides, alkyl bromides, alkyl iodides or alkyl 4-methylbenzenesulphonates. The alkyl halides or alkyl 4-methylbenzenesulphonates used are commercially available or can be prepared analogously to routes known from literature (for the preparation of alkyl 4-methylbenzenesulphonates, one example is the reaction of an appropriate alcohol with 4-methylbenzenesulphonyl chloride in the presence of triethylamine or pyridine; see, for example, Bioorganic and Medicinal Chemistry, 2006, 14, 12 4277-4294). Optionally, in the case of use of alkyl chlorides or alkyl bromides, it is also possible to add an alkali metal iodide such as potassium iodide or sodium iodide. Bases used may, for example, be potassium carbonate, caesium carbonate or sodium hydride. In the case of reactive alkyl halides, it is also possible in some cases to use N-cyclohexyl-N-methylcyclohexanamine. Useful solvents include, for example, 1-methylpyrrolidin-2-one, DMF, DMSO or THF. Optionally, the alkyl halides or alkyl 4-methylbenzenesulphonates used may have functional groups which have optionally been protected with a protecting group beforehand (see also P. G. M. Wuts, T. W. Greene, Greene's Protective Groups in Organic Synthesis, Fourth Edition, ISBN: 9780471697541). If, for example, alkyl halides or alkyl 4-methylbenzenesulphonates having one or more hydroxyl groups are used, these hydroxyl groups may optionally be protected by a tert-butyl(dimethyl)silyl group or a similar silicon-containing protecting group familiar to those skilled in the art. Alternatively, the hydroxyl groups may also be protected by the tetrahydro-2H-pyran (THP) group or by the acetyl or benzoyl group. The protecting groups used can then be detached subsequently to the synthesis of Intermediate 4, or else after the synthesis of (I). If, for example, a tert-butyl(dimethylsilyl) group is used as protecting group, it can be detached using tetrabutylammonium fluoride in a solvent such as THF, for example. A THP protecting group can be detached, for example, using 4-methylbenzenesulphonic acid (optionally in monohydrate form). Acetyl groups or benzoyl groups can be detached by treatment with aqueous sodium hydroxide solution.

Optionally, the alkyl halides or alkyl 4-methylbenzenesulphonates used may contain functional groups which can be converted by oxidation or reduction reactions known to those skilled in the art (see, for example, *Science of Synthesis*, Georg Thieme Verlag). If, for example, the functional group is a sulphide group, this can be oxidized by methods known in the literature to a sulphoxide or sulphone group. In the case of a sulphoxide group, this can likewise be oxidized to a sulphone group.

For these oxidation steps, it is possible to use, for example, 3-chloroperbenzoic acid (CAS 937-14-4) (in this regard, see also, for example, US201094000 for the oxidation of a 2-(methylsulphanyl)ethyl-1H-pyrazole derivative to a 2-(methylsulphinyl)ethyl-1H-pyrazole derivative and the oxidation of a further 2-(methylsulphanyl)ethyl-1H-pyrazole derivative to a 2-(methylsulphonyl)ethyl-1H-pyrazole derivative). If the alkyl halides or tosylates used contain a keto group, this can be reduced by reduction methods known to those skilled in the art to an alcohol group (see, for example, Chemische Berichte, 1980, 113, 1907-1920 for the use of sodium borohydride). These oxidation or reduction steps can be effected subsequently to the synthesis of Intermediate 4, or else after the synthesis of the inventive compounds of the general formula (I). Alternatively, Intermediate 4 can be prepared via Mitsunobu reaction (see, for example, K. C. K. Swamy et. al. Chem. Rev. 2009, 109, 2551-2651) of Intermediate 3 with optionally substituted alkyl alcohols. It is possible to utilize various phosphines such as triphenylphosphine, tributylphosphine or 1,2-diphenylphosphinoethane in combination with diisopropyl azodicarboxylate (CAS 2446-83-5) or further diazene derivatives mentioned in the literature (K. C. K. Swamy et. al. Chem. Rev. 2009, 109, 2551-2651). Preference is given to the use of triphenylphosphine and diisopropyl azodicarboxylate. If the alkyl alcohol bears a functional group it is possible—as in the case of the abovementioned reactions with alkyl halides—for known protecting group strategies (further pointers can be found in P. G. M. Wuts, T. W. Greene, Greene's Protective Groups in Organic Synthesis, Fourth Edition, ISBN: 9780471697541) and—as in the case of the abovementioned reactions with alkyl halides—for oxidation or reduction steps to be effected correspondingly to the synthesis of Intermediate 4, or else after the synthesis of the inventive compounds of the general formula (I). Proceeding from Intermediate 4, inventive compounds of the general formula (I) where $R^2$ and $R^3$ are defined as $C_1$-$C_6$-alkyl (where $R^2$ and $R^3$ have the same definition) may be obtained by a Grignard reaction (cf., for example, the reaction of a methyl 1H-indazole-6-carboxylate derivative with methylmagnesium bromide in EP 2489663). For the Grignard reaction, it is possible to use alkylmagnesium halides. Particular preference is given to methylmagnesium chloride or methylmagnesium bromide in THF or diethyl ether, or else in mixtures of THF and diethyl ether. Alternatively, proceeding from Intermediate 4, inventive compounds of the general formula (I) where $R^2$ and $R^3$ are defined as $C_1$-$C_6$-alkyl (where $R^2$ and $R^3$ have the same definition) may be obtained by a reaction with an alkyllithium reagent (cf, for example, the reaction of a methyl 2-amino-4-chloro-1-methyl-1H-benzimidazole-7-carboxylate derivative with isopropyllithium or tert-butyllithium in WO2006116412). Proceeding from Intermediate 4, it is possible to prepare inventive compounds of the general formula (I) where $R^2$ and $R^3$ are defined as H by reduction with lithium aluminium hydride in THF, lithium borohydride in THF or sodium borohydride in THF, optionally with addition of methanol, or mixtures of lithium borohydride and sodium borohydride.

Synthesis Scheme 3

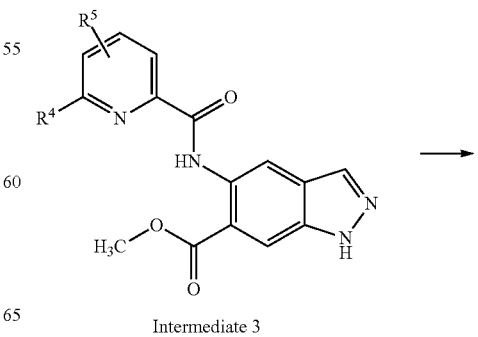

Intermediate 3

-continued

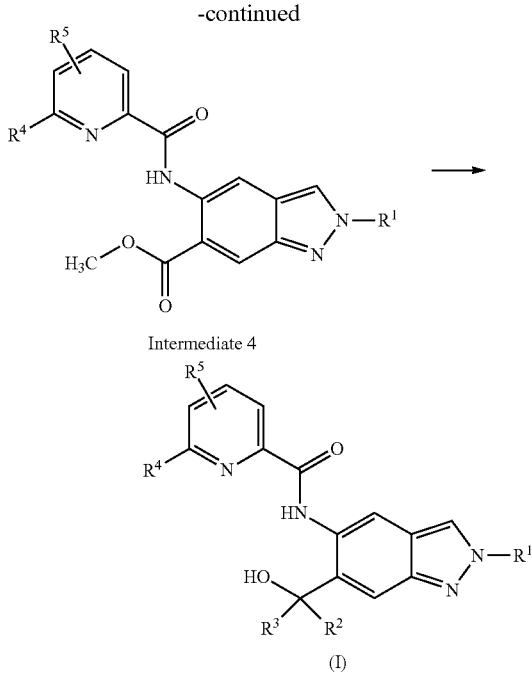

Intermediate 4

(I)

The substituents $R^1$, $R^2$, $R^3$, $R^4$, $R^5$ are each as defined in the general formula (I).

Proceeding from Intermediate 3, Intermediate 5 where $R^2$ and $R^3$ are defined as $C_1$-$C_6$-alkyl (where $R^2$ and $R^3$ have the same definition) may be obtained by a Grignard reaction (cf, for example, Synthesis Scheme 4). For this purpose, it is possible to use suitable alkylmagnesium halides, for example methylmagnesium chloride or methylmagnesium bromide in THF or in diethyl ether or else in mixtures of THF and diethyl ether.

Proceeding from Intermediate 5, it is then possible to prepare a portion (I-a) of the inventive compounds (I) where $R^2$ and $R^3$ are defined as $C_1$-$C_6$-alkyl (where $R^2$ and $R^3$ have the same definition). For this purpose, analogously to Synthesis Scheme 3 (preparation of Intermediate 3), useful reactions are those of Intermediate 5 with optionally substituted alkyl chlorides, alkyl bromides, alkyl iodides or alkyl 4-methylbenzenesulphonates. It is possible to use protecting group strategies analogously to those described in Synthesis Scheme 3.

Alternatively, for preparation of a portion (I-a) of the inventive compounds (I) where $R^2$ and $R^3$ are defined as $C1$-$C_6$-alkyl (where $R^2$ and $R^3$ have the same definition), it is possible to use the Mitsunobu reaction of Intermediate 5 with optionally substituted alkyl alcohols (analogously to Synthesis Scheme 3).

If $R^1$ in the compounds of the formula (I-a) includes a suitable functional group, it is optionally possible subsequently, in analogy to Synthesis Scheme 3, to use oxidation or reduction reactions for preparation of further inventive compounds.

Synthesis Scheme 4

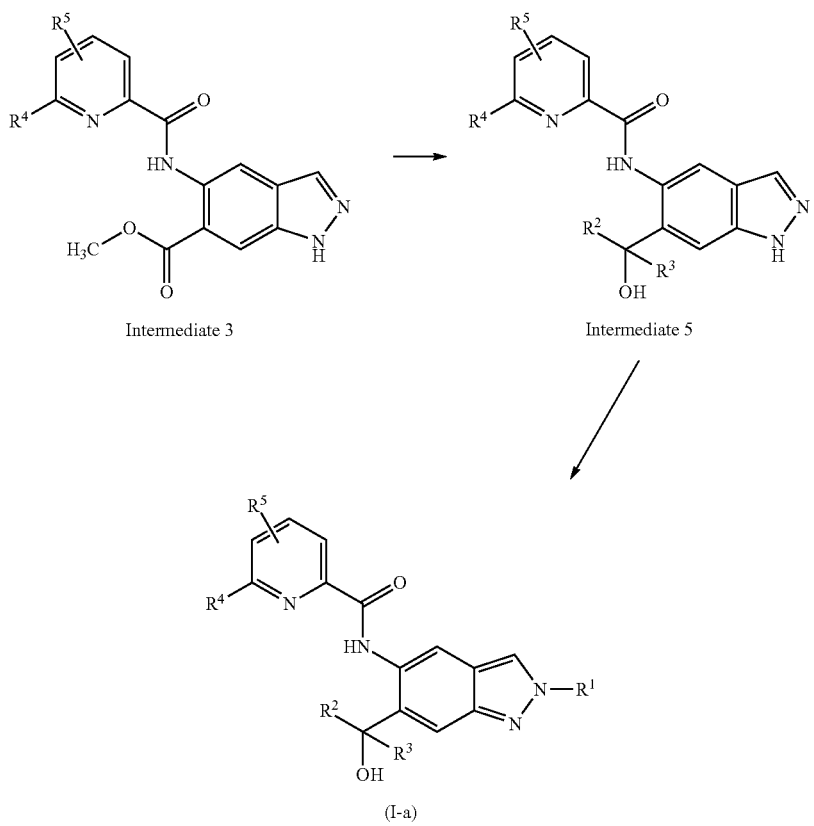

The substituents $R^1$, $R^4$, $R^5$ are each as defined in the general formula (I). $R^2$ and $R^3$ always have the same definition and are both $C_1$-$C_6$-alkyl.

Proceeding from Intermediate 1, it is possible to prepare Intermediate 4 in an alternative manner (see Synthesis Scheme 5). First of all, Intermediate 1 is converted to Intermediate 6 by methods as in Synthesis Scheme 3 (preparation of Intermediate 4 from Intermediate 3).

Intermediate 6 can then be converted to Intermediate 7 by reduction of the nitro group. For example, the nitro group can be reduced with palladium on carbon under a hydrogen atmosphere (cf., for example, WO2013174744 for the reduction of 6-isopropoxy-5-nitro-1H-indazole to 6-isopropoxy-1H-indazol-5-amine) or by the use of iron and ammonium chloride in water and ethanol (see, for example, also Journal of the Chemical Society, 1955, 2412-2419), or by the use of tin(II) chloride (CAS 7772-99-8). The use of iron and ammonium chloride in water and ethanol is preferred. The preparation of Intermediate 4 from Intermediate 7 can be effected analogously to Synthesis Scheme 2 (preparation of Intermediate 3 from Intermediate 2).

As described for Synthesis Scheme 3, it is optionally possible to use protecting group strategies in the case of Synthesis Scheme 5 as well. Optionally, it is additionally possible, proceeding from Intermediate 6 or Intermediate 7, as described for Synthesis Scheme 3, to conduct oxidation or reduction reactions known to those skilled in the art (cf., for example *Science of Synthesis*, Georg Thieme Verlag).

The substituents $R^1$, $R^4$, $R^5$ are each as defined in the general formula (I).

Synthesis of the Example Compounds

Abbreviations and Elucidations

| | |
|---|---|
| DMF | N,N-dimethylformamide |
| DMSO | dimethyl sulphoxide |
| THF | tetrahydrofuran |
| RT | room temperature |
| HPLC | high-performance liquid chromatography |
| h | hour(s) |
| HCOOH | formic acid |
| MeCN | acetonitrile |
| min | minute(s) |
| UPLC | ultrahigh-performance liquid chromatography |
| DAD | diode array detector |
| ELSD | evaporating light scattering detector |
| ESI | electrospray ionization |
| SQD | single quadrupole detector |
| CPG | core-pulled precision glass |
| $NH_3$ | ammonia |

The term sodium chloride solution always means a saturated aqueous sodium chloride solution.

The chemical names of the intermediates and examples were generated using the ACD/LABS (Batch Version 12.01) software.

Synthesis Scheme 5

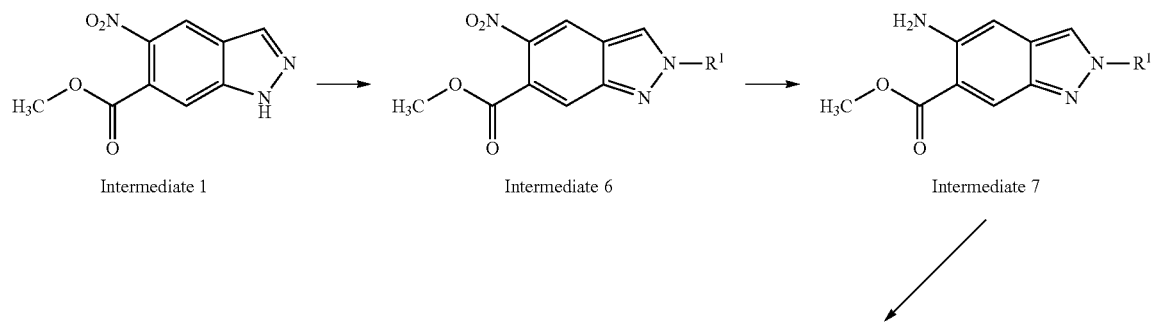

Intermediate 1     Intermediate 6     Intermediate 7

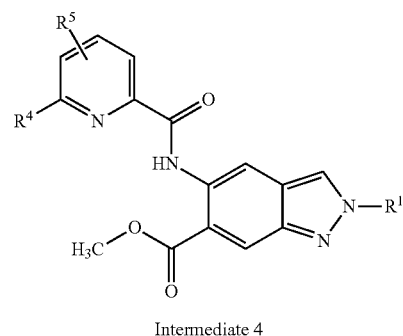

Intermediate 4

Methods

In some cases, the inventive compounds and precursors and/or intermediates thereof were analysed by LC-MS.

Method A1: UPLC (MeCN—HCOOH):

Instrument: Waters Acquity UPLC-MS SQD 3001; column: Acquity UPLC BEH C18 1.7 50×2.1 mm; eluent A: water+0.1% by vol. of formic acid (99%), eluent B: acetonitrile; gradient: 0-1.6 min 1-99% B, 1.6-2.0 min 99% B; flow rate 0.8 ml/min; temperature: 60° C.; injection: 2 µl; DAD scan: 210-400 n; MS ESI+, ESI−, scan range 160-1000 m/z; ELSD.

Method A2: UPLC (MeCN—NH$_3$):

Instrument: Waters Acquity UPLC-MS SQD 3001; column: Acquity UPLC BEH C18 1.7 50×2.1 mm; eluent A: water+0.2% by vol. of ammonia (32%), eluent B: acetonitrile; gradient: 0-1.6 min 1-99% B, 1.6-2.0 min 99% B; flow rate 0.8 ml/min; temperature: 60° C.; injection: 2 µl; DAD scan: 210-400 n; MS ESI+, ESI−, scan range 160-1000 m/z; ELSD.

Method A3: (LC-MS)

Instrument: Agilent 1290 Infinity LC; column: Acquity UPLC BEH C18 1.7 50×2.1 mm; eluent A: water+0.05% by vol. of formic acid, eluent B: acetonitrile+0.05% by vol. of formic acid; gradient: 0-1.7 min 2-90% B, 1.7-2.0 min 90% B; flow rate 1.2 ml/min; temperature: 60° C.; injection: 2 µl; DAD scan: 190-390 nm; MS: Agilent TOF 6230.

Method A4: (LC-MS)

Instrument: Waters Acquity; column: Kinetex (Phenomenex), 50×2 mm; eluent A: water+0.05% by vol. of formic acid, eluent B: acetonitrile+0.05% by vol. of formic acid; gradient: 0-1.9 min 1-99% B, 1.9-2.1 min 99% B; flow rate 1.5 ml/min; temperature: 60° C.; injection: 0.5 µl; DAD scan: 200-400 nm.

In some cases, the inventive compounds and the precursors and/or intermediates thereof were purified by the following illustrative preparative HPLC methods:

Method P1: system: Waters Autopurification system: Pump 2545, Sample Manager 2767, CFO, DAD 2996, ELSD 2424, SQD; column: XBridge C18 5 µm 100×30 mm; eluent A: water+0.1% by vol. of formic acid, eluent B: acetonitrile; gradient: 0-8 min 10-100% B, 8-10 min 100% B; flow: 50 ml/min; temperature: room temperature; solution: max. 250 mg/max. 2.5 ml DMSO or DMF; injection: 1×2.5 ml; detection: DAD scan range 210-400 nm; MS ESI+, ESI−, scan range 160-1000 m/z.

Method P2: system: Waters Autopurification system: Pump 254, Sample Manager 2767, CFO, DAD 2996, ELSD 2424, SQD 3100; column: XBridge C18 5 µm 10×30 mm; eluent A: water+0.2% by vol. of ammonia (32%), eluent B: methanol; gradient: 0-8 min 30-70% B; flow: 50 ml/min; temperature: room temperature; detection: DAD scan range 210-400 nm; MS ESI+, ESI−, scan range 160-1000 m/z; ELSD.

Method P3: system: Labomatic, pump: HD-5000, fraction collector: LABOCOL Vario-4000, UV detector: Knauer UVD 2.1S; column: XBridge C18 5 µm 100×30 mm; eluent A: water+0.2% by vol. of ammonia (25%), eluent B: acetonitrile; gradient: 0-1 min 15% B, 1-6.3 min 15-55% B, 6.3-6.4 min 55-100% B, 6.4-7.4 min 100% B; flow: 60 ml/min; temperature: room temperature; solution: max. 250 mg/2 ml DMSO; injection: 2×2 ml; detection: UV 218 n; Software: SCPA PrepCon5.

Method P4: system: Labomatic, pump: HD-5000, fraction collector: LABOCOL Vario-4000, UV detector: Knauer UVD 2.1S; column: Chromatorex RP C18 10 µm 125×30 mm; eluent A: water+0.1% by vol. of formic acid, eluent B: acetonitrile; gradient: 0-15 min 65-100% B; flow: 60 ml/min; temperature: room temperature; solution: max. 250 mg/2 ml DMSO; injection: 2×2 ml; detection: UV 254 nm; Software: SCPA PrepCon5.

Method P5: system: Sepiatec: Prep SFC100, column: Chiralpak IA 5 µm 250×20 mm; eluent A: carbon dioxide, eluent B: ethanol; gradient: isocratic 20% B; flow: 80 ml/min; temperature: 40° C.; solution: max. 250 mg/2 ml DMSO; injection: 5×0.4 mL; detection: UV 254 n.

Method P6: system: Agilent: Prep 1200, 2× prep pump, DLA, MWD, Gilson: Liquid Handler 215; column: Chiralcel OJ-H 5 µm 250×20 mm; eluent A: hexane, eluent B: ethanol; gradient: isocratic 30% B; flow: 25 ml/min; temperature: 25° C.; solution: 187 mg/8 ml ethanol/methanol; injection: 8×1.0 ml; detection: UV 280 nm.

Method P7: system: Labomatic, pump: HD-5000, fraction collector: LABOCOL Vario-4000, UV detector: Knauer UVD 2.1S; column: XBridge C18 5 µm 100×30 mm; eluent A: water+0.1% by vol. of formic acid, eluent B: acetonitrile; gradient: 0-3 min: 65% B isocratic, 3-13 min: 65-100% B; flow: 60 ml/min; temperature: room temperature; solution: max. 250 mg/2 ml DMSO; injection: 2×2 ml; detection: UV 254 nm.

Method P8: system: Agilent: Prep 1200, 2× prep pump, DLA, MWD, Gilson: Liquid Handler 215; column: Chiralpak IF 5 µm 250×20 mm; eluent A: ethanol, eluent B: methanol; gradient: isocratic 50% B; flow: 25 ml/min; temperature: 25° C.; solution: 600 mg/7 ml N,N-dimethylformamide; injection: 10×0.7 ml; detection: UV 254 nm.

In some cases, substance mixtures were purified by column chromatography on silica gel.

For preparation of some of the inventive compounds and the precursors and/or intermediates thereof, a column chromatography purification ("flash chromatography") was conducted on silica gel using Isolera® devices from Biotage. This was done using cartridges from Biotage, for example the "SNAP Cartridge, KP_SIL" cartridge of different size and "Interchim Puriflash Silica HP 15UM flash column" cartridges from Interchim of different size.

Starting Materials

Intermediate V2-1

Methyl 6-(2-hydroxypropan-2-yl)pyridine-2-carboxylate

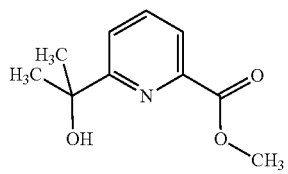

2.00 g (9.26 mmol) of 2-(6-bromopyridin-2-yl)propan-2-ol (CAS 638218-78-7) were dissolved in ml of methanol and 20 ml of DMSO. Subsequently, 250 mg of 1,3-bis(diphenylphosphino)propane, 130 mg of palladium(II) acetate and 3 ml of triethylamine were added. The reaction mixture was purged three times with carbon monoxide at room temperature and stirred under a 13 bar carbon monoxide atmosphere for 30 min. The carbon monoxide atmosphere was removed by applying a vacuum and the mixture was stirred under a 14 bar carbon monoxide atmosphere at 100° C. for 24 h. The autoclave was decompressed, water was added to the reaction mixture, and the reaction mixture was extracted three times with ethyl acetate, washed with saturated aqueous sodium hydrogencarbonate solution and sodium chloride solution, filtered through a hydrophobic filter and concentrated. This gave 1.60 g of a crude product.

UPLC-MS (Method A1): $R_t$=0.76 min (UV detector: TIC), mass found 195.00.

Intermediate V3-1

Potassium 6-(2-hydroxypropan-2-yl)pyridine-2-carboxylate

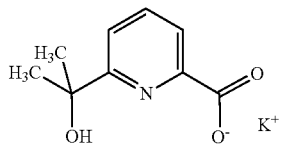

1.60 g of the crude product of Intermediate 0-1 were initially charged in 15 ml of methanol, 0.74 g of potassium hydroxide was added and the mixture was stirred at 50° C. for 16.5 h. After concentration, this gave 2.1 g of a residue which was used without further purification.

UPLC-MS (Method A1): $R_t$=0.47 min (UV detector: TIC), mass found 181.00.

Intermediate 1-1

Methyl 5-nitro-1H-indazole-6-carboxylate

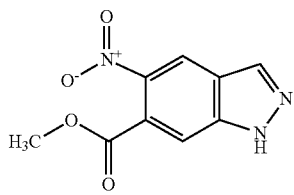 [SMILES: COC(=O)c1cc2[nH]ncc2cc1[N+](=O)[O-]]

4.60 g (26.1 mmol) of methyl 1H-indazole-6-carboxylate (CAS No: 170487-40-8) were dissolved in 120 ml of sulphuric acid (96%) and cooled to −15° C. in a three-neck flask having a CPG stirrer, dropping funnel and internal thermometer. Over a period of 15 min, the nitrating acid (10 ml of 96% sulphuric acid in 5 ml of 65% nitric acid), which had been prepared and cooled beforehand, was added dropwise to this solution. After the dropwise addition had ended, the mixture was stirred for a further 1 h (internal temperature at −13° C.). The reaction mixture was added to ice, and the precipitate was filtered off with suction, washed with water and dried in a drying cabinet at 50° C. under reduced pressure. 5.49 g of the title compound were obtained.

UPLC-MS (Method A2): $R_t$=0.75 min

MS (ESIpos): m/z=222 (M+H)$^+$ $^1$H NMR (400 MHz, DMSO-d6): δ [ppm]=3.87 (s, 3H), 7.96 (s, 1H), 8.44 (s, 1H), 8.70 (s, 1H), 13.98 (br. s., 1H).

Intermediate 2-1

Methyl 5-amino-1H-indazole-6-carboxylate

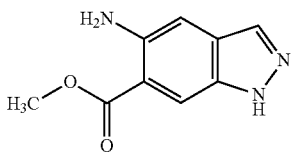

4.40 g (19.8 mmol) of methyl 5-nitro-1H-indazole-6-carboxylate (Intermediate 1-1) were dissolved in 236 ml of methanol and hydrogenated with 1.06 g (0.99 mmol) of palladium on activated carbon under standard hydrogen pressure at 25° C. for 3 h. The reaction mixture was filtered through Celite, the filter was washed with methanol, and the filtrate was concentrated. 3.53 g of the title compound were obtained.

$^1$H NMR (300 MHz, DMSO-d6): δ [ppm]=3.85 (s, 3H) 6.01 (s, 2H) 6.98 (s, 1H) 7.79-7.91 (m, 1H) 7.99 (s, 1H) 12.84 (br. s., 1H).

Intermediate 3-1

Methyl 5-({[6-(trifluoromethyl)pyridin-2-yl]carbonyl}amino)-1H-indazole-6-carboxylate

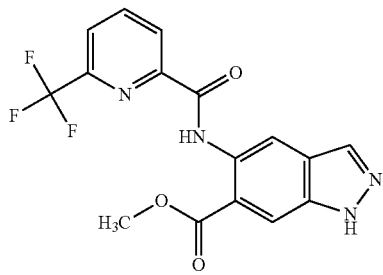 [SMILES: COC(=O)c1cc2[nH]ncc2cc1NC(=O)c1cccc(C(F)(F)F)n1]

4.95 g (25.9 mmol) of 6-(trifluoromethyl)pyridine-2-carboxylic acid were initially charged in 45 ml of THF. 9.07 g (28.2 mmol) of O-(benzotriazol-1-yl)-N,N,N',N'-tetramethyluronium tetrafluoroborate and 4.92 ml (28.2 mmol) of N-ethyl-N-isopropylpropan-2-amine were added and the mixture was stirred at 25° C. for 30 min. Subsequently, 4.50 g (23.5 mmol) of methyl 5-amino-1H-indazole-6-carboxylate (Intermediate 2-1) were added and the mixture was stirred at 25° C. for 24 h. The reaction mixture was filtered with suction through a membrane filter and the solids were washed with THF and with water, and dried in a drying cabinet overnight. 7.60 g of the title compound were obtained.

UPLC-MS (Method A2): $R_t$=1.16 min

MS (ESIpos): m/z=365 (M+H)$^+$ $^1$H NMR (400 MHz, DMSO-d6): δ [ppm]=3.97 (s, 3H), 8.13-8.27 (m, 2H), 8.30 (s, 1H), 8.33-8.45 (m, 1H), 8.45-8.51 (m, 1H), 9.15 (s, 1H), 12.57 (s, 1H), 13.44 (s, 1H).

Intermediate 3-2

Methyl 5-({1[6-(difluoromethyl)pyridin-2-yl]carbonyl}amino)-1H-indazole-6-carboxylate

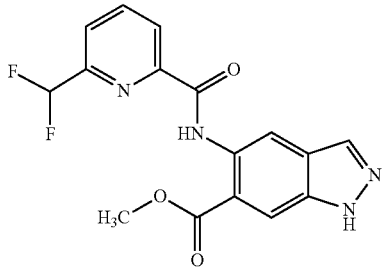 [SMILES: COC(=O)c1cc2[nH]ncc2cc1NC(=O)c1cccc(C(F)F)n1]

2.85 g (23.5 mmol) of 6-(difluoromethyl)pyridine-2-carboxylic acid were initially charged in 30 ml of THF. 6.05 g (18.8 mmol) of O-(benzotriazol-1-yl)-N,N,N',N'-tetramethyluronium tetrafluoroborate and 3.3 ml of N-ethyl-N-isopropylpropan-2-amine were added and the mixture was stirred at room temperature for 10 minutes. Subsequently, 3.00 g (15.7 mmol) of methyl 5-amino-1H-indazole-6-carboxylate were added and the mixture was stirred at room temperature overnight. The reaction mixture was admixed with water, and the precipitate was filtered off with suction and washed repeatedly with water and dichloromethane. This gave 1.53 g (27% of theory) of the title compound. The phases of the filtrate were separated, the organic phase was concentrated, admixed with a little dichloromethane and suspended in an ultrasound bath, and the precipitate was filtered off with suction. This gave a further 1.03 g of the title compound.

1H-NMR (first product fraction, 300 MHz, DMSO-d6): δ [ppm]=3.99 (s, 3H), 7.09 (t, 1H), 8.00 (d, 1H), 8.21-8.40 (m, 4H), 9.14 (s, 1H), 12.53 (s, 1H), 13.44 (s, 1H).

Intermediate 3-3

Methyl 5-({[6-(2-hydroxypropan-2-yl)pyridin-2-yl]carbonyl}amino)-1H-indazole-6-carboxylate

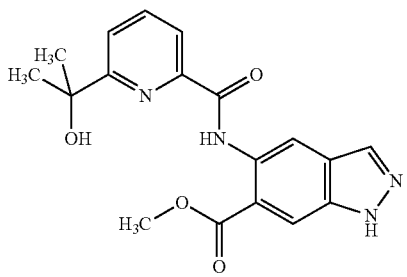 [SMILES: COC(=O)c1cc2[nH]ncc2cc1NC(=O)c1cccc(C(C)(C)O)n1]

2.10 g of potassium 6-(2-hydroxypropan-2-yl)pyridine-2-carboxylate (Intermediate V3-1) were initially charged in 15 ml of THF. 3.69 g (11.5 mmol) of O-(benzotriazol-1-yl)-N,N,N',N'-tetramethyluronium tetrafluoroborate and 2.00 ml of N-ethyl-N-isopropylpropan-2-amine were added and the mixture was stirred at room temperature for 15 min. Subsequently, 1.83 g (9.58 mmol) of methyl 5-amino-1H-indazole-6-carboxylate (Intermediate 2-1) were added and the mixture was stirred at room temperature for 19 h. The mixture was admixed with water and ethyl acetate, the undissolved solids were filtered off, the phases of the filtrate were separated, and the aqueous phase was extracted twice with ethyl acetate, washed with sodium chloride solution, filtered through a hydrophobic filter, concentrated and purified by column chromatography on silica gel (hexane/ethyl acetate). After the solvents had been removed, 1.56 g of the title compound were obtained as a yellow foam.

UPLC-MS (Method A1): $R_t$=1.00 min (UV detector: TIC Smooth), mass found 354.00.

1H-NMR (500 MHz, DMSO-d6): δ [ppm]=1.63 (s, 6H), 3.97 (s, 3H), 5.37 (s, 1H), 7.90-7.95 (m, 1H), 8.03-8.07 (m, 2H), 8.23 (s, 1H), 8.29 (s, 1H), 9.19 (s, 1H), 12.79 (s, 1H), 13.41 (br.s., 1H).

Intermediate 4-1

Methyl 2-(oxetan-3-ylmethyl)-5-({[6-(trifluoromethyl)pyridin-2-yl]carbonyl}amino)-2H-indazole-6-carboxylate

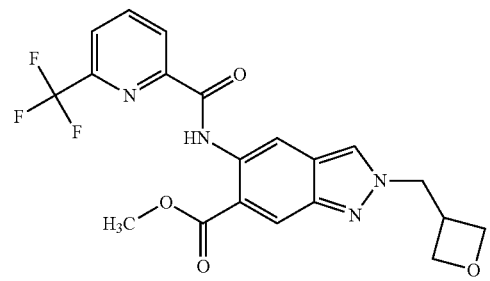 [SMILES: COC(=O)c1cc2nn(CC3COC3)cc2cc1NC(=O)c1cccc(C(F)(F)F)n1]

1.00 g (2.66 mmol) of methyl 5-({[6-(trifluoromethyl)pyridin-2-yl]carbonyl}amino)-1H-indazole-6-carboxylate (Intermediate 3-1) was dissolved in 10 ml of DMF and, after addition of 1.10 g (7.99 mmol) of potassium carbonate and 221 mg (1.33 mmol) of potassium iodide, the mixture was stirred at 25° C. for 30 min. 603 mg (3.99 mmol) of 3-bromomethyloxetane were added, and the mixture was stirred at 25° C. for 24 h. The reaction mixture was partitioned between water and ethyl acetate. The mixture was extracted twice with ethyl acetate, and the combined organic phases were filtered through a hydrophobic filter and concentrated. The residue was purified by column chromatography on silica gel (hexane/ethyl acetate). 260 mg of the title compound were obtained.

UPLC-MS (Method A2): $R_t$=1.24 min

MS (ESIpos): m/z=435 (M+H)⁺

¹H NMR (400 MHz, DMSO-d6): δ [ppm]=3.49-3.64 (m, 1H), 3.95 (s, 3H), 4.49 (t, 2H), 4.68 (dd, 2H), 4.81 (d, 2H), 8.20 (dd, 1H), 8.35-8.41 (m, 1H), 8.43-8.49 (m, 2H), 8.55-8.58 (m, 1H), 9.06 (s, 1H), 12.53 (s, 1H).

Intermediate 4-2

Methyl 2-(2-methoxyethyl)-5-({[6-(trifluoromethyl)pyridin-2-yl]carbonyl}amino)-2H-indazole-6-carboxylate

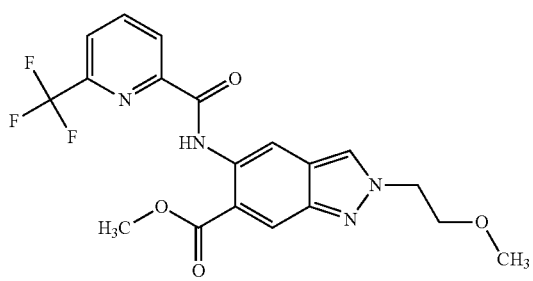 [SMILES: COCCn1cc2cc(NC(=O)c3cccc(C(F)(F)F)n3)c(C(=O)OC)cc2n1]

1.00 g (2.75 mmol) of methyl 5-({[6-(trifluoromethyl)pyridin-2-yl]carbonyl}amino)-1H-indazole-6-carboxylate (Intermediate 3-1) was dissolved in 5 ml of DMF, and 387 µl (4.12 mmol) of 2-bromoethyl methyl ether, 1.14 g (8.23 mmol) of potassium carbonate and 228 mg (1.37 mmol) of potassium iodide were added while stirring. The reaction mixture was stirred at 25° C. for 24 h, diluted with water and extracted twice with ethyl acetate. The combined organic phases were filtered through a hydrophobic filter and concentrated. The residue was purified by column chromatography on silica gel (hexane/ethyl acetate). 12 mg of the title compound were obtained.

UPLC-MS (Method A1): $R_t$=1.24 min
MS (ESIpos): m/z=423 (M+H)$^+$
$^1$H NMR (400 MHz, DMSO-d6): δ [ppm]=3.24 (s, 3H), 3.86 (t, 2H), 3.96 (s, 3H), 4.65 (t, 2H), 8.21 (dd, 1H), 8.35-8.42 (m, 1H), 8.43-8.51 (m, 2H), 8.52 (d, 1H), 9.06 (s, 1H), 12.53 (s, 1H).

Intermediate 4-3

Methyl 2-(3-methoxypropyl)-5-({[6-(trifluoromethyl)pyridin-2-yl]carbonyl}amino)-2H-indazole-6-carboxylate

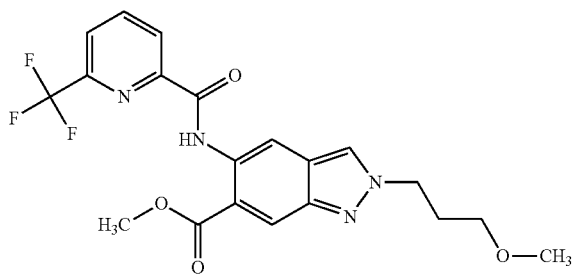 [SMILES: COCCCn1cc2cc(NC(=O)c3cccc(C(F)(F)F)n3)c(C(=O)OC)cc2n1]

1.00 g (2.75 mmol) of methyl 5-({[6-(trifluoromethyl)pyridin-2-yl]carbonyl}amino)-1H-indazole-6-carboxylate (Intermediate 3-1) was dissolved in 5 ml of DMF, and 460 µl (4.12 mmol) of 1-bromo-3-methoxypropane, 1.14 g (8.23 mmol) of potassium carbonate and 228 mg (1.37 mmol) of potassium iodide were added while stirring. The reaction mixture was stirred at 25° C. for 72 h, diluted with water and extracted twice with ethyl acetate. The combined organic phases were filtered through a hydrophobic filter and concentrated. The residue was purified by column chromatography on silica gel (hexane/ethyl acetate). 28 mg of the title compound were obtained.

UPLC-MS (Method A1): $R_t$=1.29 min
MS (ESIpos): m/z=437 (M+H)$^+$
$^1$H NMR (400 MHz, DMSO-d6): δ [ppm]=2.17 (quin, 2H), 3.24 (s, 3H), 3.33-3.36 (m, 2H), 3.96 (s, 3H), 4.53 (t, 2H), 8.21 (dd, 1H), 8.35-8.42 (m, 1H), 8.45-8.49 (m, 2H), 8.54 (d, 1H), 9.06 (s, 1H), 12.54 (s, 1H).

Intermediate 4-4

Methyl 2-(3-hydroxy-3-methylbutyl)-5-({[6-(trifluoromethyl)pyridin-2-yl]carbonyl}amino)-2H-indazole-6-carboxylate Preparation Method 1

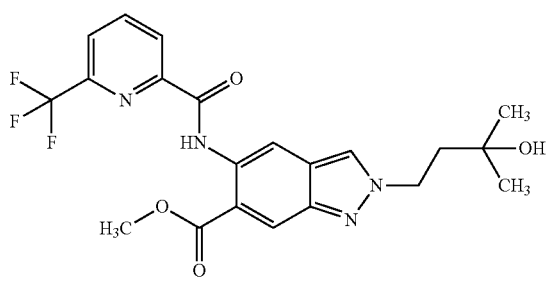 [SMILES: COC(=O)c1cc2nn(CCC(C)(C)O)cc2cc1NC(=O)c1cccc(C(F)(F)F)n1]

930 mg (2.55 mmol) of methyl 5-({[6-(trifluoromethyl)pyridin-2-yl]carbonyl}amino)-1H-indazole-6-carboxylate (Intermediate 3-1), 1.06 g of potassium carbonate and 212 mg of potassium iodide were initially charged in 9 ml of DMF and the mixture was stirred for 15 min. Then 0.62 ml of 4-bromo-2-methylbutan-2-ol was added and the mixture was stirred at 60° C. for 16 h. The mixture was admixed with water and extracted twice with ethyl acetate, and the extract was washed three times with saturated sodium chloride solution, filtered and concentrated. Column chromatography purification on silica gel (hexane/ethyl acetate) gave 424 mg of the title compound.

UPLC-MS (Method A2): $R_t$=1.21 min (UV detector: TIC), mass found 450.00.
$^1$H-NMR (400 MHz, DMSO-d$_6$): δ [ppm]=1.16 (s, 6H) 2.02-2.11 (m, 2H) 3.96 (s, 3H) 4.51-4.60 (m, 3H) 8.20 (dd, J=7.83, 1.01 Hz, 1H) 8.39 (s, 1H) 8.45 (s, 2H) 8.55 (d, J=0.76 Hz, 1H) 9.05 (s, 1H) 12.52 (s, 1H)

Preparation Method 2

1.95 g (7.03 mmol) of methyl 5-amino-2-(3-hydroxy-3-methylbutyl)-2H-indazole-6-carboxylate (Intermediate 7-1) were initially charged in 30 ml of THF. 1.48 g (7.73 mmol) of 6-(trifluoromethyl)pyridine-2-carboxylic acid, 2.71 g (8.44 mmol) of O-(benzotriazol-1-yl)-N,N,N',N'-tetramethyluronium tetrafluoroborate and 1.47 ml (8.44 mmol) of N-ethyl-N-isopropylpropan-2-amine were added and the mixture was stirred at 25° C. for 20.5 h. Water was added, the mixture was extracted three times with ethyl acetate and the extracts were washed with sodium chloride solution, filtered through a hydrophobic filter and concentrated. The residue was separated by column chromatography on silica gel (hexane/ethyl acetate gradient). 2.79 g of the title compound were obtained.

UPLC-MS (Method A1): $R_t$=1.23 min (UV detector: TIC), mass found 450.00.

Intermediate 4-5

Methyl 2-(2-{[tert-butyl(dimethyl)silyl]oxy}ethyl)-5-({[6-(trifluoromethyl)pyridin-2-yl]carbonyl}amino)-2H-indazole-6-carboxylate

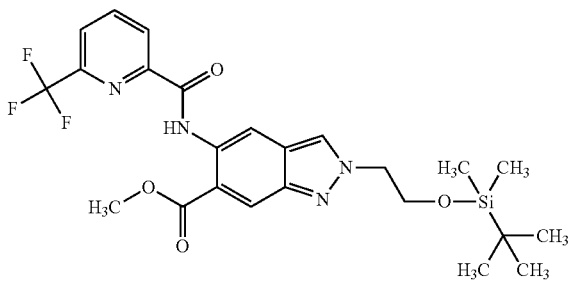 [SMILES: COC(=O)c1cc2nn(CCO[Si](C)(C)C(C)(C)C)cc2cc1NC(=O)c1cccc(C(F)(F)F)n1]

1.00 g (2.66 mmol, 97%) of methyl 5-({[6-(trifluoromethyl)pyridin-2-yl]carbonyl}amino)-1H-indazole-6-carboxylate (Intermediate 3-1) was initially charged in 50 ml of DMF, 1.10 g (7.99 mmol) of potassium carbonate and 221 mg (1.33 mmol) of potassium iodide were added while stirring, and the mixture was stirred at 25° C. for 30 min. Subsequently, 857 µl (3.99 mmol) of (2-bromoethoxy)(tert-butyl)dimethylsilane were added and the mixture was stirred at 25° C. for 24 h. The reaction mixture was diluted with water and extracted with ethyl acetate. The combined organic phases were filtered through a hydrophobic filter and concentrated. The residue was purified by column chromatography on silica gel (hexane/ethyl acetate). 400 mg of the title compound were obtained.

UPLC-MS (Method A1): $R_t$=1.58 min

MS (ESIpos): m/z=523 (M+H)$^+$ $^1$H NMR (300 MHz, DMSO-d6): δ [ppm]=−0.18-0.13 (m, 6H), 0.74 (s, 9H), 3.96 (s, 3H), 4.08 (t, 2H), 4.57 (t, 2H), 8.15-8.25 (m, 1H), 8.32-8.43 (m, 1H), 8.43-8.52 (m, 3H), 9.07 (s, 1H), 12.53 (s, 1H).

Intermediate 4-6

Methyl 2-(3-{[tert-butyl(dimethyl)silyl]oxy}propyl)-5-({[6-(trifluoromethyl)pyridin-2-yl]carbonyl}amino)-2H-indazole-6-carboxylate

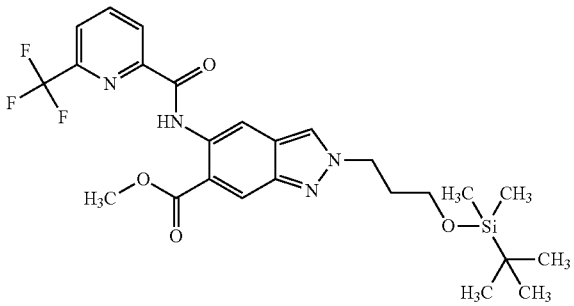 [SMILES: COC(=O)c1cc2nn(CCCO[Si](C)(C)C(C)(C)C)cc2cc1NC(=O)c1cccc(C(F)(F)F)n1]

Analogously to Intermediate 4-5, 1.00 g (2.75 mmol) of methyl 5-({[6-(trifluoromethyl)pyridin-2-yl]carbonyl}amino)-1H-indazole-6-carboxylate (Intermediate 3-1) was dissolved in 10 ml of DMF, 1.14 g (8.24 mmol) of potassium carbonate and 228 mg (1.37 mmol) of potassium iodide were added while stirring, and the mixture was stirred at 25° C. for 30 min. Subsequently, 1.04 g (4.12 mmol) of (3-bromopropoxy)(tert-butyl)dimethylsilane were added and the mixture was stirred at 25° C. for 24 h. The reaction mixture was filtered and the filtercake was washed with ethyl acetate. The reaction mixture was partitioned between water and ethyl acetate and the aqueous phase was extracted twice with ethyl acetate. The combined organic phases were filtered through a hydrophobic filter and concentrated. Purification of the residue by preparative HPLC gave 428 mg of the title compound.

UPLC-MS (Method A1): $R_t$=1.63 min

MS (ESIpos): m/z=537 (M+H)$^+$ $^1$H NMR (400 MHz, DMSO-d6): δ [ppm]=−0.02-0.06 (m, 6H), 0.87 (s, 9H), 2.14 (quin, 2H), 3.62 (t, 2H), 3.96 (s, 3H), 4.54 (t, 2H), 8.20 (d, 1H), 8.35-8.42 (m, 1H), 8.43-8.48 (m, 3H), 8.49-8.53 (m, 1H), 9.06 (s, 1H).

Intermediate 4-7

Methyl 5-({[6-(2-hydroxypropan-2-yl)pyridin-2-yl]carbonyl}amino)-2-(4,4,4-trifluorobutyl)-2H-indazole-6-carboxylate

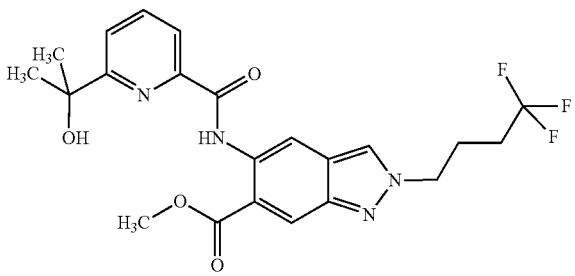 [SMILES: COC(=O)c1cc2nn(CCCC(F)(F)F)cc2cc1NC(=O)c1cccc(C(C)(C)O)n1]

300 mg (0.80 mmol) of methyl 5-({[6-(2-hydroxypropan-2-yl)pyridin-2-yl]carbonyl}amino)-1H-indazole-6-carboxylate (Intermediate 3-3) were initially charged in 4.5 ml of DMF. 287 mg (1.21 mmol) of 1,1,1-trifluoro-4-iodobutane and 333 mg of potassium carbonate were added and the mixture was stirred at 100° C. for 23 h. Water was added, and the mixture was extracted three times with ethyl acetate. The mixture was concentrated and the product was purified by preparative HPLC. This gave 72 mg of the title compound.

UPLC-MS (Method A1): $R_t$=1.26 min (UV detector: TIC), mass found 464.17.

Intermediate 4-8

Methyl 5-{[(5-fluoro-6-methylpyridin-2-yl)carbonyl]amino}-2-(3-hydroxy-3-methylbutyl)-2H-indazole-6-carboxylate

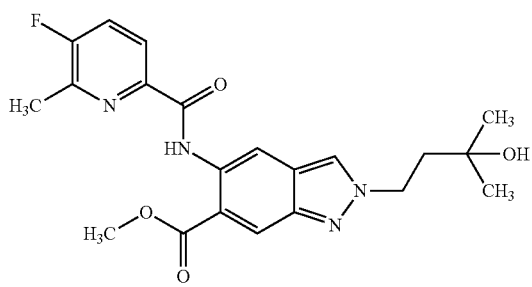 [SMILES: COC(=O)c1cc2nn(CCC(C)(C)O)cc2cc1NC(=O)c1ccc(F)c(C)n1]

195 mg (0.46 mmol) of methyl 5-amino-2-(3-hydroxy-3-methylbutyl)-2H-indazole-6-carboxylate (Intermediate 7-1) were reacted with 78 mg (0.50 mmol) of 5-fluoro-6-methylpyridine-2-carboxylic acid analogous to Intermediate 4-4 (Preparation Method 2) within 19.5 h. 228 mg of a crude product were obtained after analogous aqueous workup.

UPLC-MS (Method A1): $R_t$=1.20 min (UV detector: TIC), mass found 414.00.

Intermediate 4-9

Methyl 2-(3-hydroxy-3-methylbutyl)-5-{[(6-methylpyridin-2-yl)carbonyl]amino}-2H-indazole-6-carboxylate

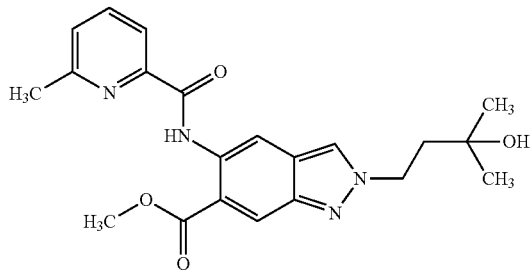 [SMILES: COC(=O)c1cc2nn(CCC(C)(C)O)cc2cc1NC(=O)c1cccc(C)n1]

195 mg (0.45 mmol) of methyl 5-amino-2-(3-hydroxy-3-methylbutyl)-2H-indazole-6-carboxylate (Intermediate 7-1) were reacted with 70 mg (0.50 mmol) of 6-methylpyridine-2-carboxylic acid analogously to preparation of Intermediate 4-4 (Preparation Method 2) within 19.5 h. 278 mg of the title compound as crude product were obtained after analogous aqueous workup.

UPLC-MS (Method A1): $R_t$=1.14 min (UV detector: TIC), mass found 396.00.

Intermediate 4-10

Methyl 2-[3-(2,2,2-trifluoroethoxy)propyl]-5-({[6-(trifluoromethyl)pyridin-2-yl]carbonyl}amino)-2H-indazole-6-carboxylate

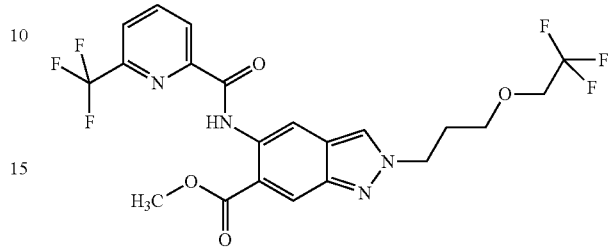

A mixture of 250 mg (0.58 mmol) of methyl 5-({[6-(trifluoromethyl)pyridin-2-yl]carbonyl}amino)-1H-indazole-6-carboxylate (Intermediate 3-1), 193 mg (0.88 mmol) of 3-bromopropyl 2,2,2-trifluoroethyl ether, 242 mg of potassium carbonate and 145 mg of potassium iodide in 3 ml of DMF was stirred at 100° C. for 20 h. Water was added, the mixture was extracted with ethyl acetate and the extract was washed with sodium chloride solution and concentrated. Purification by preparative HPLC gave 52 mg of the title compound.

UPLC-MS (Method A1): $R_t$=1.39 min (UV detector: TIC), mass found 504.12.

Intermediate 4-11

Methyl 5-({[6-(difluoromethyl)pyridin-2-yl]carbonyl}amino)-2-(3-hydroxy-3-methylbutyl)-2H-indazole-6-carboxylate

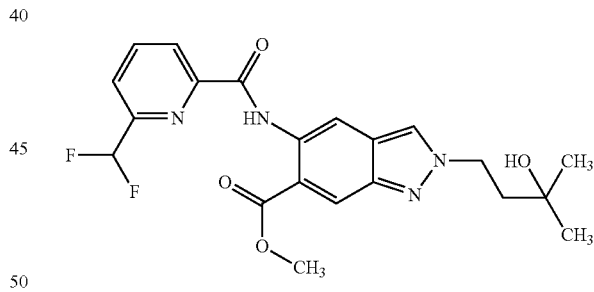

2.00 g of methyl 5-amino-2-(3-hydroxy-3-methylbutyl)-2H-indazole-6-carboxylate (Intermediate 7-1) were initially charged in 40 ml of THF. 1.50 g of 6-(difluoromethyl)pyridine-2-carboxylic acid, 2.78 g of O-(benzotriazol-1-yl)-N,N,N',N'-tetramethyluronium tetrafluoroborate (TBTU, CAS Number 125700-67-6) and 1.5 ml of N-ethyl-N-isopropylpropan-2-amine were added and the mixture was stirred at RT for 24 h. Water was added, the mixture was extracted three times with ethyl acetate, and the combined organic phases were washed with sodium chloride solution and filtered through a hydrophobic filter. The mixture was concentrated and the residue was purified by column chromatography on silica gel (hexane/ethyl acetate). This gave 3.05 g of the title compound as a yellow solid.

UPLC-MS (Method A1): Rt=1.15 min (UV detector TIC), mass found 432.00.

¹H-NMR (400 MHz, DMSO-d₆): δ [ppm]=1.17 (s, 6H), 2.04-2.11 (m, 2H), 3.99 (s, 3H), 4.52-4.60 (m, 3H), 7.10 (t, 1H), 8.00 (dd, 1H), 8.28-8.38 (m, 2H), 8.44-8.47 (m, 1H), 8.56 (d, 1H), 9.05 (s, 1H), 12.49 (s, 1H).

Intermediate 5-1

N-[6-(2-Hydroxypropan-2-yl)-1H-indazol-5-yl]-6-(trifluoromethyl)pyridine-2-carboxamide

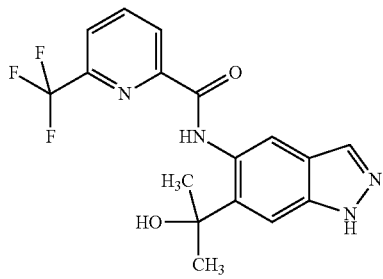 [SMILES: CC(C)(O)c1cc2[nH]ncc2cc1NC(=O)c1cccc(C(F)(F)F)n1]

To a solution, cooled in an ice-water cooling bath, of 1.50 g (4.12 mmol) of methyl 5-({[6-(trifluoromethyl)pyridin-2-yl]carbonyl}amino)-1H-indazole-6-carboxylate (Intermediate 3-1) in 20 ml of THF were cautiously added 6.9 ml (5 equivalents) of a 3M methylmagnesium bromide solution in diethyl ether. The mixture was stirred while cooling with an ice bath for 1 h and at room temperature for 19.5 h. Another 2 equivalents of methylmagnesium bromide solution were added and the mixture was stirred at room temperature for a further 24 h. Saturated aqueous ammonium chloride solution was added and the mixture was stirred and extracted three times with ethyl acetate. The combined organic phases were washed with sodium chloride solution, filtered through a hydrophobic filter and concentrated. The residue was purified by column chromatography on silica gel (hexane/ethyl acetate). 763 mg of the title compound were obtained.

¹H-NMR (400 MHz, DMSO-d₆): δ [ppm]=1.63 (s, 6H), 5.99 (s, 1H), 7.49 (s, 1H), 8.06 (s, 1H), 8.14-8.19 (m, 1H), 8.37 (t, 1H), 8.46 (d, 1H), 8.78 (s, 1H), 12.32 (s, 1H), 12.97 (s, 1H).

Intermediate 5-2

6-(Difluoromethyl)-N-[6-(2-hydroxypropan-2-yl)-1H-indazol-5-yl]pyridine-2-carboxamide

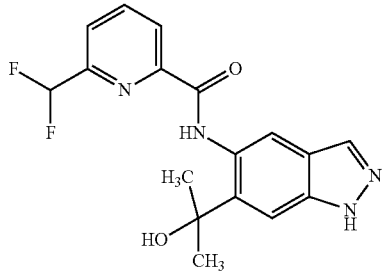 [SMILES: CC(C)(O)c1cc2[nH]ncc2cc1NC(=O)c1cccc(C(F)F)n1]

Analogously to the preparation of Intermediate 5-1, 2.40 g (6.93 mmol) of methyl 5-({[6-(difluoromethyl)pyridin-2-yl]carbonyl}amino)-1H-indazole-6-carboxylate (Intermediate 3-2) in 10 ml of THF were reacted with three portions of 3M methylmagnesium bromide solution in diethyl ether (6.9 ml, then stirring at room temperature for 45 min; 11.6 ml, then stirring at room temperature for 2 h; 6.9 ml, then stirring at room temperature for 2 h). After the workup as for Intermediate 5-1, 2.39 g of a crude product were obtained, which were used further without further purification.

Intermediate 6-1

Methyl 2-(3-hydroxy-3-methylbutyl)-5-nitro-2H-indazole-6-carboxylate

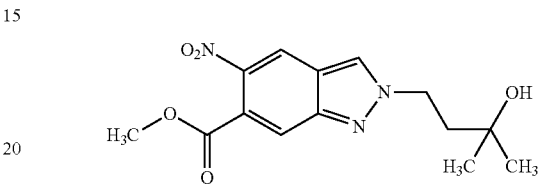

5.00 g (22.6 mmol) of methyl 5-nitro-1H-indazole-6-carboxylate (Intermediate 1-1) were initially charged in 40 ml of DMF. 5.65 g (33.9 mmol) of 4-bromo-2-methylbutan-2-ol, 9.37 g (67.8 mmol) of potassium carbonate and 5.63 g (33.9 mmol) of potassium iodide were added and the mixture was stirred at 100° C. for 20 h. Water was added, the mixture was extracted three times with ethyl acetate and the extracts were washed with sodium chloride solution, filtered through a hydrophobic filter and concentrated. The residue was purified by column chromatography on silica gel (hexane/ethyl acetate). The solids obtained were stirred with diethyl ether, filtered off with suction, washed with diethyl ether and dried. 2.49 g of the title compound were obtained.

UPLC-MS (Method A1): $R_t$=0.93 min (UV detector: TIC), mass found 307.00.

¹H-NMR (400 MHz, DMSO-d₆): δ [ppm]=1.15 (s, 6H), 2.02-2.11 (m, 2H), 3.84 (s, 3H), 4.54 (s, 1H), 4.58-4.65 (m, 2H), 8.05 (s, 1H), 8.69 (s, 1H), 8.86 (s, 1H).

Intermediate 7-1

Methyl 5-amino-2-(3-hydroxy-3-methylbutyl)-2H-indazole-6-carboxylate

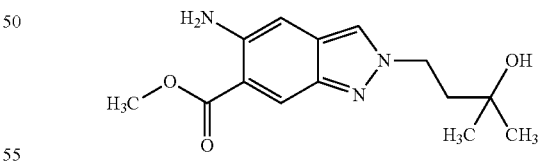

4.53 g of iron and 217 mg of ammonium chloride were added to 2.49 g (8.10 mmol) of methyl 2-(3-hydroxy-3-methylbutyl)-5-nitro-2H-indazole-6-carboxylate (Intermediate 6-1) in 30 ml of ethanol and 10 ml of water, and the mixture was stirred at 90° C. for 21.5 h. The mixture was filtered through Celite and washed through with ethanol three times, and the filtrate was concentrated and the residue was admixed with water. Extraction was effected three times with ethyl acetate (to improve the phase separation, sodium chloride solution was added). The combined organic phases were washed with sodium chloride solution, filtered through a hydrophobic filter and concentrated. This gave 1.95 g (85% of theory) of the title compound.

UPLC-MS (Method A1): $R_t$=0.67 min (UV detector: TIC), mass found 277.00.

$^1$H-NMR (400 MHz, DMSO-$d_6$): δ [ppm]=1.14 (s, 6H), 1.96-2.08 (m, 2H), 3.85 (s, 3H), 4.39-4.51 (m, 3H), 5.81 (s, 2H), 6.80 (s, 1H), 8.05 (s, 1H), 8.18 (s, 1H).

WORKING EXAMPLES

Example 1

N-[6-(2-Hydroxypropan-2-yl)-2-(2-methoxyethyl)-2H-indazol-5-yl]-6-(trifluoromethyl)pyridine-2-carboxamide

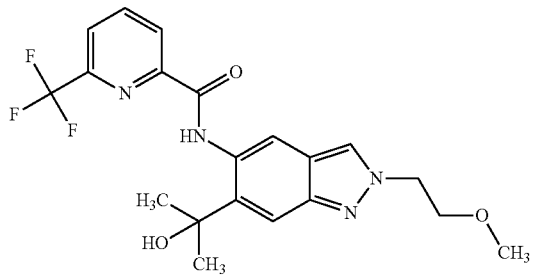 [SMILES: COCCn1cc2cc(NC(=O)c3cccc(C(F)(F)F)n3)c(C(C)(C)O)cc2n1]

75 mg (0.18 mmol) of methyl 2-(2-methoxyethyl)-5-({[6-(trifluoromethyl)pyridin-2-yl]carbonyl}amino)-2H-indazole-6-carboxylate (Intermediate 4-2) were dissolved in 500 μl of THF and admixed with 887 μl (0.89 mmol) of a 1 M methylmagnesium bromide solution in THF. The reaction mixture was stirred at 25° C. for 60 min. Subsequently, 1 ml of a saturated aqueous ammonium chloride solution was added cautiously and the mixture was filtered. The aqueous phase was extracted twice with ethyl acetate, and the organic phases were combined, filtered through a hydrophobic filter and concentrated. The residue was dissolved in 3 ml of DMSO and purified by preparative HPLC. The product-containing fractions were freeze-dried. 20 mg of the title compound were obtained.

UPLC-MS (Method A1): $R_t$=1.08 min

MS (ESIpos): m/z=423 (M+H)$^+$ $^1$H NMR (300 MHz, DMSO-d6): δ [ppm]=1.62 (s, 6H), 3.22 (s, 3H), 3.82 (t, 2H), 4.55 (t, 2H), 5.96 (s, 1H), 7.57 (s, 1H), 8.16 (d1H), 8.29-8.42 (m, 2H), 8.42-8.50 (m, 1H), 8.71 (s, 1H), 12.36 (s, 1H)

Example 2

N-[6-(Hydroxymethyl)-2-(2-methoxyethyl)-2H-indazol-5-yl]-6-(trifluoromethyl)pyridine-2-carboxamide

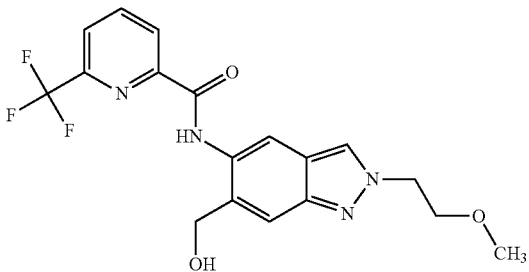 [SMILES: COCCn1cc2cc(NC(=O)c3cccc(C(F)(F)F)n3)c(CO)cc2n1]

13 mg (0.36 mmol) of lithium aluminium hydride were suspended in 1 ml of THF and the mixture was cooled to 0° C. 75 mg (0.17 mmol) of methyl 2-(2-methoxyethyl)-5-({[6-(trifluoromethyl)pyridin-2-yl]carbonyl}amino)-2H-indazole-6-carboxylate (Intermediate 4-2) dissolved in 500 μl of THF were added dropwise and the mixture was stirred at 25° C. for 60 min. The mixture was diluted with water and extracted twice with ethyl acetate, and the combined organic phases were washed with sodium chloride solution, filtered through a hydrophobic filter, concentrated and dried under reduced pressure. This gave 13 mg of the title compound.

UPLC-MS (Method A2): $R_t$=0.99 min

MS (ESIpos): m/z=394 (M+H)$^+$ $^1$H NMR (400 MHz, DMSO-d6): δ [ppm]=3.23 (s, 3H), 3.83 (t, 2H), 4.56 (t, 2H), 4.69 (d, 2H), 5.77 (t, 1H), 7.57 (s, 1H), 8.19 (d, 1H), 8.33-8.41 (m, 2H), 8.43-8.47 (m, 1H), 8.51 (s, 1H), 11.20 (s, 1H)

Example 3

N-[6-(2-Hydroxypropan-2-yl)-2-(3-methoxypropyl)-2H-indazol-5-yl]-6-(trifluoromethyl)pyridine-2-carboxamide

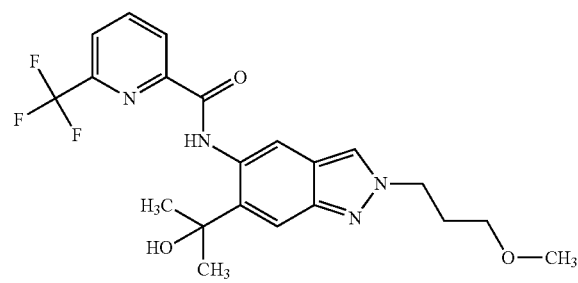 [SMILES: COCCCn1cc2cc(NC(=O)c3cccc(C(F)(F)F)n3)c(C(C)(C)O)cc2n1]

75 mg (0.17 mmol) of methyl 2-(3-methoxypropyl)-5-({[6-(trifluoromethyl)pyridin-2-yl]carbonyl}amino)-2H-indazole-6-carboxylate (Intermediate 4-3) were dissolved in 500 μl of THF and admixed with 859 μl (0.86 mmol) of a 1 M methylmagnesium bromide solution in THF. The reaction mixture was stirred at 25° C. for 60 min. Subsequently, 1 ml of a saturated ammonium chloride solution was added cautiously and the mixture was filtered. The aqueous phase was extracted twice with ethyl acetate, and the organic phases were combined, filtered through a hydrophobic filter and concentrated. The residue was dissolved in 3 ml of DMSO and purified by preparative HPLC. The product-containing fractions were freeze-dried. 25 mg of the title compound were obtained.

UPLC-MS (Method A1): $R_t$=1.13 min

MS (ESIpos): m/z=437 (M+H)$^+$ $^1$H NMR (400 MHz, DMSO-d6): δ [ppm]=1.62 (s, 6H), 2.14 (quin, 2H), 3.23 (s, 3H), 3.26-3.32 (m, 2H), 4.44 (t, 2H), 5.95 (s, 1H), 7.58 (s, 1H), 8.16 (d, 1H), 8.31-8.40 (m, 2H), 8.43-8.48 (m, 1H), 8.72 (s, 1H), 12.36 (s, 1H).

Example 4

N-[6-(Hydroxymethyl)-2-(3-methoxypropyl)-2H-indazol-5-yl]-6-(trifluoromethyl)pyridine-2-carboxamide

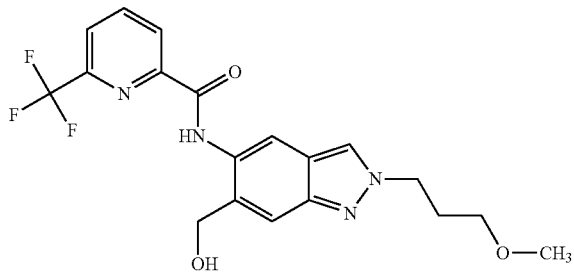 [SMILES: COCCCn1cc2cc(NC(=O)c3cccc(C(F)(F)F)n3)c(CO)cc2n1]

13 mg of lithium aluminium hydride were suspended in THF and the mixture was cooled to 0° C. 75 mg (0.17 mmol) of methyl 2-(3-methoxypropyl)-5-({[6-(trifluoromethyl)pyridin-2-yl]carbonyl}amino)-2H-indazole-6-carboxylate (Intermediate 4-3) in THF were added dropwise and the mixture was allowed to come to room temperature within 30 min. The mixture was diluted with water and filtered, the residue was washed with ethyl acetate and the filtrate was extracted with ethyl acetate. The combined ethyl acetate phases were washed with sodium chloride solution, filtered through a hydrophobic filter and concentrated. The residue was purified by preparative HPLC.

$^1$H NMR (300 MHz, DMSO-d$_6$): δ [ppm]=2.14 (quin, 2H), 3.23 (s, 3H), 3.29 (t, 2H), 4.45 (t, 2H), 4.68 (d, 2H), 5.77 (t, 1H), 7.58 (s, 1H), 8.18 (d, 1H), 8.32-8.48 (m, 3H), 8.51 (s, 1H), 11.21 (s, 1H).

Example 5

N-[2-(2-Hydroxyethyl)-6-(2-hydroxypropan-2-yl)-2H-indazol-5-yl]-6-(trifluoromethyl)pyridine-2-carboxamide

Stage A

Preparation of N-[2-(2-{[tert-butyl(dimethyl)silyl]oxy}ethyl)-6-(2-hydroxypropan-2-yl)-2H-indazol-5-yl]-6-(trifluoromethyl)pyridine-2-carboxamide

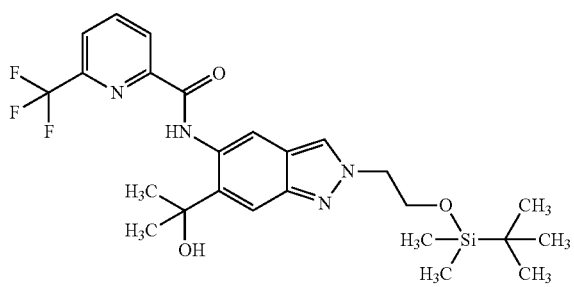 [SMILES: CC(C)(O)c1cc2nn(CCO[Si](C)(C)C(C)(C)C)cc2cc1NC(=O)c1cccc(C(F)(F)F)n1]

100 mg (0.19 mmol) of methyl 2-(2-{[tert-butyl(dimethyl)silyl]oxy}ethyl)-5-({[6-(trifluoromethyl)pyridin-2-yl]carbonyl}amino)-2H-indazole-6-carboxylate (Intermediate 4-5) were dissolved in 1 ml of THF and admixed with 669 μl (0.67 mmol) of a 1 M methylmagnesium bromide solution in THF. The reaction mixture was stirred at 25° C. for 60 min. Another 287 μl (0.29 mmol) of a 1 M methylmagnesium bromide solution in THF were added and the mixture was stirred at 25° C. for 3 h. Subsequently, 20 ml of a saturated ammonium chloride solution were added cautiously and the mixture was filtered. The aqueous phase was extracted twice with ethyl acetate, and the organic phases were combined, dried over magnesium sulphate, filtered, concentrated and dried under reduced pressure. This gave 50 mg of N-[2-(2-{[tert-butyl(dimethyl)silyl]oxy}ethyl)-6-(2-hydroxypropan-2-yl)-2H-indazol-5-yl]-6-(trifluoromethyl)pyridine-2-carboxamide.

UPLC-MS (Method A2): R$_t$=1.51 min

MS (ESIpos): m/z=523 (M+H)$^+$ $^1$H NMR (300 MHz, DMSO-d6): δ [ppm]=−0.17-0.09 (m, 6H), 0.78 (s, 9H), 1.62 (s, 6H), 4.04 (t, 2H), 4.47 (t, 2H), 5.98 (s, 1H), 7.57 (s, 1H), 8.16 (d, 1H), 8.29 (s, 1H), 8.37 (t, 1H), 8.45 (d, 1H), 8.73 (s, 1H), 12.38 (s, 1H).

Stage B

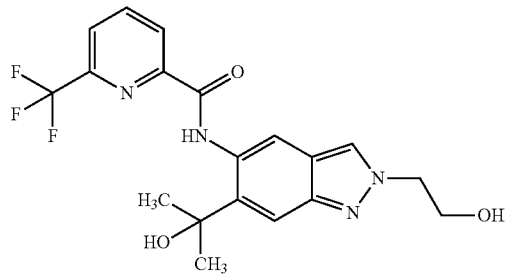 [SMILES: CC(C)(O)c1cc2nn(CCO)cc2cc1NC(=O)c1cccc(C(F)(F)F)n1]

50 mg (96 μmol) of N-[2-(2-{[tert-butyl(dimethyl)silyl]oxy}ethyl)-6-(hydroxymethyl)-2H-indazol-5-yl]-6-(trifluoromethyl)pyridine-2-carboxamide were dissolved in 1.0 ml of THF and admixed with 144 μl (0.14 mmol) of a 1 M solution of tetrabutylammonium fluoride in THF. The reaction mixture was stirred at room temperature for 1 h. The mixture was diluted with water and extracted twice with ethyl acetate, and the combined organic phases were washed with saturated sodium chloride solution, filtered through a hydrophobic filter and concentrated. This gave 36 mg of N-[2-(2-hydroxyethyl)-6-(2-hydroxypropan-2-yl)-2H-indazol-5-yl]-6-(trifluoromethyl)pyridine-2-carboxamide (Example 5).

$^1$H-NMR (400 MHz, DMSO-d$_6$): d [ppm]=1.62 (s, 6H), 3.86 (q, 2H), 4.43 (t, 2H), 4.95 (t, 1H), 5.94 (s, 1H), 7.57 (s, 1H), 8.16 (dd, 1H), 8.30 (s, 1H), 8.37 (t, 1H), 8.45 (d, 1H), 8.72 (s, 1H), 12.36 (s, 1H).

UPLC-MS (Method A2): R$_t$=0.97 min (UV detector: TIC), mass found 408.00.

Example 6

N-[6-(2-Hydroxypropan-2-yl)-2-(3-hydroxypropyl)-2H-indazol-5-yl]-6-(trifluoromethyl)pyridine-2-carboxamide

Stage A

Preparation of N-[2-(3-{[tert-butyl(dimethyl)silyl]oxy}propyl)-6-(2-hydroxypropan-2-yl)-2H-indazol-5-yl]-6-(trifluoromethyl)pyridine-2-carboxamide

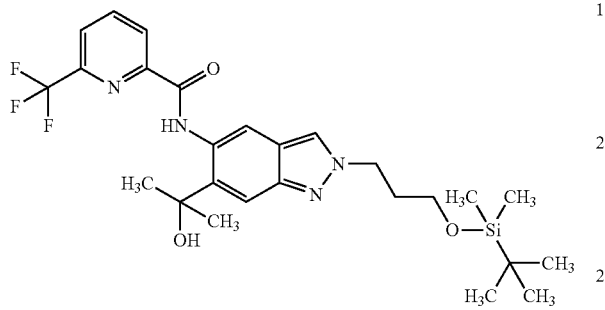

50 mg (0.09 mmol) of methyl 2-(3-{[tert-butyl(dimethyl)silyl]oxy}propyl)-5-({[6-(trifluoromethyl)pyridin-2-yl]carbonyl}amino)-2H-indazole-6-carboxylate (Intermediate 4-6) were dissolved in 500 µl of THF and admixed with 326 µl (0.33 mmol) of a 1 M methylmagnesium bromide solution in THF. The reaction mixture was stirred at 25° C. for 60 min. Subsequently, 20 ml of a saturated ammonium chloride solution were added cautiously and the mixture was extracted twice with ethyl acetate. The combined organic phases were filtered through a hydrophobic filter, concentrated and dried under reduced pressure. The residue was purified by preparative HPLC. 40 mg of N-[2-(3-{[tert-butyl(dimethyl)silyl]oxy}propyl)-6-(2-hydroxypropan-2-yl)-2H-indazol-5-yl]-6-(trifluoromethyl)pyridine-2-carboxamide were obtained.

UPLC-MS (Method A1): $R_t$=1.58 min
MS (ESIpos): m/z=537 (M+H)$^+$
$^1$H NMR (300 MHz, DMSO-d6): δ [ppm]=0.02-0.05 (m, 6H), 0.84-0.91 (m, 9H), 1.62 (s, 6H), 2.02-2.18 (m, 2H), 3.55-3.62 (m, 2H), 4.45 (t, 2H), 5.96 (s, 1H), 7.57 (s, 1H), 8.16 (d, 1H), 8.31 (s, 1H), 8.33-8.42 (m, 1H), 8.45 (d, 1H), 8.72 (s, 1H), 12.37 (s, 1H).

Stage B

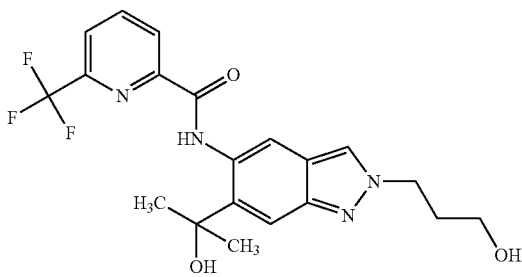 [SMILES: CC(C)(O)c1cc2nn(CCCO)cc2cc1NC(=O)c1cccc(C(F)(F)F)n1]

37 mg (0.07 mmol) of N-[2-(3-{[tert-butyl(dimethyl)silyl]oxy}propyl)-6-(2-hydroxypropan-2-yl)-2H-indazol-5-yl]-6-(trifluoromethyl)pyridine-2-carboxamide were dissolved in 500 µl of THF and admixed with 207 µl (0.21 mmol) of a 1 M solution of tetrabutylammonium fluoride in THF. The reaction mixture was stirred at 25° C. for 2 h. The mixture was diluted with water and extracted twice with ethyl acetate, and the combined organic phases were washed with saturated sodium chloride solution, filtered and concentrated. After purification by preparative HPLC, 10 mg of N-[6-(2-hydroxypropan-2-yl)-2-(3-hydroxypropyl)-2H-indazol-5-yl]-6-(trifluoromethyl)pyridine-2-carboxamide (Example 6, contained secondary component) were obtained.

UPLC-MS (Method A2): $R_t$=1.00 min
MS (ESIpos): m/z=423 (M+H)$^+$
$^1$H NMR selected signals (400 MHz, DMSO-d6): δ [ppm]=1.61 (s), 2.00-2.12 (m), 3.38 (t, 2H), 4.44 (t, 2H), 4.62 (br. s., 1H), 5.93 (br. s., 1H), 7.55 (s, 1H), 8.13 (d, 1H), 8.27-8.38 (m, 2H), 8.43 (d, 1H), 8.71 (s, 1H), 12.30 (br. s., 1H).

Example 7

N-[2-(2-Hydroxyethyl)-6-(hydroxymethyl)-2H-indazol-5-yl]-6-(trifluoromethyl)pyridine-2-carboxamide

Stage A

N-[2-(2-{[tert-Butyl(dimethyl)silyl]oxy}ethyl)-6-(hydroxymethyl)-2H-indazol-5-yl]-6-(trifluoromethyl)pyridine-2-carboxamide

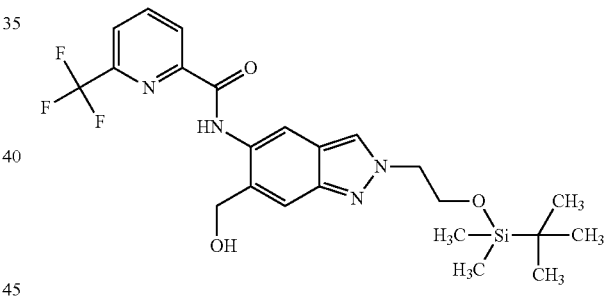

100 mg (0.19 mmol) of methyl 2-(2-{[tert-butyl(dimethyl)silyl]oxy}ethyl)-5-({[6-(trifluoromethyl)pyridin-2-yl]carbonyl}amino)-2H-indazole-6-carboxylate (Intermediate 4-5) were dissolved in 1 ml of THF and admixed with 191 µl (0.38 mmol) of a 2 M lithium borohydride solution. The mixture was left to stir at 25° C. for 24 h. 14 mg (0.38 mmol) of sodium borohydride and 500 µl of methanol were added, and the mixture was stirred at 25° C. for 4 h. Another 14 mg (0.38 mmol) of sodium borohydride were added, and the mixture was stirred at 25° C. for 24 h. Water was added cautiously to the reaction mixture and the organic phase was removed. The mixture was then extracted twice with ethyl acetate, and the combined organic phases were washed with saturated sodium chloride solution, filtered through a hydrophobic filter and concentrated. The residue was taken up in 2 ml of DMSO and purified by preparative HPLC. This gave 30 mg of N-[2-(2-{[tert-butyl(dimethyl)silyl]oxy}ethyl)-6-(hydroxymethyl)-2H-indazol-5-yl]-6-(trifluoromethyl)pyridine-2-carboxamide.

UPLC-MS (Method A2): $R_t$=1.44 min
MS (ESIpos): m/z=495 (M+H)$^+$

¹H NMR (300 MHz, DMSO-d6): δ [ppm]=−0.16-0.12 (m, 6H), 0.75-0.79 (m, 9H), 4.05 (t, 2H), 4.48 (t, 2H), 4.69 (d, 2H), 5.75-5.77 (m, 1H), 7.57 (s, 1H), 8.18 (dd, 1H), 8.30-8.33 (m, 1H), 8.38 (t, 1H), 8.45 (d, 1H), 8.51 (s, 1H), 11.20 (s, 1H).

Stage B

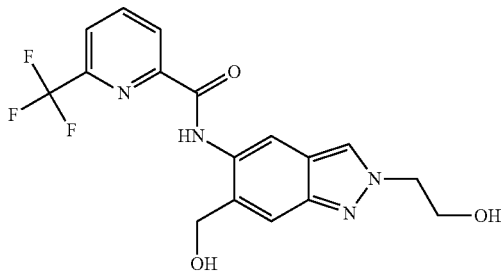 [SMILES: O=C(Nc1cc2cn(CCO)nc2cc1CO)c1cccc(C(F)(F)F)n1]

33 mg (0.07 mmol) of N-[2-(2-{[tert-butyl(dimethyl)silyl]oxy}ethyl)-6-(hydroxymethyl)-2H-indazol-5-yl]-6-(trifluoromethyl)pyridine-2-carboxamide were dissolved in 1 ml of THF and admixed with 100 μl (0.10 mmol) of a 1 M solution of tetrabutylammonium fluoride in THF. The reaction mixture was stirred at 25° C. for 1 h. The mixture was diluted with water and extracted twice with ethyl acetate, and the combined organic phases were washed with saturated sodium chloride solution, filtered through a hydrophobic filter, concentrated and dried under reduced pressure. 25 mg of N-[2-(2-hydroxyethyl)-6-(hydroxymethyl)-2H-indazol-5-yl]-6-(trifluoromethyl)pyridine-2-carboxamide (Example 7) were obtained.

UPLC-MS (Method A2): $R_t$=0.87 min

MS (ESIpos): m/z=381 (M+H)$^+$

¹H NMR (300 MHz, DMSO-d6): δ [ppm]=3.87 (q, 2H), 4.44 (t, 2H), 4.69 (d, 2H), 4.98 (t, 1H), 5.70-5.81 (m, 1H), 7.57 (s, 1H), 8.11-8.23 (m, 1H), 8.31-8.42 (m, 2H), 8.43-8.49 (m, 1H), 8.51 (s, 1H), 11.20 (s, 1H).

Example 8

N-[6-(2-Hydroxypropan-2-yl)-2-(oxetan-3-ylmethyl)-2H-indazol-5-yl]-6-(trifluoromethyl)pyridine-2-carboxamide

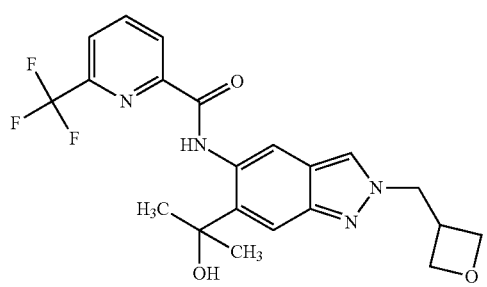 [SMILES: CC(C)(O)c1cc2nn(CC3COC3)cc2cc1NC(=O)c1cccc(C(F)(F)F)n1]

50 mg (0.12 mmol) of methyl 2-(oxetan-3-ylmethyl)-5-({[6-(trifluoromethyl)pyridin-2-yl]carbonyl}amino)-2H-indazole-6-carboxylate (Intermediate 4-1) were dissolved in 500 μl of THF and admixed with 576 μl (0.58 mmol) of a 1 M methylmagnesium bromide solution in THF. The reaction mixture was stirred at 25° C. for 60 min. Subsequently, 20 ml of a saturated aqueous ammonium chloride solution were added cautiously and the mixture was concentrated. The aqueous phase was extracted twice with ethyl acetate, and the organic phases were combined, dried over magnesium sulphate, filtered and concentrated. The residue was dissolved in 2.0 ml of DMSO and purified by preparative HPLC. The product-containing fractions were freeze-dried. 30 mg of the title compound were obtained.

UPLC-MS (Method A2): $R_t$=1.03 min

MS (ESIpos): m/z=435 (M+H)$^+$

¹H NMR (400 MHz, DMSO-d6): δ [ppm]=1.62 (s, 6H), 3.45-3.61 (m, 1H), 4.48 (t, 2H), 4.66 (dd, 2H), 4.72 (d, 2H), 5.94 (s, 1H), 7.57 (s, 1H), 8.16 (d, 1H), 8.33-8.42 (m, 2H), 8.42-8.47 (m, 1H), 8.72 (s, 1H), 12.36 (s, 1H).

Example 9

N-[6-(Hydroxymethyl)-2-(oxetan-3-ylmethyl)-2H-indazol-5-yl]-6-(trifluoromethyl)pyridine-2-carboxamide

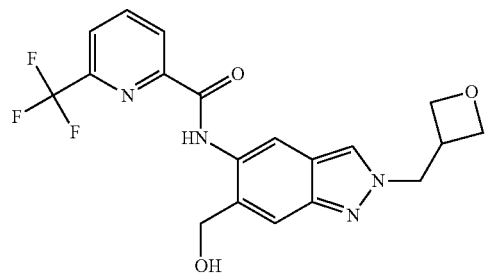 [SMILES: O=C(Nc1cc2cn(CC3COC3)nc2cc1CO)c1cccc(C(F)(F)F)n1]

75 mg (0.17 mmol) of methyl 2-(oxetan-3-ylmethyl)-5-({[6-(trifluoromethyl)pyridin-2-yl]carbonyl}amino)-2H-indazole-6-carboxylate (Intermediate 4-1) were dissolved in 1 ml of a mixture of THF/methanol (1:1), and 8 mg (0.21 mmol) of sodium borohydride were added. The mixture was left to stir at 25° C. for 60 min. The reaction mixture was concentrated, and the residue was admixed with water. The suspension was stirred vigorously for 15 min, and the solids were filtered off with suction, washed twice with water and twice with diethyl ether, and dried under reduced pressure. 48 mg of the title compound were obtained.

UPLC-MS (Method A2): $R_t$=0.94 min

MS (ESIpos): m/z=407 (M+H)$^+$

¹H NMR (300 MHz, DMSO-d6): δ [ppm]=3.55 (s, 1H), 4.48 (t, 2H), 4.61-4.77 (m, 6H), 7.57 (s, 1H), 8.18 (dd, 1H), 8.33-8.49 (m, 3H), 8.51 (s, 1H), 11.21 (s, 1H).

Example 10

N-{6-(2-Hydroxypropan-2-yl)-2-[3-(methylsulphonyl)propyl]-2H-indazol-5-yl}-6-(trifluoromethyl)pyridine-2-carboxamide

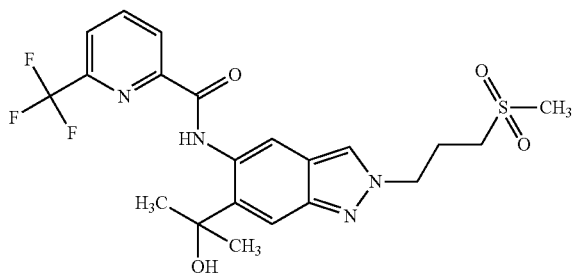 [SMILES: CC(C)(O)c1cc2nn(CCCS(C)(=O)=O)cc2cc1NC(=O)c1cccc(C(F)(F)F)n1]

A mixture of 500 mg (1.32 mmol) of N-[6-(2-hydroxypropan-2-yl)-1H-indazol-5-yl]-6-(trifluoromethyl)pyridine-2-carboxamide (Intermediate 5-1), 569 mg of potassium carbonate and 114 mg of potassium iodide in 5.0 ml of DMF was stirred at room temperature for 15 min. 414 mg of 1-bromo-3-(methylsulphonyl)propane were added and the mixture was stirred at room temperature overnight. Water was added, the mixture was twice extracted with ethyl acetate and the extracts were washed with sodium chloride solution and concentrated. The residue was purified by column chromatography (dichloromethane/methanol gradient). The product fraction was stirred with diethyl ether, filtered and dried. 59 mg of the title compound were obtained.

UPLC-MS (Method A2): $R_t$=1.02 min
MS (ESIpos): m/z=485 (M+H)+
$^1$H-NMR (300 MHz, DMSO-$d_6$): δ [ppm]=1.63 (s, 6H), 2.26-2.42 (m, 2H), 2.99 (s, 3H), 3.06-3.16 (m, 2H), 4.55 (t, 2H), 5.96 (s, 1H), 7.60 (s, 1H), 8.16 (d, 1H), 8.33-8.48 (m, 3H), 8.73 (s, 1H), 12.37 (s, 1H).

Example 11

N-[2-(3-Hydroxy-3-methylbutyl)-6-(2-hydroxypropan-2-yl)-2H-indazol-5-yl]-6-(trifluoromethyl)pyridine-2-carboxamide

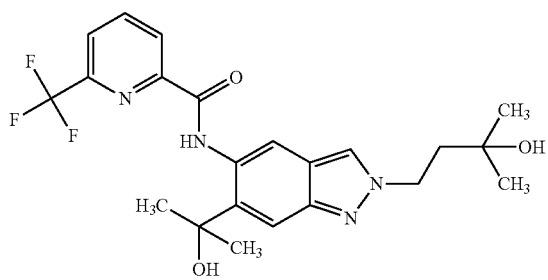 [SMILES: CC(C)(O)CCn1cc2cc(NC(=O)c3cccc(C(F)(F)F)n3)c(C(C)(C)O)cc2n1]

Preparation Method 1

705 mg (1.57 mmol) of methyl 2-(3-hydroxy-3-methylbutyl)-5-({[6-(trifluoromethyl)pyridin-2-yl]carbonyl}amino)-2H-indazole-6-carboxylate (Intermediate 4-4) were initially charged in 10 ml of THF and cooled in an ice-water cooling bath. 2.6 ml (5.0 equivalents) of 3M methylmagnesium bromide solution (in diethyl ether) were added and the mixture was left to stir while cooling with an ice bath for 1 h and at room temperature for 4.5 h. Another 1 equivalent of the methylmagnesium bromide solution was added and the mixture was left to stir at room temperature for 20.5 h. Another 1 equivalent again of the methylmagnesium bromide solution was added and the mixture was left to stir at room temperature for 22 h. The reaction mixture was admixed with saturated aqueous ammonium chloride solution, stirred and extracted three times with ethyl acetate. The combined organic phases were washed with sodium chloride solution, filtered through a hydrophobic filter and concentrated. This gave 790 mg of a residue which was purified by means of preparative HPLC. This gave 234 mg of the title compound and 164 mg of a product fraction which was stirred with diethyl ether. After filtration with suction followed by drying, a further 146 mg of the title compound were obtained.

UPLC-MS (Method A1): $R_t$=1.10 min (UV detector: TIC), mass found 450.00.
$^1$H-NMR (400 MHz, DMSO-$d_6$): δ [ppm]=1.14 (s, 6H), 1.61 (s, 6H), 1.99-2.08 (m, 2H), 4.42-4.55 (m, 3H), 5.93 (s, 1H), 7.56 (s, 1H), 8.15 (dd, 1H), 8.32-8.39 (m, 2H), 8.41-8.47 (m, 1H), 8.70 (s, 1H), 12.34 (s, 1H).

Preparation Method 2

A mixture of 500 mg (1.37 mmol) of N-[6-(2-hydroxypropan-2-yl)-1H-indazol-5-yl]-6-(trifluoromethyl)pyridine-2-carboxamide (Intermediate 5-1), 569 mg of potassium carbonate and 114 mg of potassium iodide in 5 ml of DMF was stirred at room temperature for 15 min. 344 mg (1.5 equivalents) of 4-bromo-2-methylbutan-2-ol were added and the mixture was heated to 100° C. for 2 h. Another 0.5 equivalent of 4-bromo-2-methylbutan-2-ol was added and the mixture was stirred at room temperature for 16 h. The mixture was admixed with water and extracted twice with ethyl acetate, and the combined organic phases were washed with saturated sodium chloride solution and filtered through a hydrophobic filter and concentrated. The residue was purified by column chromatography purification on silica gel (hexane/ethyl acetate). This gave 100 mg of a product fraction which was stirred with diethyl ether. The solid was filtered and dried. 60 mg of the title compound were obtained.

$^1$H-NMR (400 MHz, DMSO-$d_6$): δ [ppm]=1.14 (s, 6H), 1.61 (s, 6H), 1.99-2.07 (m, 2H), 4.43-4.52 (m, 3H) 5.94 (s, 1H) 7.57 (s, 1H) 8.15 (dd, 1H) 8.33-8.40 (m, 2H), 8.42-8.48 (m, 1H), 8.71 (s, 1H), 12.35 (s, 1H)

Example 12

N-{6-(2-Hydroxypropan-2-yl)-2-[2-(methylsulphonyl)ethyl]-2H-indazol-5-yl}-6-(trifluoromethyl)pyridine-2-carboxamide

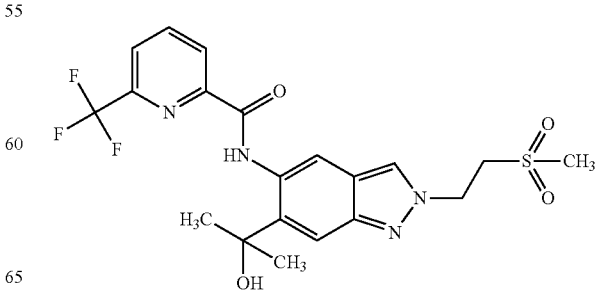

160 mg (0.44 mmol) of N-[6-(2-hydroxypropan-2-yl)-1H-indazol-5-yl]-6-(trifluoromethyl)pyridine-2-carboxamide (Intermediate 5-1) were suspended together with 182 mg of potassium carbonate and 36 mg of potassium iodide in 1.0 ml of DMF, and the mixture was stirred at room temperature for 15 min. Then 123 mg of 2-bromoethyl methyl sulphone (0.66 mmol) were added and the mixture was stirred at room temperature overnight. Water was added, the mixture was extracted twice with ethyl acetate and the extracts were washed with saturated aqueous sodium chloride solution, filtered through a hydrophobic filter and concentrated. Purification of the residue by preparative HPLC gave 20 mg of the title compound.

UPLC (Method A2): $R_t$=1.01 min;
MS (ESIpos): m/z=471 (M+H)+
$^1$H NMR (400 MHz, DMSO-$d_6$): δ [ppm]=1.63 (s, 6H), 2.90 (s, 3H), 3.85 (t, 2H), 4.86 (t, 2H), 5.97 (s, 1H), 7.59 (s, 1H), 8.13-8.19 (m, 1H), 8.37 (s, 1H), 8.41-8.48 (m, 2H), 8.74 (s, 1H), 12.37 (s, 1H).

Example 13

6-(Difluoromethyl)-N-[2-(3-hydroxy-3-methylbutyl)-6-(2-hydroxypropan-2-yl)-2H-indazol-5-yl]pyridine-2-carboxamide

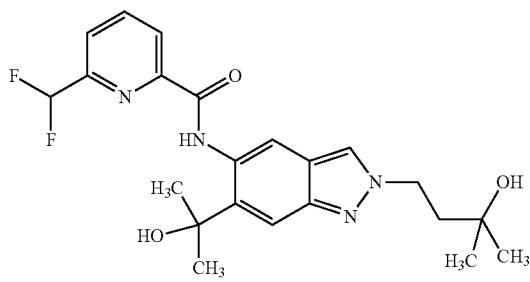 [SMILES: CC(C)(O)CCn1cc2cc(NC(=O)c3cccc(C(F)F)n3)c(C(C)(C)O)cc2n1]

Preparation Method 1

A mixture of 250 mg of 6-(difluoromethyl)-N-[6-(2-hydroxypropan-2-yl)-1H-indazol-5-yl]pyridine-2-carboxamide (crude product of Intermediate 5-2), 144 mg of potassium iodide and 239 mg of potassium carbonate in 2.5 ml of DMF was stirred at room temperature for 15 min. 145 mg (0.87 mmol) of 4-bromo-2-methylbutan-2-ol were added, the mixture was stirred at 110° C. for 3 h, another 96 mg of 4-bromo-2-methylbutan-2-ol were added and the mixture was stirred at 110° C. for 4 h. Water was added, the mixture was extracted twice with ethyl acetate and the extract was washed with semisaturated aqueous sodium chloride solution, filtered through a hydrophobic filter and concentrated. Purification was effected by column chromatography on silica gel (hexane/ethyl acetate). 61 mg of the title compound were obtained.

UPLC-MS (Method A1): $R_t$=1.00 min (UV detector: TIC), mass found 432.00.
$^1$H-NMR (300 MHz, DMSO-$d_6$): δ [ppm]=1.14 (s, 6H), 1.63 (s, 6H), 1.97-2.08 (m, 2H), 4.41-4.55 (m, 3H), 5.99 (s, 1H), 7.03 (t, 1H), 7.56 (s, 1H), 7.94-8.00 (m, 1H), 8.24-8.38 (m, 3H), 8.71 (s, 1H), 12.49 (s, 1H).

Preparation Method 2

Analogously to the preparation of Example 11 (Preparation Method 1), 3.00 g of methyl 5-({[6-(difluoromethyl)pyridin-2-yl]carbonyl}amino)-2-(3-hydroxy-3-methylbutyl)-2H-indazole-6-carboxylate (Intermediate 4-11) were reacted with 3M methylmagnesium bromide solution (in diethyl ether). After purification of the crude product by stirring with diethyl ether, filtering followed by preparative HPLC, 1.37 g of the title compound were obtained.

Example 14

6-(Difluoromethyl)-N-{6-(2-hydroxypropan-2-yl)-2-[2-(methylsulphonyl)ethyl]-2H-indazol-5-yl}pyridine-2-carboxamide

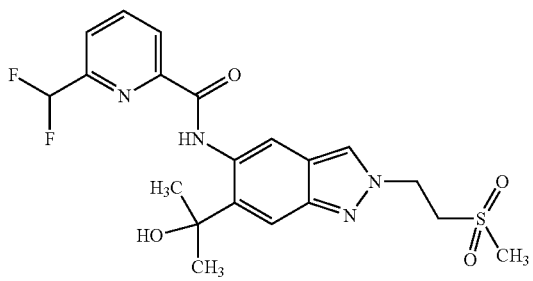 [SMILES: CC(C)(O)c1cc2nn(CCS(C)(=O)=O)cc2cc1NC(=O)c1cccc(C(F)F)n1]

A mixture of 250 mg of 6-(difluoromethyl)-N-[6-(2-hydroxypropan-2-yl)-1H-indazol-5-yl]pyridine-2-carboxamide (crude product of Intermediate 5-2), 144 mg of potassium iodide and 239 mg of potassium carbonate in 2.5 ml of DMF was stirred at room temperature for 15 min. 162 mg of 2-bromoethyl methyl sulphone (0.87 mmol) were added and the mixture was stirred at 110° C. for 3 h. Water was added, the mixture was extracted twice with ethyl acetate and the extract was washed with semisaturated aqueous sodium chloride solution, filtered through a hydrophobic filter and concentrated. The residue was purified by preparative HPLC and the product fractions were additionally purified by column chromatography purification on silica gel (hexane/ethyl acetate). 40 mg of the title compound were obtained.

$^1$H-NMR (400 MHz, DMSO-$d_6$): δ [ppm]=1.65 (s, 6H), 2.90 (s, 3H), 3.85 (t, 2H), 4.85 (t, 2H), 6.03 (s, 1H), 7.04 (t, 1H), 7.59 (s, 1H), 7.98 (d, 1H), 8.25-8.36 (m, 2H), 8.43 (s, 1H), 8.75 (s, 1H), 12.52 (s, 1H).

Example 15

6-(Difluoromethyl)-N-[6-(2-hydroxypropan-2-yl)-2-(3-hydroxypropyl)-2H-indazol-5-yl]pyridine-2-carboxamide Stage A Preparation of N-[2-(3-{[tert-butyl(dimethyl)silyl]oxy}propyl)-6-(2-hydroxypropan-2-yl)-2H-indazol-5-yl]-6-(difluoromethyl)pyridine-2-carboxamide

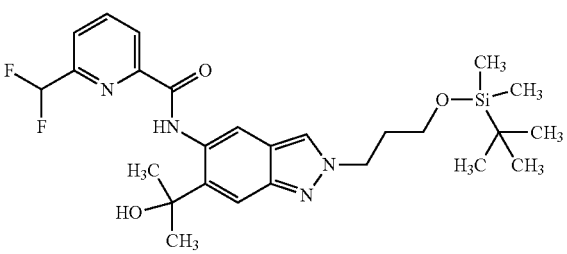 [SMILES: CC(C)(O)c1cc2nn(CCCO[Si](C)(C)C(C)(C)C)cc2cc1NC(=O)c1cccc(C(F)F)n1]

A mixture of 250 mg of 6-(difluoromethyl)-N-[6-(2-hydroxypropan-2-yl)-1H-indazol-5-yl]pyridine-2-carboxamide (Intermediate 5-2), 48 mg of potassium iodide and 239 mg of potassium carbonate in 2.5 ml of DMF was stirred at room temperature for 15 min. 219 mg (0.87 mmol, 1.5 equivalents) of (3-bromopropoxy)(tert-butyl)dimethylsilane were added and the mixture was stirred at 110° C. for 3 h. Another 1 equivalent of (3-bromopropoxy)(tert-butyl)dimethylsilane was added and the mixture was stirred at 100° C. for 4 h. Water was added, the mixture was extracted with ethyl acetate and the extract was washed with aqueous sodium chloride solution, filtered through a hydrophobic filter and concentrated. The residue was purified by column chromatography (hexane/ethyl acetate). 92 mg of the title compound were obtained.

Stage B

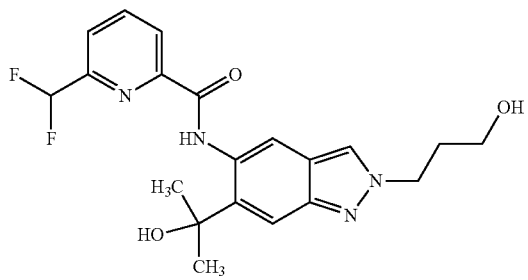 [SMILES: CC(C)(O)c1cc2nn(CCCO)cc2cc1NC(=O)c1cccc(C(F)F)n1]

Analogously to the preparation of Example 6, Stage B, 92 mg of N-[2-(3-{[tert-butyl(dimethyl)silyl]oxy}propyl)-6-(2-hydroxypropan-2-yl)-2H-indazol-5-yl]-6-(difluoromethyl)pyridine-2-carboxamide were reacted with 0.53 ml of a 1 M solution of tetrabutylammonium fluoride in THF within 1 h. Aqueous workup as in Example 6 and purification by preparative HPLC gave 46 mg of the title compound.

UPLC-MS (Method A1): $R_t$=0.92 min (UV detector: TIC), mass found 404.00.

$^1$H-NMR (400 MHz, DMSO-$d_6$): δ [ppm]=1.64 (s, 6H), 2.05 (quin, 2H), 3.35-3.46 (m, 2H), 4.45 (t, 2H), 4.64 (t, 1H), 5.99 (s, 1H), 7.04 (t, 1H), 7.57 (s, 1H), 7.95-7.99 (m, 1H), 8.25-8.36 (m, 3H), 8.73 (s, 1H), 12.50 (s, 1H).

Example 16

N-[6-(2-Hydroxypropan-2-yl)-2-(4,4,4-trifluorobutyl)-2H-indazol-5-yl]-6-(trifluoromethyl)pyridine-2-carboxamide

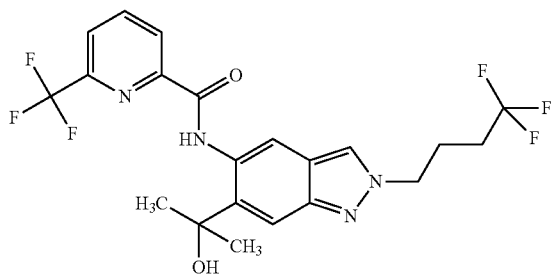 [SMILES: CC(C)(O)c1cc2nn(CCCC(F)(F)F)cc2cc1NC(=O)c1cccc(C(F)(F)F)n1]

A mixture of 210 mg (0.58 mmol) of N-[6-(2-hydroxypropan-2-yl)-1H-indazol-5-yl]-6-(trifluoromethyl)pyridine-2-carboxamide (Intermediate 5-1) in 3 ml of DMF was admixed with 0.11 ml (0.87 mmol) of 1,1,1-trifluoro-4-iodobutane and 239 mg of potassium carbonate, and the mixture was stirred at 80° C. for 6 h. After addition of water, the mixture was extracted three times with ethyl acetate, and the combined organic phases were washed with saturated sodium chloride solution, filtered through a hydrophobic filter and concentrated. The crude product was purified by preparative HPLC. 19 mg of the title compound were obtained.

UPLC-MS (Method A1): $R_t$=1.27 min (UV detector: TIC), mass found 474.15.

$^1$H-NMR (400 MHz, DMSO-$d_6$): δ [ppm]=1.62 (s, 6H), 2.10-2.33 (m), 4.49 (t, 2H), 5.94 (s, 1H), 7.59 (s, 1H), 8.13-8.18 (m, 1H), 8.32-8.41 (m, 2H), 8.41-8.47 (m, 1H), 8.72 (s, 1H), 12.35 (s, 1H).

Example 17

N-{6-(2-Hydroxypropan-2-yl)-2-[3-(trifluoromethoxy)propyl]-2H-indazol-5-yl}-6-(trifluoromethyl)pyridine-2-carboxamide

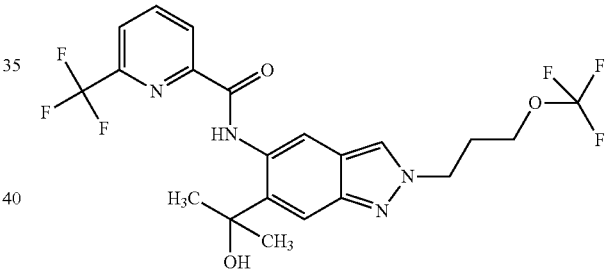

150 mg (0.33 mmol) of N-[6-(2-hydroxypropan-2-yl)-1H-indazol-5-yl]-6-(trifluoromethyl)pyridine-2-carboxamide (Intermediate 5-1) were initially charged in 2 ml of THF. 58 mg (0.40 mmol) of 3-(trifluoromethoxy)propan-1-ol, 131 mg of triphenylphosphine and 71 µl of diisopropyl azodicarboxylate (DIAD, CAS 2446-83-5) were added and the mixture was stirred at room temperature for 19 h. 0.83 ml of sodium hydroxide solution (2M) was added and the mixture was stirred at 40° C. for 5 h. The mixture was diluted with water and extracted three times with ethyl acetate, and the combined organic phases were concentrated and purified by preparative HPLC. 16 mg of the title compound were obtained as a crude product.

UPLC-MS (Method A2): $R_t$=1.26 min (UV detector: TIC), mass found 490.14.

$^1$H-NMR (400 MHz, DMSO-$d_6$, selected signals): δ [ppm]=1.61 (s, 6H), 1.84 (d, 1H), 2.32 (quint., 2H), 4.08 (t, 2H), 4.51 (t, 2H), 7.58 (s, 1H), 8.15 (d, 1H), 8.31-8.39 (m, 2H), 8.44 (d, 1H), 8.72 (s, 1H), 12.35 (s, 1H).

Example 18

N-{6-(2-Hydroxypropan-2-yl)-2-[3-(2,2,2-trifluoroethoxy)propyl]-2H-indazol-5-yl}-6-(trifluoromethyl)pyridine-2-carboxamide

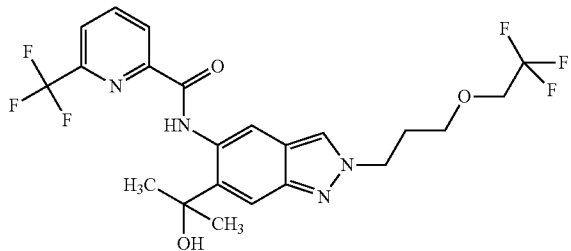 [SMILES: CC(C)(O)c1cc2nn(CCCOCC(F)(F)F)cc2cc1NC(=O)c1cccc(C(F)(F)F)n1]

Analogously to the preparation of Example 11 (Preparation Method 1), 52 mg (0.10 mmol) of methyl 2-[3-(2,2,2-trifluoroethoxy)propyl]-5-({[6-(trifluoromethyl)pyridin-2-yl]carbonyl}amino)-2H-indazole-6-carboxylate (Intermediate 4-10) in 3 ml of THF were reacted with 2×171 µl of 3M magnesium bromide solution in diethyl ether. Purification by preparative HPLC gave 12 mg of the title compound.

UPLC-MS (Method A1): $R_t$=1.25 min (UV detector: TIC), mass found 504.16.

$^1$H-NMR (500 MHz, DMSO-$d_6$): δ [ppm]=1.63 (s, 6H), 2.20 (quin, 2H), 3.58 (t, 2H), 4.05 (q, 2H), 4.47 (t, 2H), 5.94 (s, 1H), 7.58 (s, 1H), 8.15 (dd, 1H), 8.32 (s, 1H), 8.36 (t, 1H), 8.45 (d, 1H), 8.73 (s, 1H), 12.36 (s, 1H).

Example 19

5-Fluoro-N-[2-(3-hydroxy-3-methylbutyl)-6-(2-hydroxypropan-2-yl)-2H-indazol-5-yl]-6-methylpyridine-2-carboxamide

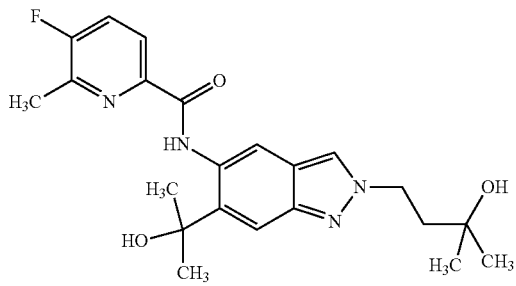 [SMILES: Cc1nc(C(=O)Nc2cc3cn(CCC(C)(C)O)nc3cc2C(C)(C)O)ccc1F]

228 mg (0.31 mmol) of methyl 5-{[(5-fluoro-6-methylpyridin-2-yl)carbonyl]amino}-2-(3-hydroxy-3-methylbutyl)-2H-indazole-6-carboxylate (Intermediate 4-8) were initially charged in 4.5 ml of THF and cooled with an ice cooling bath. 0.63 ml of 3M methylmagnesium bromide solution (in diethyl ether) was added and the mixture was left to stir while cooling with an ice bath for 2 h and at room temperature for 21 h. The reaction mixture was admixed with saturated aqueous ammonium chloride solution and extracted three times with ethyl acetate. The combined organic phases were concentrated. The residue was purified by preparative HPLC. 82 mg of the title compound were obtained.

UPLC-MS (Method A2): $R_t$=1.03 min (UV detector: TIC), mass found 414.21.

$^1$H-NMR (400 MHz, DMSO-$d_6$): δ [ppm]=1.13 (s, 6H), 1.63 (s, 6H), 1.99-2.05 (m, 2H), 2.55-2.59 (m, 3H), 4.42-4.50 (m, 3H), 5.95 (s, 1H), 7.54 (s, 1H), 7.83 (t, 1H), 8.05 (dd, 1H), 8.31 (s, 1H), 8.68 (s, 1H), 12.33 (s, 1H).

Example 20

N-[2-(3-Hydroxy-3-methylbutyl)-6-(2-hydroxypropan-2-yl)-2H-indazol-5-yl]-6-methylpyridine-2-carboxamide

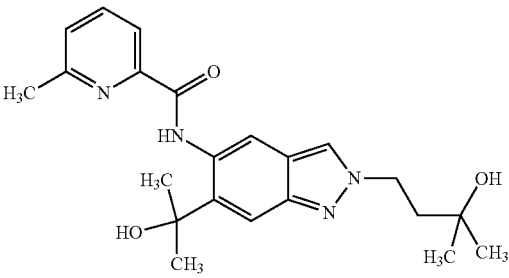 [SMILES: Cc1cccc(C(=O)Nc2cc3cn(CCC(C)(C)O)nc3cc2C(C)(C)O)n1]

278 mg (0.48 mmol) of methyl 2-(3-hydroxy-3-methylbutyl)-5-{[(6-methylpyridin-2-yl)carbonyl]amino}-2H-indazole-6-carboxylate (Intermediate 4-9) were initially charged in 5.0 ml of THF and cooled with an ice cooling bath. 0.97 ml of 3M methylmagnesium bromide solution (in diethyl ether) was added and the mixture was left to stir while cooling with an ice bath for 2 h and at room temperature for 20.5 h. Another 0.48 ml of 3M methylmagnesium bromide solution was added and the mixture was left to stir at room temperature for 67 h. The mixture was admixed with saturated aqueous ammonium chloride solution and extracted three times with ethyl acetate, and the extracts were washed with sodium chloride solution, filtered through a hydrophobic filter and concentrated. The residue was purified by preparative HPLC. 111 mg of the title compound were obtained.

UPLC-MS (Method A2): $R_t$=0.97 min (UV detector: TIC), mass found 396.22.

$^1$H-NMR (400 MHz, DMSO-$d_6$): δ [ppm]=1.15 (s, 6H), 1.64 (s, 6H), 2.00-2.08 (m, 2H), 2.61 (s, 3H), 4.41-4.59 (m, 3H), 5.92 (s, 1H), 7.50 (dd, 1H), 7.56 (s, 1H), 7.90-7.99 (m, 2H), 8.33 (s, 1H), 8.70 (s, 1H), 12.39 (s, 1H).

Example 21

6-(2-Hydroxypropan-2-yl)-N-[6-(2-hydroxypropan-2-yl)-2-(4,4,4-trifluorobutyl)-2H-indazol-5-yl]pyridine-2-carboxamide

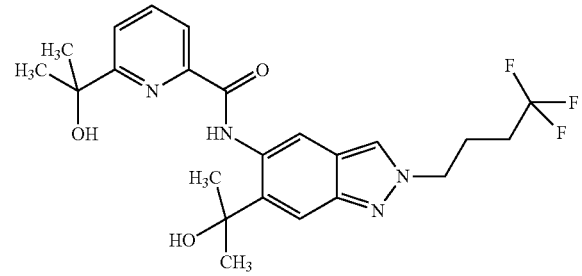 [SMILES: CC(C)(O)c1cccc(C(=O)Nc2cc3cn(CCCC(F)(F)F)nc3cc2C(C)(C)O)n1]

A solution of 72 mg (0.16 mmol) of methyl 5-({[6-(2-hydroxypropan-2-yl)pyridin-2-yl]carbonyl}amino)-2-(4,4,4-trifluorobutyl)-2H-indazole-6-carboxylate (Intermediate 4-7) in 10 ml of THF was cooled in an ice/water cooling bath. 0.26 ml of 3M methylmagnesium bromide solution in diethyl ether was added and the mixture was stirred for 2 h and then at room temperature for 20 h. Another 1 equivalent of the 3M methylmagnesium bromide solution was added and the mixture was stirred at room temperature for 24 h. Saturated aqueous ammonium chloride solution was added, the mixture was three times extracted with ethyl acetate and the extracts were washed with sodium chloride solution and concentrated. Preparative HPLC gave 22 mg (31% of theory) of the title compound.

UPLC-MS (Method A2): $R_t$=1.15 min (UV detector: TIC), mass found 464.20.

$^1$H-NMR (400 MHz, DMSO-$d_6$): δ [ppm]=1.56 (s, 6H), 1.64 (s, 6H), 2.07-2.34 (m, 4H), 4.49 (t, 2H), 5.32 (s, 1H), 6.05 (s, 1H), 7.60 (s, 1H), 7.87 (dd, 1H), 7.99-8.05 (m, 2H), 8.35 (s, 1H), 8.79 (s, 1H), 12.45 (s, 1H).

Example 22

N-{2-[2-(1-Hydroxycyclopropyl)ethyl]-6-(2-hydroxypropan-2-yl)-2H-indazol-5-yl}-6-(trifluoromethyl)pyridine-2-carboxamide

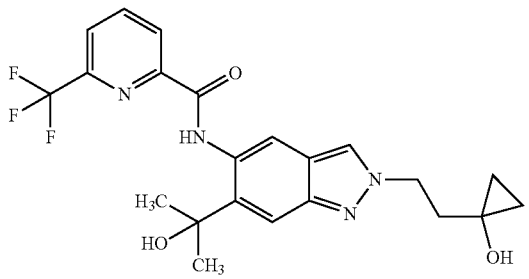 [SMILES: CC(C)(O)c1cc2nn(CCC3(O)CC3)cc2cc1NC(=O)c1cccc(C(F)(F)F)n1]

250 mg (0.69 mmol) of N-[6-(2-hydroxypropan-2-yl)-1H-indazol-5-yl]-6-(trifluoromethyl)pyridine-2-carboxamide (Intermediate 5-1) were initially charged in 5 ml of DMSO. 159 mg (0.96 mmol) of 1-(2-bromoethyl)cyclopropanol, 285 mg of potassium carbonate and 171 mg of potassium iodide were added and the mixture was stirred at 100° C. for 5 h. Water was added and the mixture was extracted three times with ethyl acetate. The combined organic phases were washed with sodium chloride solution, filtered through a hydrophobic filter and concentrated. The residue was purified by preparative HPLC (column: Waters XBridge C18 5μ 100×30 mm, eluent A: water+0.1% by volume of formic acid (99%), eluent B: acetonitrile). Freeze-drying gave 45 mg of the title compound.

$^1$H-NMR (500 MHz, DMSO-d6): δ [ppm]=0.18-0.22 (m, 2H), 0.48-0.52 (m, 2H), 1.62 (s, 6H), 2.08 (t, 2H), 4.54-4.60 (m, 2H), 5.36 (s, 1H), 5.96 (s, 1H), 7.57 (s, 1H), 8.16 (dd, 1H), 8.34-8.39 (m, 2H), 8.45 (d, 1H), 8.72 (s, 1H), 12.36 (s, 1H).

Assessment of Physiological Efficacy
IRAK4 Kinase Assay

The IRAK4-inhibitory activity of the inventive substances was measured in the IRAK4 TR-FRET assay (TR-FRET=Time Resolved Fluorescence Resonance Energy Transfer) described hereinafter.

Recombinant fusion protein from N-terminal GST (glutathione S-transferase) and human IRAK4, expressed in baculovirus-infected insect cells (Hi5, BTI-TN-5B1-4, cell line purchased from Invitrogen, catalogue No. B855-02) and purified via affinity chromatography, was used as enzyme. The substrate used for the kinase reaction was the biotinylated peptide biotin-Ahx-KKARFSRFAGSSPSQAS-FAEPG (C-terminus in amide form) which can be purchased, for example, from Biosyntan GmbH (Berlin-Buch).

For the assay, 11 different concentrations in the range from 20 μM to 0.073 nM were prepared from a 2 mM DMSO solution of the test substance. 50 nl of the respective solution were pipetted into a black low-volume 384-well microtitre plate (Greiner Bio-One, Frickenhausen, Germany), 2 μl of a solution of IRAK4 in assay buffer [50 mM HEPES pH 7.5, 5 mM MgCl2, 1.0 mM dithiothreitol, 30 μM activated sodium orthovanadate, 0.1% (w/v) of bovine gamma-globulin (BGG) 0.04% (v/v) nonidet-P40 (Sigma)] were added and the mixture was incubated for 15 min to allow prebinding of the substances to the enzyme prior to the kinase reaction. The kinase reaction was then started by addition of 3 μl of a solution of adenosine triphosphate (ATP, 1.67 mM=final concentration in 5 μl of assay volume: 1 mM) and peptide substrate (0.83 μM=final concentration in 5 μl assay volume: 0.5 μM) in assay buffer, and the resulting mixture was incubated at 22° C. for the reaction time of 45 min. The concentration of the IRAK4 was adjusted to the respective activity of the enzyme and set such that the assay was carried out in the linear range. Typical concentrations were in the order of about 0.2 nM. The reaction was stopped by addition of 5 μl of a solution of TR-FRET detection reagents [0.1 μM streptavidin-XL665 (Cisbio Bioassays; France, catalogue No. 610SAXLG)] and 1.5 nM anti-phosphoserine antibody [Merck Millipore, "STK Antibody", catalogue No. 35-002] and 0.6 nM LANCE EU-W1024-labelled anti-mouse-IgG antibody (Perkin-Elmer, product No. AD0077; alternatively, it is possible to use a terbium cryptate-labelled anti-mouse-IgG antibody from Cisbio Bioassays) in aqueous EDTA solution (100 mM EDTA, 0.4% [w/v] bovine serum albumin [BSA] in 25 mM HEPES pH 7.5).

The resulting mixture was incubated at 22° C. for 1 h to allow formation of a complex of the biotinylated phosphorylated substrate and the detection reagents. The amount of the phosphorylated substrate was then evaluated by measuring the resonance energy transfer from europium chelate-labelled anti-mouse-IgG antibody to streptavidin-XL665. To this end, the fluorescence emissions at 620 nm and 665 nm were measured after excitation at 350 nm in a TR-FRET measuring instrument, for example a Rubystar (BMG Labtechnologies, Offenburg, Germany) or a Viewlux (Perkin-Elmer). The ratio of the emissions at 665 nm and 622 nm was taken as a measure of the amount of phosphorylated substrate. The data were normalized (enzyme reaction without test substance=0% inhibition; all other assay components but no enzyme=100% inhibition). Typically, the test substances were tested on the same microtitre plates at 11 different concentrations in the range from 20 μM to 0.073 nM (20 μM, 5.7 μM, 1.6 μM, 0.47 μM, 0.13 μM, 38 nM, 11 nM, 3.1 nM, 0.89 nM, 0.25 nM and 0.073 nM). The dilution series were prepared prior to the assay (2 mM to 7.3 nM in 100% DMSO) by serial dilutions. The $IC_{50}$ values were calculated by a 4-parameter fit.

TABLE 1

IC$_{50}$ values of the example compounds in the IRAK4 kinase assay

| Example | IC$_{50}$ [nM] |
|---|---|
| 1 | 30.6 |
| 2 | 135.6 |
| 3 | 7.2 |
| 4 | 52.7 |
| 5 | 264.5 |
| 6 | 35.7 |
| 7 | 867.3 |
| 8 | 15.0 |
| 9 | 103.8 |
| 10 | 18.5 |
| 11 | 3.4 |
| 12 | 10.7 |
| 13 | 1.3 |
| 14 | 10.8 |
| 15 | 12.3 |
| 16 | 21.5 |
| 17 | 36.0 |
| 18 | 47.5 |
| 19 | 8.9 |
| 20 | 13.3 |
| 21 | 117.2 |
| 22 | 3.7 |

The inhibitory activity of the inventive substances of the general formula (III) with respect to IRAK4 was likewise measured in the IRAK4 TR-FRET assay described above. The following are mentioned by way of example: the compound Intermediate 4-2 with an IC$_{50}$=21.7 nM, Intermediate 4-3 with an IC$_{50}$=13.0 nM and Intermediate 4-4 with an IC$_{50}$=6.2 nM.

TNF-α Secretion in THP-1 Cells

This test is suited to test substances for their ability to inhibit secretion of TNF-α (tumour necrosis factor alpha) in THP-1 cells (human monocytic acute leukaemia cell line). TNF-α is a cytokine involved in inflammatory processes. In this test, TNF-α secretion is triggered by incubation with bacterial lipopolysaccharide (LPS).

THP-1 cells were kept in continuous suspension cell culture [RPMI 1460 medium with L-Glutamax (Gibco, Cat. No. 61870-044) supplemented with foetal calf serum (FCS) 10% (Invitrogen, Cat. No. 10082-147), 1% penicillin/streptomycin (Gibco BRL, Cat. No. 15140-114)] and should not exceed a cell concentration of 1×10$^6$ cells/ml. The assay was carried out in cell culture medium (RPMI 1460 medium with L-Glutamax supplemented with FCS 10%).

In each case 2-2.5 μl of the cell suspension (corresponds to 4000 cells) per well were dispensed into a 384-well test plate (Greiner, Cat. No. 784076), in each of which 40-50 nl substance had been dissolved in 100% DMSO. This was done using 10 different concentrations in the range from 20 μM to 0.073 nM for each substance. The cells were incubated at room temperature for 15 min. 2-2.5 μl of 0.1 μg/ml LPS (Sigma, *Escherichia coli* 055:B5, Cat. No. L5418) dissolved in cell culture medium (final concentration 0.05 μg/ml) were then dispensed into each well. As neutral control, cells were treated with 0.05 μg/ml LPS and 1% DMSO and, as inhibitor control, with 1% DMSO only.

The plates were centrifuged at 80 g for 30 s and incubated at 37° C., 5% CO$_2$ and 95% atmospheric humidity for 17 h. The amount of TNF-α was determined using the TNF-alpha HTRF Detection Kit (Cisbio, Cat. No. 62TNFPEB/C). To this end, 2 μl of the detection solution in each case, consisting of anti-TNF-α-XL665 conjugate and anti-TNF-α-cryptate conjugate dissolved in the reconstitution buffer in accordance with the manufacturer's instructions, were added for the HTRF (Homogeneous Time-Resolved Fluorescence) test. After the addition, the mixture was incubated either at room temperature for 3 h or at 4° C. overnight. The signals were then read at 620/665 nm using an HTRF-enabled measuring instrument such as the BMG PheraStar.

The activity of the substances is expressed as the ratio between neutral and inhibitor control in percent. The IC$_{50}$ values were calculated using a 4-parameter fit.

TABLE 2

IC$_{50}$ values of the example compounds with respect to the secretion of TNF-α in THP-1 cells

| Example | IC$_{50}$ [μM] |
|---|---|
| 1 | 1.0 |
| 2 | 15.1 |
| 3 | 0.7 |
| 4 | 5.6 |
| 5 | 5.4 |
| 6 | 0.9 |
| 7 | 16.4 |
| 8 | 1.0 |
| 9 | 6.5 |
| 10 | 1.0 |
| 11 | 0.2 |
| 12 | 0.3 |
| 13 | 0.1 |
| 14 | 0.2 |
| 15 | 0.2 |
| 16 | 0.2 |
| 17 | 0.5 |
| 18 | 0.3 |
| 19 | 0.1 |
| 20 | 0.2 |
| 21 | 1.8 |

In Vitro LPS (Lipopolysaccharide)-Induced Cytokine Production in Human PBMCs (Peripheral Blood Mononuclear Cells)

The effect of the inventive compounds of the general formula (I) on induced cytokine production in human PBMCs was examined. Cytokine production was induced here by LPS, a TLR4 ligand, which leads to activation of the IRAK4-mediated signal path.

The human PBMCs were obtained from anti-coagulated human whole blood. For this purpose, 15 ml of Ficoll-Paque (Biochrom, Cat. No. L6115) were initially pipetted in Leucosep tubes and 20 ml of human blood were added. After centrifugation of the blood at 800 g for 15 min at room temperature, the plasma including the platelets was removed and discarded. The PBMCs were transferred into centrifugation tubes and made up with PBS (phosphate-buffered saline) (Gibco, Cat. No. 14190). The cell suspension was centrifuged at room temperature at 250 g for 10 min and the supernatant was discarded. The PBMCs were resuspended in complete medium (RPMI 1640, without L-glutamine (PAA, Cat. No. E15-039), 10% FCS; 50 U/ml penicillin, 50 μg/ml streptomycin (PAA, Cat. No. P11-010) and 1% L-glutamine (Sigma, Cat. No. G7513)).

The assay was also carried out in complete medium. The PBMCs were seeded in 96-well plates at a cell density of 2.5×10$^5$ cells/well. The inventive compounds were subjected to serial dilution in a constant volume of 100% DMSO and used in the assay at 8 different concentrations in the range from 10 µM to 3 nM such that the final DMSO concentration was 0.4% DMSO. Prior to the actual stimulation, the cells were then pre-incubated therewith for 30 min. To induce cytokine secretion, the cells were stimulated with 0.1 µg/ml LPS (Sigma, *Escherichia coli* 0128:B12, Cat. No. L2887) for 24 hours. Cell viability was determined using the CellTiter-Glo luminescent assay (Promega, Cat. No. G7571 (G755/G756A)) in accordance with the manufacturer's instructions. The amount of secreted TNF-α in the cell culture supernatant was determined using the Human ProInflammatory 9-Plex Tissue Culture Kit (MSD, Cat. No. K15007B) in accordance with the instructions of the manufacturer. By way of example, Example Compound 11 and Example Compound 12 have activity≤1 µM.

In Vitro TLR-4/TLR-7-Induced Interleukin (IL)-23 Secretion of Human Dendritic Cells (DCs)

The effect of the inventive compounds of the general formula (I) on the induced production of the pro-inflammatory cytokine IL-23 which plays an essential role for the generation of TH-17 cells was examined in human DCs. It is stated that TH-17 cells play a crucial role in the pathogenesis of disorders such as rheumatoid arthritis, psoriatic arthritis, Bekhterev's disease (ankylosing spondylitis) or else multiple sclerosis (Lubberts, Nat. Rev. Rheumatol., 2015; Marinoni et al., Auto. Immun. Highlights, 2014; Isailovic et al., J. Autoimmun., 2015; Staschke et al., J Immunol., 2009). To detect the effect of the inventive compounds on IL-23 production, human primary monocytes (isolated from human PBMCs using magnetic separation [Miltenyi Biotech, Monocyte Isolation Kit, Cat. No. 130-091-153] and by the addition of growth factors (recombinant human GM-CSF [PeproTech, Cat. No. 300-03] and IL-4 [PeproTech, Cat. No. 200-04]) in complete medium (VLE (very low endotoxin) RPMI 1640 [Biochrom AG, Cat. No. FG1415], 10% Fetal Bovine Serum (FBS) [Gibco, Cat-No. 10493-106]; 50 µM β-mercaptoethanol (Gibco, Cat. No. 31350], 50 U/ml penicillin and streptomycin [Gibco, Cat. No. 15140-114]) were differentiated in culture over 6 days to DCs. After the DCs had been harvested, they were resuspended in complete medium and seeded in a cell density of $2 \times 10^5$ cells/well in a 96-well plate (Costar, Cat. No. 3599). The inventive compounds were subjected to serial dilution in a constant volume of 100% DMSO and used in the assay at 9 different concentrations in the range from 10 µM to 1 nM. It was ensured here that the DMSO concentration present was always 0.1% DMSO for each of the 9 concentrations used. There was a 30-minute preincubation of the DCs with the inventive compounds. Thereafter, the DCs were stimulated to produce IL-23 by the addition of 10 ng/ml LPS (Sigma, *Escherichia coli* serotype 0127:B8, Cat. No. L3129) (TLR4 ligand) and 2.5 µg/ml of TLR-7/8 ligand R848 (Invivogen, Cat. No. tlrl-r848-5), both activate the IRAK4-mediated signalling pathway, in an incubator (37° C., 95% rH, 5% $CO_2$) for 24 hours. After this incubation time of 24 hours, the supernatants were harvested and analysed using a commercially available hIL-23 ELISA (eBiosciences, Cat. No. 88-7237-88), which was conducted according to the manufacturer's instructions. The results of the inhibition of IL-23 in human DCs are shown by way of example for Example Compound 12 in FIG. 1.

In Vitro TLR-7/8- or TLR-9-Induced IFNα Production of Human Plasmacytoid Dendritic Cells (pDCs)

With the aid of this test, the effect of the inventive compounds of the general formula (I) on the production of IFNα (interferon-alpha) in human pDCs, a key cytokine in the pathogenesis of systemic lupus erythematosus (Mathian et al., Arthritis Rheum, 2009; Crow M. K., Rheum Dis Clin N Am, 2010), can be studied. For this purpose, human PBMCs were isolated from whole blood as described above and the plasmacytoid DCs (pDCs) were isolated therefrom using a commercially available cell separation kit (Miltenyi Biotech, Plasmacytoid Dendritic Cell Isolation Kit II, Cat. No. 130-097-415). The obtained pDCs were resuspended in complete medium (RPMI 1640+GlutaMax [Gibco, Cat. No. 61870-010] supplemented with 10% FBS [Gibco, Cat. No. 10493-106] and 50 U penicillin/streptomycin [Gibco, Cat. No. 15140-114]) and seeded at a cell density of $5 \times 10^4$ cells/well in a 96-well microtitre plate (Costar, Cat. No. 3599). The inventive compounds were subjected to serial dilution in a constant volume of 100% DMSO and used in the assay at 9 different concentrations in the range from 10 µM to 1 nM. It was ensured that the DMSO concentration present was always 0.1% DMSO for each of the 9 concentrations tested. There was a 30-minute preincubation of the pDCs with the inventive compounds. The pDCs were stimulated either with a TLR7/8 ligand (imiquimod, R837, Invivogen, Cat. No. tlrl-imq) or with a TLR-9 ligand (CPG-A, ODN2216, Invivogen, Cat. No. tlrl-2216-1) and this led to activation of the IRAK4-mediated signalling pathways. After incubation for 24 hours, the cell culture supernatants were removed and analysed using a commercially available human IFNα ELISA (IFNalpha Multi-Subtype ELISA Kit, pbl Assay Science, Cat. No. 41105-1). The results of the inhibition of IFNα in human plasmacytoid DCs are shown by way of example for Example Compound 12 in FIG. 2.

In Vivo Model of TLR-Mediated Inflammation

Figure 3:
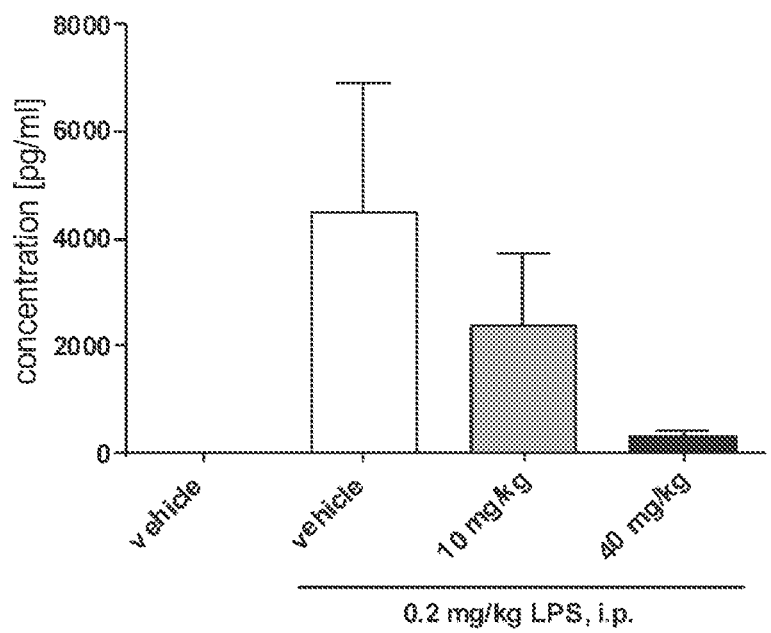

The inventive compounds of the general formula (I) were examined for their in vivo efficacy in a model of in vivo TLR-mediated inflammation. This mechanistic model particularly shows the potential effect of the inventive compounds on TLR4-mediated disorders, since an LPS-mediated inflammation model was used. In this model, female Balb/c mice (about 8 weeks old; Charles River Laboratories, Germany) were divided into groups of 5 animals each. The control group was treated with the vehicle in which the substance had been dissolved (substance vehicle) and also with the vehicle in which the LPS had been dissolved. The substance treatment groups as well as the positive control group received 0.2 mg LPS/kg body weight (Sigma, Cat. No. L4391) (lipopolysaccharides from *E. coli* 0111:B4) intraperitoneally (i.p.). In addition, the positive control group was treated with the substance vehicle described above. The substance was administered orally 16 hours before induction of inflammation by administration of LPS. To examine the effect of the inventive compounds on the inflammation, blood samples were taken from the animals after 1.5 hours. The concentration of particular cytokines in the plasma was determined using the Mouse ProInflammatory 7-Plex Tissue Culture Kit (MSD, Cat. No. K15012B) in accordance with the manufacturer's instructions. IRAK4 inhibitors are effective in the TLR-mediated inflammation model. FIG. 3 shows the amount of TNF-α in the plasma, which is reduced in a dose-dependent manner by administration of Example Compound 11 in comparison with the LPS-induced concentration.

In Vivo Model of IL-1β-Mediated Inflammation

To evaluate the potential efficacy of the inventive compounds of the general formula (I) in IL-1β-mediated disorders, IL-1β was administered i.p. to female Balb/c mice (about 8 weeks old, Charles River Laboratories, Germany) and the effect of the inventive compounds on IL-1β-mediated cytokine secretion was examined. There were 5 animals in each group. The control group was treated with the vehicles used for dissolving the substance and the IL-1β.

Figure 4:
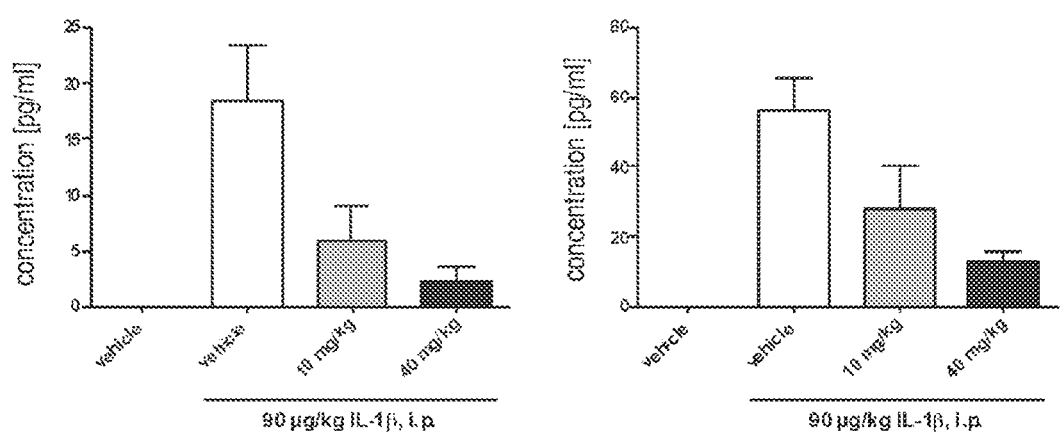

The substance treatment groups and the positive control group were each administered 90 µg IL-1β/kg body weight i.p. (R&D, Cat. No. 401-ML/CF). The substance or its vehicle in the positive control group was administered 6 hours before the administration of IL-1β. 2 hours after administration of the IL-1β, TNF-α was determined in the plasma isolated from the blood using the Mouse ProInflammatory 7-Plex Tissue Culture Kit (MSD, Cat. No. K15012B) in accordance with the manufacturer's instructions. Administration of IL-1β led to an elevated TNF-α plasma concentration which was inhibited by treatment with Example Compounds 11 and 12. This is illustrated by FIG. 4.

In Vivo Adjuvant-Induced Arthritis Model

To determine the anti-inflammatory activity of the inventive compounds of the general formula (I), they were examined for their in vivo efficacy in an arthritis model. For this purpose, male Lewis rats (about 100-125 g, Charles River Laboratories, Germany) were each administered 100 µl of a complete Freund's adjuvant (CFA) solution (*M. tuberculosis* H37Ra [Difo Lab, Cat. No.-231141] dissolved in Incomplete Freund's adjuvant [Difco Lab, Cat. No.-263910]) into the tailhead subcutaneously on day 0. There were n=8 rats in each group. Both a healthy control group and a disease control group were included in the study. Each control group was given p.o. treatment only with the vehicle of the test substance. The treatment with different dosages of the test substance was conducted in a preventative manner, i.e. starting from day 0, by oral administration. On day 0, the starting condition of the animals was additionally determined in terms of the disease activity scores (rating of the severity of arthritis based on a points system). Here, points were awarded according to the extent of joint inflammation from 0 to 4 for the presence of an erythema including joint swelling (0=none; 1=slight; 2=moderate; 3=distinct; 4=severe) for both hind paws and added up. To determine the anti-inflammatory efficacy of the compounds, the disease activity of the animals was scored by means of disease activity scoring starting from day 8, when the animals first exhibit signs of arthritis, and subsequently 3 times per week, until the end (day 20). Statistical analysis was performed using single-factor variance analysis (ANOVA) and by comparison with the control group by means of multiple comparative analysis (Dunnett's test).

Figure 5:
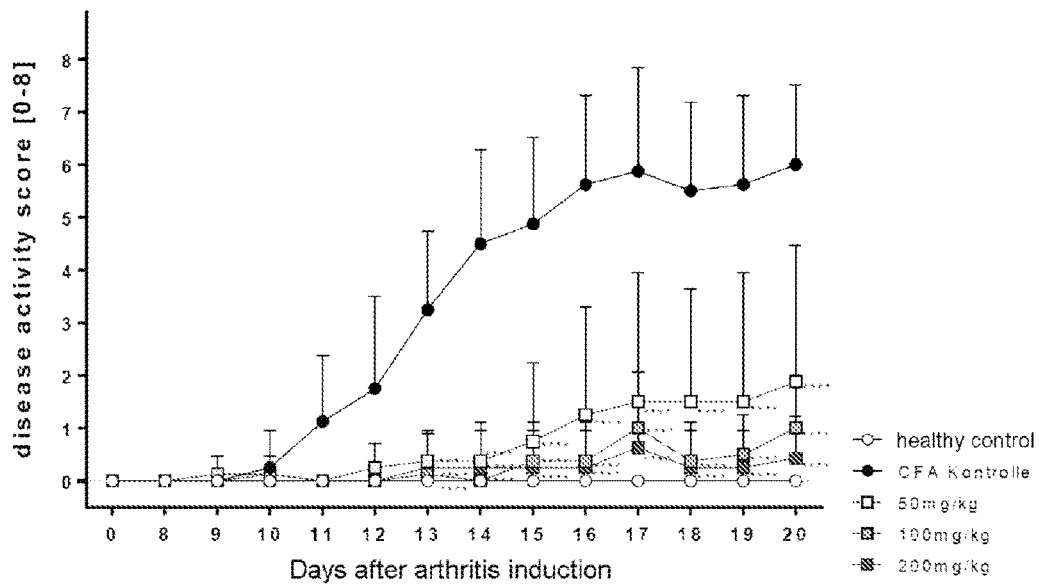

The s.c. administration of CFA in rats leads to acute arthritis with distinct joint inflammation in rats. This induced arthritis was inhibited by the treatment with Example Compound 11. This is illustrated by FIG. 5.

In Vivo Collagen Antibody-Induced Arthritis Model in Mice

The anti-inflammatory effect of the inventive compounds of the general formula (I) was examined in a further murine arthritis model. For this purpose, female Balb/c mice (about 9 weeks old, Charles River Laboratories, Kingston, Canada) were each injected intravenously on day 0 with 200 µl of a collagen antibody cocktail (10 mg/ml; ArthritoMab, MD Bioproducts) into the tail vein (except for the healthy control group included in the study). On day 6, these mice then each received a further intraperitoneal injection of 200 µl of LPS. There were n=10 mice in each group. Both a healthy control group and a disease control group were included in the study. Each control group was given p.o. treatment only with the vehicle of the test substance. The treatment with different dosages of the test substance was conducted in a preventative manner, i.e. starting from day 0, by oral administration. Over the course of the experiment, the extent of disease was scored on the basis of a point award system for the disease activity score on all four paws. In this awarding of points, no points are awarded for a healthy paw, whereas points from 1 [mild inflammation, for example, of the toe(s)] to 4 [severe inflammation extending over the entire paw] are awarded in each case for the particular extent of joint inflammation that has arisen from the toes through the metatarsal joint to the ankle joint, as explained as follows:

0=normal
1=erythema and mild swelling limited to the tarsal or ankle or toes
2=erythema and mild swelling extending from the ankle to the metatarsus (2 segments)
3=erythema and moderate swelling extending from the ankle as far as the metatarsal joints
4=erythema and severe swelling encompassing the metatarsus, foot and toes For this parameter, the starting condition was determined beforehand one day before the start of the experiment (day −1) and this disease activity score was subsequently scored three times per week from day 8 onwards. Statistical analysis was performed using single-factor variance analysis (ANOVA) and by comparison with the control group by means of multiple comparative analysis (Dunnett's test).

Figure 6:
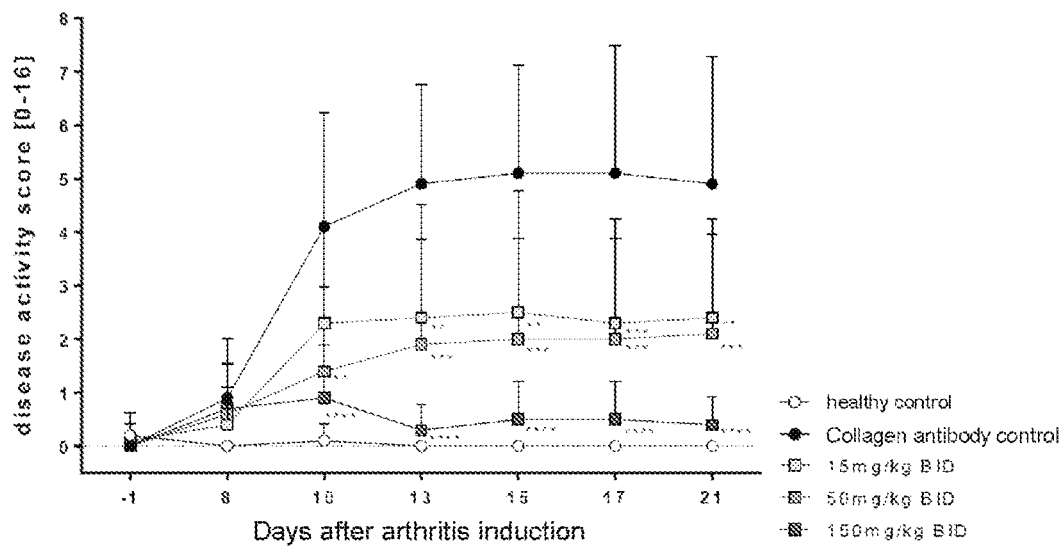

The i.v. administration of a collagen antibody cocktail including the subsequent i.p. administration of LPS in mice leads to acute arthritis with distinct joint inflammation. This induced arthritis was inhibited by the treatment with Example Compound 12. This is illustrated by FIG. 6.

In Vivo NASH Mouse Model

To experimentally induce NASH, 200 µg streptozotocin (STZ; Sigma-Aldrich, USA) is each injected subcutaneously in 45 male 2-day-old C57BL/6 mice. Starting at 4 weeks of age, these animals are fed ad libitum with a high-fat diet (HFD; 57 kcal % fat, #HFD32 from CLEA, Japan). At an age of 6 weeks, the animals are randomized into 3 groups (15 animals per group). While one of the groups does not receive any treatment, the other 2 groups are daily orally treated either with vehicle or the test substance over 4 weeks. After the 4-week treatment, all animals are sacrificed painlessly under anaesthesia, and the livers are removed and fixed for the histological study in Bouin's solution (H. Denk, "Fixierung histologischer Praparate" [Fixing of Histological Preparations], in: P. Böck (ed.): "Romeis Mikroskopische Technik" [Romei's Microscopy Techniques], Urban & Schwarzenberg, Munich-Vienna-Baltimore 1989, 17th edition, page 97, ISBN 3-541-11227-1). Thereafter, the liver samples are embedded in paraffin and 5 µm-thick paraffin sections are produced. Histological sections of each liver are stained a) for the determination of the NAFLD activity score (NAS) with haematoxylin-eosin (HC), and b) for the determination of liver fibrosis with Picro-Sirius red (Waldeck, Germany). The NAFLD activity score is determined in the haematoxylin-eosin sections on the basis of the criteria recommended by D. E. Kleiner et al., Hepatology 41 (2005), 1313-1321 (Table 1). For the histological quantification of fibrotic areas, 5 digital photos (DFC280; Leica, Germany) are taken for each section under 200-fold microscope enlargement and the percentage of fibrosis is determined using the ImageJ Software (National Institute of Health, USA).

In Vivo db/db Mouse Model 30 male 8-week-old db/db mice are used. This model is a well accepted model for obesity, insulin resistance and type 2 diabetes (Aileen J F King; The use of animal models in diabetes research; British Journal of Pharmacology 166 (2012), 877-894). During the experiment, the animals receive a standard diet (RM1(E) 801492, SDS) and tap water ad libitum. The animals are randomized into 3 groups (10 animals per group) and treated orally with the test substance over 6 weeks. During the study period, blood is taken from the animals at different time points (before start of treatment, 3 weeks after start of treatment and 2 days before the end of treatment) to determine insulin sensitivity parameters (e.g. HbA1c, glucose content, insulin content). In addition, an OGTT (oral glucose tolerance test) as a parameter for determination of insulin sensitivity is conducted 1 day before start of treatment and 2 days after the end of treatment. In addition, the HOMA-IR index (fasting insulin level (mU/l) * fasting glucose level (mmol/1)/22.5) is calculated.

In Vivo B-Cell Lymphoma-Associated Xenotransplantation Model

The anti-tumour activity of the inventive compounds of the general formula (I) is studied in murine xenotransplantation models. For this purpose, female C.B-17 SCID mice are implanted subcutaneously with human B-cell lymphoma cell lines, e.g. TMD-8. At a mean tumour size of 20-30 mm$^2$, oral monotherapeutic treatment is started with an inventive compound or by administration of an inventive compound in combination with a standard therapy, each administered orally. However, the animals are randomized beforehand. The treatment is ended as soon as the untreated control group has large tumours. The tumour size and body weight are determined three times per week. Decreases in body weight are a measure of treatment-related toxicity (>10%=critical, stoppage in treatment until recovery, >20%=toxic, termination). The tumour area is detected by an electronic caliper gauge [length (mm)×width (mm)]. At the end of the study, the tumour weight is also determined. The anti-tumour efficacy defines the ratio of tumour weight of treatment vs. control (T/C) [tumour weight of the treatment group on day x/tumour weight of the control group on day x] or the ratio of the tumour area of treatment vs. control [tumour area of the treatment group on day x/tumour area of the control group on day x]. A compound having a T/C greater than 0.5 is defined as active (effective). Statistical analysis is preformed using single-factor ANOVA and by comparison with the control group by means of pair-by-pair comparative analysis (Dunnett's test).

FIG. 1: Inhibition of IL-23 in human monocyte-generated DCs for Example Compound 12. Data are shown as mean values with standard deviations.

Figure 2:
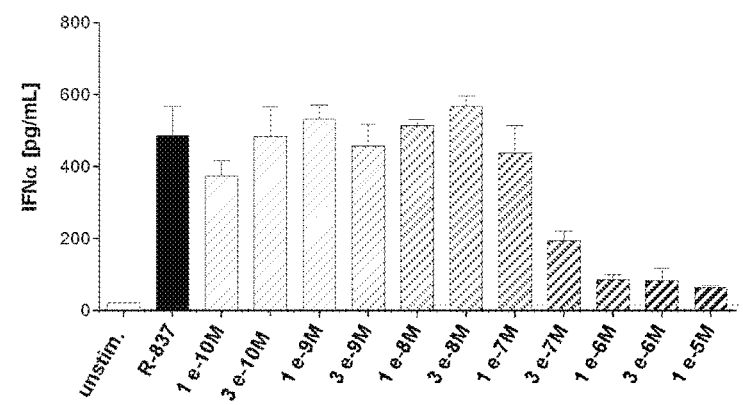
Figure 2:
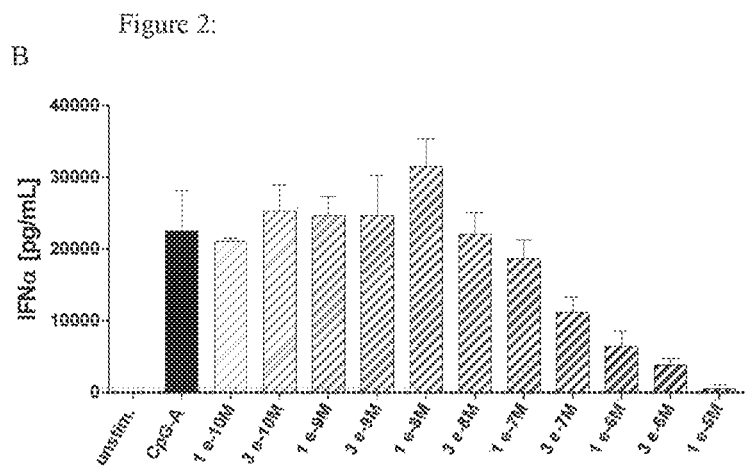

FIG. 2: Inhibition of INF-α in (A) imiquimod (R837)- or (B) CpG-A-stimulated human plasmacytoid DCs for Example Compound 12. Data are shown as mean values with standard deviations.

FIG. 3: Treatment of an LPS-induced inflammation with Example Compound 11 leads to a reduced amount of secreted TNF-α. Data are shown as mean values with standard deviations.

FIG. 4: Treatment of an IL-1β-induced inflammation with Example Compounds 11 (left) and 12 (right) leads to a dose-dependent reduction in the amount of secreted TNF-α. Data are shown as mean values with standard deviations.

FIG. 5: Anti-inflammatory effects of Example Compound 11 in an animal model of rheumatoid arthritis (adjuvant-induced rat model). Significant and dose-dependent inhibition of rheumatic joint inflammation measured on the basis of the disease activity score. The data corresponds to the mean values+standard deviations. Single-factor ANOVA variance analysis with subsequent multiple comparative analysis with the CFA control group by means of Dunnett's test; *p<0.05; p<0.01;*p<0.001; ****p<0.0001.

FIG. 6: Anti-inflammatory effects of Example Compound 12 in an animal model of rheumatoid arthritis (collagen antibody-induced mouse model). Significant and dose-dependent inhibition of rheumatic joint inflammation measured on the basis of the disease activity score. The data corresponds to the mean values+standard deviations. The statistical significances between collagen antibody (AK) control and the treatment groups were calculated by means of single-factor ANOVA variance analysis with subsequent multiple comparative analysis (Dunnett's test) (*p<0.05; p<0.01;*p<0.001; ****p<0.0001).

The invention claimed is:

1. A method for treatment and/or prophylaxis of allergic dermatitis in a non-human animal comprising administering to the non-human animal an effective amount of compound having the structure:

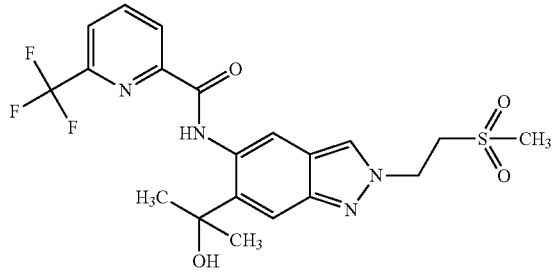 [SMILES: CC(C)(O)c1cc2nn(CCS(C)(=O)=O)cc2cc1NC(=O)c1cccc(C(F)(F)F)n1]

or a metabolite, a salt, a solvate, a solvate of the salt thereof.

2. The method according to claim 1, wherein the allergic dermatitis is atopic dermatitis.

3. The method according to claim 2, wherein the method is treatment of atopic dermatitis.

4. The method according to claim 1, wherein the allergic dermatitis is allergic contact dermatitis.

5. The method according to claim 4, wherein the method is treatment of allergic contact dermatitis.

6. The method according to claim 1, wherein the method is treatment, and the allergic dermatitis is atopic dermatitis or allergic contact dermatitis.

7. The method according to claim 1, wherein the compound is administered to the non-human animal in a dosage form comprising at least one pharmaceutically suitable excipient.

8. The method according to claim 3, wherein the compound is administered to the non-human animal in a dosage form comprising at least one pharmaceutically suitable excipient.

9. The method according to claim 5, wherein the compound is administered to the non-human animal in a dosage form comprising at least one pharmaceutically suitable excipient.

* * * * *